US006751290B2

(12) United States Patent
Salb

(10) Patent No.: US 6,751,290 B2
(45) Date of Patent: Jun. 15, 2004

(54) RADIOGRAPHIC ASSESSMENT OF TISSUE AFTER EXPOSURE TO A COMPOUND

(75) Inventor: Jesse Salb, Los Angeles, CA (US)

(73) Assignee: Veritas Pharmaceuticals, Inc., Los Angeles, CA (US)

( * ) Notice: Subject to any disclaimer, the term of this patent is extended or adjusted under 35 U.S.C. 154(b) by 545 days.

(21) Appl. No.: 09/811,079

(22) Filed: Mar. 16, 2001

(65) Prior Publication Data

US 2002/0039401 A1 Apr. 4, 2002

Related U.S. Application Data

(63) Continuation-in-part of application No. 09/149,734, filed on Sep. 8, 1998, now Pat. No. 6,226,352.
(60) Provisional application No. 60/190,330, filed on Mar. 16, 2000.

(51) Int. Cl.[7] .............................................. H05G 1/64
(52) U.S. Cl. .................................................... 378/98.9
(58) Field of Search .......................... 378/98.9, 51, 62, 378/143

(56) References Cited

U.S. PATENT DOCUMENTS

| 2,840,602 A | 6/1958 | Larsen |
| 3,701,771 A | 10/1972 | Almen et al. ............ 260/211 R |
| 3,702,866 A | 11/1972 | Salveson et al. |
| 3,854,049 A | 12/1974 | Mistretta et al. ............ 250/402 |
| 3,974,386 A | 8/1976 | Mistretta et al. ............ 250/402 |

(List continued on next page.)

FOREIGN PATENT DOCUMENTS

| EP | 0 270 340 | 6/1988 |
| WO | WO 98/57669 | 12/1998 |
| WO | WO 01/67958 A2 | 9/2001 |

OTHER PUBLICATIONS

PCT International Search Report for PCT Int'l Appln No. US01/08612, mailed Aug. 16, 2002 (9 pages).

Xu, Yiming et al. "Synthesis of Radioiodinated 1–Deoxy–Nojirimycin Derivatives: Novel Glucose Analogs," *Nuclear Medicine and Biology*, vol. 26, No. 7, p. 833–839 (1999), Document No. XP–001037809, no month.

Magata, Yasuhiro et al. "Development of a Novel Radioiodinated Glucose Derivative with Interaction to Hexokinase," *Journal of Labelled Compounds and Radiopharmaceuticals*, vol. 31, No. 4, p. 317–328 (1992), Document No. XP–000675967. No mo.

(List continued on next page.)

*Primary Examiner*—William Oen
(74) *Attorney, Agent, or Firm*—Blakely, Sokoloff, Taylor & Zafman LLP

(57) ABSTRACT

Radiographic system and method for noninvasively assessing the response of tissue to a compound, such as a therapeutic compound. In one embodiment, a non-radioactive, radio-opaque imaging agent accumulates in tissue in proportion to the tissue concentration of a predefined cellular target. The imaging agent is administered to a live organism, and after an accumulation interval, radiographic images are acquired. The tissue being examined is transilluminated by X-ray beams with preselected different mean energy spectra, and a separate radiographic image is acquired during transillumination by each beam. An image processing system performs a weighted combination of the acquired images to produce a first image. The image processing procedure isolates the radiographic density contributed solely by differential tissue accumulation of the imaging agent. A compound is administered to the organism, and after a selected interval, a second radiographic image of the tissue is acquired. Radiographic density contributed by accumulated imaging agent in corresponding areas of tissue in the first and second images are compared. Differences in radiographic density between the images reflect changes in the concentration of the cellular target that have occurred after administration of the compound. The system and method may be used to assess therapeutic efficacy of compounds in the drug discovery process, in clinical trials, and in the evaluation of clinical treatment. In other embodiments, pharmacological and toxicological effects of a wide variety of compounds on tissue may be noninvasively assessed.

90 Claims, 13 Drawing Sheets

U.S. PATENT DOCUMENTS

| | | | |
|---|---|---|---|
| 4,021,481 A | 5/1977 | Almen et al. | |
| 4,139,605 A | 2/1979 | Felder et al. | |
| 4,160,015 A | 7/1979 | Wiegert | |
| 4,243,653 A | 1/1981 | Sovak et al. | 424/5 |
| 4,250,113 A | 2/1981 | Nordal et al. | 564/153 |
| 4,341,756 A | 7/1982 | Sovak et al. | |
| 4,348,377 A | 9/1982 | Felder et al. | |
| 4,352,788 A | 10/1982 | Felder et al. | |
| 4,364,921 A | 12/1982 | Speck et al. | 424/5 |
| 4,406,878 A | 9/1983 | DeBoer | |
| 4,439,613 A | 3/1984 | Sovak et al. | |
| 4,455,292 A | 6/1984 | Bertoni | 424/5 |
| 4,474,747 A | 10/1984 | Dimo et al. | |
| 4,716,225 A | 12/1987 | Ledley et al. | 536/122 |
| 4,766,110 A | 8/1988 | Ryan et al. | |
| 4,887,604 A * | 12/1989 | Shefer et al. | 128/654 |
| 5,043,152 A | 8/1991 | Schaefer et al. | |
| 5,093,042 A | 3/1992 | Counsell et al. | 260/408 |
| 5,141,739 A | 8/1992 | Jung et al. | 424/4 |
| 5,198,977 A | 3/1993 | Salb | 364/413.01 |
| 5,408,996 A | 4/1995 | Salb | 128/633 |
| 5,466,786 A | 11/1995 | Buhr et al. | 536/26.26 |
| 5,525,327 A | 6/1996 | Baker et al. | |
| 5,609,851 A | 3/1997 | Bennani et al. | |
| 5,610,289 A | 3/1997 | Cook et al. | 536/25.34 |
| 5,650,135 A | 7/1997 | Contag et al. | |
| 5,728,527 A | 3/1998 | Singer et al. | 435/6 |
| 5,729,620 A | 3/1998 | Wang | 382/128 |
| 5,763,208 A | 6/1998 | Bischofberger et al. | 435/40.5 |
| 5,796,862 A | 8/1998 | Pawlicki et al. | |
| 5,817,289 A | 10/1998 | Klaveness et al. | |
| 6,071,491 A * | 6/2000 | Epstein et al. | 424/1.49 |
| 6,226,352 B1 | 5/2001 | Salb | |
| 2001/0031035 A1 | 10/2001 | Salb et al. | |
| 2001/0038682 A1 | 11/2001 | Salb | |

OTHER PUBLICATIONS

Lutz, T. et al. "$^{123}$I–Iodobenzoylglucosamines: Glucose Analogues for Heart Imaging," *Journal of Labelled Compounds and Radiopharmaceuticals*, vol. 33, No. 4, p. 327–344 (1993), Document No. XP–008002378, no month.

Anderson et al., "What does positron emission tomography offer oncology?". *Eur. J. Cancer* 36:2028–2035 (2000), no month.

Bender et al., "Possible role of FDG–PET in the early prediction of therapy outcome in liver metastases of colorectal cancer", *Hybridoma* 18: 87–91 (1999). No mo.

Brock et al., "Early evaluation of tumour metabolic response using [18F]fluorodeoxyglucose and positron emission tomography: a pilot study following the phase II chemotherapy schedule for temozolomide in recurrent high–grade gliomas". *Br. J. Cancer* 82:608–615 (2000). No mo.

Conti et al., "PET and [18F]–FDG in oncology: a clinical update", *Nuc. Med. Biol.* 23:717–735 (1996).

Dehdashti et al., "Positron emission tomographic assessment of "metabolic flare" to predict response of metastatic breast cancer to antiestrogen therapy", *Eur. J. Nucl. Med.* 26: 51–56 (1999). No mo.

Findlay et al., "Noninvasive monitoring of tumor metabolism using fluorodeoxyglucose and positron emission tomography in colorectal cancer liver metastases: correlation with tumor response to fluorouracil", *J. Clin. Oncol.* 14: 700–708 (1996). No mo.

Fischman, "Positron Emission Tomography in the Clinical Evaluation of Metastatic Cancer", *J. Clin. Oncol.* 14: 691–696 (1996). No mo.

Fischman, "The role of positron emission tomography in pharmacokinetic analysis", *Drug Metab. Rev.* 29: 923–956 (1997). No mo.

Fowler et al., "PET and drug research and development". *J. Nucl. Med.* 40:1154–1163 (1999). No mo.

Geran et al., "Protocols for screening chemical agents and natural products against animal tumors and other biological systems", *Cancer Chemother. Rep.* 3: 51–61 (1972). No mo.

Green et al., "Noninvasive methods for quantitating blood time–activity curves from mouse PET images obtained with fluorine–18–fluorodeoxyglucose", *J. Nucl. Med.* 39: 729–734 (1998). No mo.

Hendrikse et al., "Visualization of multidrug resistance in vivo". *Eur. J. Nucl. Med.* 26:283–293 (1999), no month.

Hietala, "Ligand–receptor interactions as studied by PET: implications for drug development", *Ann. Med.* 31: 438–443 (1999). No mo.

Hoh et al., "PET in oncology: will it replace the other modalities?", *Semin. Nuc. Med.* 27:94–106 (1997). No mo.

Hoey & Smith, in Sovak ed., "Handbook of Experimental Pharmacology: Radiocontrast Agents", 73: 22–125, Springer–Verlag, New York (1984), No mo.

Jerusalem et al., "Whole–body positron emission tomography using 18F–fluorodeoxyglucose for posttreatment evaluation in Hodgkin's disease and non–Hodgkins's lymphoma has higher diagnostic and prognostic value than classical computed tomography scan imaging", *Blood* 94: 429–433 (1999). No mo.

Knuuti et al. "PET as a cardiovascular and metabolic research tool", *Ann. Med.* 31: 450–456 (1999). No mo.

Price & Jones "Can Positron Emission Tomography (PET) be Used to Detect Subclinical Response to Cancer Therapy?", *Eur J Cancer* 31A: 1924–1927 (1995). No mo.

Romer et al., "Positron emission tomography in non–Hodgkin's lymphoma: assessment of chemotherapy with fluorodeoxyglucose", *Blood* 91: 4464–4471 (1998). No mo.

Schelling et al., "Positron emission tomography using [(18)F]Fluorodeoxyglucose for monitoring primary chemotherapy in breast cancer". *J. Clin. Oncol.* 18:1689–1695 (2000). No mo.

Schulte et al., "Evaluation of neoadjuvant therapy response of osteogenic sarcoma using FDG PET". *J. Nucl. Med.* 40:1637–1643 (1999). No mo.

Smith et al., "Positron emission tomography using [(18)F]–fluorodeoxy–D–glucose to predict the pathologic response of breast cancer to primary chemotherapy", *J. Clin. Oncol.* 18:1676–1688 (2000). No mo.

Sovak et al. "Contrast media: a journey almost sentimental". *Invest Radiol.* 29: Suppl 1:S4–14 (1994), no month.

Vallburg et al. "Drug development, radiolabelled drugs and PET", *Ann. Med.* 31: 432–437 (1999). No mo.

Wahl et al., "Metabolic monitoring of breast cancer chemo-hormonotherapy using positron emission tomography: initial evaluation", *J. Clin. Oncol.* 11:2101–2111 (1993). No mo.

Weber et al., "Reproducibility of metabolic measurements in malignant tumors using FDG PET", *J. Nucl. Med.* 11:1771–1777 (1999). No mo.

Yoshioka et al., "Influence of chemotherapy on FDG uptake by human cancer xenografts in nude mice", *J Nucl. Med* 38: 714–717 (1997). No mo.

Zhang et al., "Bioluminescence for biological sensing in living mammals". *Adv. Exp. Med. Biol.* 471:755–784 (1999). No mo.

PCT International Search Report for PCT Appln No. PCT/US01/08485, mailed Oct. 24, 2001 (9 pages).

PCT International Search Report for PCT Appln No. PCT/US01/08663, mailed Oct. 24, 2001 (9 pages).

Bech, Lars; Diemer, Nils Henrik; and Gjedde, Albert. "Metabolic effect of topical application of metrizamide to rat brain cortex." *Acta Neurol Scand.*, vol. 72, pp. 427–431 (Jun. 1985).

Gjedde, Albert. "The blood–brain barrier is impermeable to metrizamide." *Acta Neurol. Scandiv.* vol. 66, pp. 392–395 (1982), no month.

Sigel, Peter and Pette, Dirk. "Intracellular localization of glycogenolytic and glycolytic enzymes in white and red rabbit skeletal muscle; a gel film method for coupled enzyme reactions in histochemistry." *The Journal of Histochemistry and Cytochemistry*, vol. 17, No. 4, pp. 225–236 (Sept. 1968).

Agrawal S. et al., "Pharmacokinetics of oligonucleotides", *Ciba Foundation Symposium 209*, pp. 60–78 (1997).

Aleshin A.E. et al., "The mechanism of regulation of hexokinase: new insights from the crystal structure of recombinant human brain hexokinase complexed with glucose and glucose–6–phosphate", *Structure* 6(1):39–50 (1998).

Aller C.B. et al., "Flow cytometric analysis of glucose transport by rat brain cells", *Cytometry* 27:262–268 (1997).

Alpert N.M. et al., "Improved methods for image registration", *Neuroimage* 3:10–18 (1996).

Arora K.K. et al., "Functional significance of mitochondrial bound hexokinase in tumor cell metabolism. Evidence for preferential phosphorylation of glucose by intramitochondrially generated ATP", *J. Biol. Chem.* 263(33):17422–17428 (Nov. 25, 1998).

Barnett J.E.G. et al., "Structural requirements for binding to the sugar–transport system of the human erythrocyte", *Biochem. J.* 131:211–221 (1973).

Barnett J.E.G. et al., "Evidence for two asymmetric conformational states in the human erythrocyte sugar–transport system", *Biochem. J.* 145:417–429 (1975).

Binder C. et al., "Deregulated simultaneous expression of multiple glucose transporter isoforms in malignant cells and tissues", *Anticancer Research*, 17:4299–4304 (1997), no month.

Bird R.E. et al., "Analysis of cancers missed at screening mammography", *Radiology*, 184:613–617 (1992). No mo.

Chien K.R. et al. "In vivo esterification of a synthetic 125I–labeled fatty acid into cardiac glycerolipids", *Am. J. Physiol.* 245:H693–H697 (1983). No mo.

Coats E.A. et al., "Exploring the hexokinase glucose binding site through correlation analysis and molecular modeling of glucosamine inhibitors", *J. Enz. Inhib.* 6:271–282 (1993). No mo.

Colville C.A. et al., "Analysis of the structural requirements of sugar binding to the liver, brain and insulin–responsive glucose transporters expressed in oocytes," *Biochem. J.* 294:753–760 (1993). No mo.

Conti P.S. et al., "PET and [18F]–FDG in oncology: a clinical update", *Nuc. Med. & Biol.* 23:717–735 (1996). No mo.

Crooke S. et al. (eds).: "Designer Antisense Oligonucleotides: conjugation chemistry and functionality placement," *Antisense Research and Applications*, Ch. 17, pp. 303–349, CRC Press, Boca Raton (1993). No mo.

Dewanjee M.K. et al., "Noninvasive imaging of c–myc oncogene messenger RNA with indium–111–antisense probes in a mammary tumor–bearing mouse model", *J. Nuc. Med.* 35(6):1054–1063 (1994).

Eisenhut M. et al., "Trapping and metabolism of radioiodinated PHIPA 3–10 in the rat myocardium", *J. Nucl. Med.* 38(12):1864–1869 (1997).

Ekholm S.E. et al., "Neural tissue uptake and clearance of iohexol following lumbar myelography in rabbits", *Acta Radiologica Diagnosis* (Stockh). 26:331–336 (1985).

Elmore J.G. et al., "Ten–year risk of false positive screening mammograms and clinical breast examinations", *N. Eng. J. Med.* 338(16):1089–1096 (1998).

Friston K.J. et al., "Spatial registration and normalization of images", *Human Brain Mapping* 2:165–189 (1995).

Ghose A.K. et al., "Atomic physiochemical parameters for three dimensional structure directed quantitative structure–activity relationships III: Modeling hydrophobic interactions", *J. Comp. Chem.* 9(1):80–90 (1988).

Gjedde A.: "The blood–brain barrier is impermeable to metrizamide", *Acta Neurol. Scandinav.* 66:392–395 (1982), no month.

Golman K.: "Distribution and retention of 125I–labeled metrizamide after intravenous and suboccipal injection in rabbit, rat, and cat", *Acta Radiol. Suppl.* S335:300–311 (1973). No mo.

Hansch C. et al., "Linear relationships between lipophilic character and biological activity of drugs", *J. Pharm. Sci.* 61(1):1–19 (Jan. 1972).

Hansch C. et al., "Exploring QSAR: fundamentals and applications in chemistry and biology", pp. 97–168, *Amer. Chem. Soc.*, Washington, DC (1995). No mo.

Henry C. et al., "[123I]–6–deoxy–6–iodo–D–glucose (6DIG).: a potential tracer of glucose transport", *Nuc. Med. Biol.* 24:527–534 (1997). No mo.

Hoh C.K. et al., "PET in oncology: will it replace the other modalities?", *Seminars in Nuc. Med.* 27(2):94–106 (Apr. 1997).

Hosokawa R., et al., "Myocardial kinetics of Iodine–123–BMIPP in canine myocardium after regional ischemia and reperfusion: implications for clinical SPECT", *J. Nucl. Med.* 38:1857–1863 (1997). No mo.

Kamp F. et al., "Fatty acid flip–flop in phospholipid bilayers is extremely fast", *Biochemistry* 34:11928–11937 (1995). No mo.

Kamp F. et al., "Movement of fatty acids, fatty acid analogues, and bile acids across phospholipid bilayers", *Biochemistry* 32:11074–11086 (1993). No mo.

Kelcz F. et al., "Spectral considerations for absorption–edge fluoroscopy", *Medical Physics* 4(1):26–35 (Jan/Feb 1977).

Kelcz F. et al., "Absorption–edge fluoroscopy using a three–spectrum technique", *Medical Physics* 3(3):159–168 (May/Jun. 1976).

Keller T.H. et al., "Synthesis and hybridization properties of oligonucleotides containing 2'–O–modified ribonucleotides", *Nucleic Acids Res.* 21(19):4499–4505 (1993). No mo.

Kormano M. et al., "Toxicity of X–ray contrast media in cell cultures", *Invest. Radiol.* 15:68–71 (1980), no month.

Loke S.L. et al., "Characterization of oligonucleotide transport into living cells", *Proc. Natl. Acad. Sci. USA* 86:3474–3478 (1989). No mo.

Machulla H.J. et al. "Comparative evaluation of fatty acids labeled with C–11, CI–34m, Br–77, and I–123 for metabolic studies of the myocardium: concise communication", *J. Nucl. Med.* 19:298–302 (1978). No mo.

Macovski A. et al., "Isolated iodine images using spatial–frequency encoding", *Med. Phys.* 6(1):53–58 (Jan/Feb 1979).

Maley F. et al., "Synthesis of N–substituted glucosamines and their effect on hexokinase", *J Biol. Chem.* 214:765–773 (1955). No mo.

Matteucci M., "Oligonucleotide analogues: an overview", *Ciba Foundation Symposium 209*, pp. 5–18 (1997). No mo.

Meylan W.M., "Atom/fragment contribution method for estimating octanol–water partition coefficients", *J. Pharm. Sci.* 84(1):83–92 (1995). No mo.

Mueckler M., "Facilitative glucose transporters", *Eur. J. Biochem.* 219:713–725 (1994), no month.

Nelson C.A. et al., "Targeting of glucose transport proteins for tumor imaging: is it feasible?", *J. Nucl. Med* 37:1031–1037 (1996), no month.

Railton R. et al., "Myocardial scintigraphy with I–123 heptadecanoic acid as a test for coronary heart disease", *Euro. J. Nucl. Med* 13:63–66 (1987). No mo.

Rekker, R.F. et al., "Calculation of Drug Lipophilicity," VCH, Weinheim, pp. 1–43 (1992).

Riederer S.J. et al., "Three–beam K–edge imaging of iodine using differences between fluoroscopic video images: theoretical considerations", *Med. Phys.* 8(4):471–479 (Jul/Aug 1981).

Riederer S.J. et al., "Three–beam K–edge imaging of iodine using differences between fluoroscopic video images: experimental results", *Med. Phys.* 8(4):480–487 (Jul/Aug 1981).

Ries L.A.G. et al. (eds).: "Surveillance, Epidemiology, and End Results Program, 1998," *SEER Cancer Statistics Review*, 1973–1995, National Cancer Institute, 42 pp. (1998). No mo.

Sols A. et al., "Substrate specificity of brain hexokinase", *J. Biol. Chem.* 210:581–595 (1954). No mo.

Speck U., "Basic pharmacology of iodinated contrast media", *Contrast Media*, pp. 1–13, Churchill Livingstone, NY (1988).

St. Charles R. et al., "Molecular model of human beta–cell glucokinase built by analogy to the crystal structure of yeast hexokinase B", *Diabetes* 43:784–791 (1994).

Tavitian B. et al., "In vivo imaging of oligonucleotides with positron emission tomography", *Nature Medicine* 4(4):467–471 (1998).

Torikuza K. et al., "A Phase 1 study of beta–methyl–p–(123I)–iodophenyl–pentadecanoic acid (123I–BMIPP)", *Jpn. J. Nucl. Med.* 28:681–690 (1991).

Trigatti B.L. et al., "The effect of intracellular pH on long–chain fatty acid uptake in 3T3–L1 adipocytes: evidence that uptake involves the passive diffusion of protonated long–chain fatty acids across the plasma membrane", *Biochem. J.* 313:487–494 (1996).

van Dijck J.A. et al., "The current detectability of breast cancer in a mammographic screening program. A review of the previous mammograms of interval and screen–detected cancers", *Cancer* 72(6):1933–1938 (Sep. 15. 1993).

Van Eenige M.J. et al., "Clinical value of studies with radioiodinated heptadecanoic acid in patients with coronary artery disease", *Eur. Heart J.* 11:258–268 (1990), no month.

Wallis M.G. et al., "A review of false negative mammography in a symptomatic population", *Clin. Radiol.* 44:13–15 (1991). No mo.

Weber G., "Molecular correlation concept: ordered pattern of gene expression in neoplasia", *GANN Monograph on Cancer Res.* 13:47–77 (1972), no month.

Weinhouse S., "Glycolysis, respiration, and anomalous gene expression in experimental hepatomas", *Cancer Res.* 32(10):2007–2016 (1972). No mo.

Willson et al., "Yeast hexokinase inhibitors designed from the 3–D enzyme structure rebuilding", *J. Enz. Inhib.* 12:101–121 (1997). No mo.

Woods R.P. et al., "Automated image registration: I. General methods and intrasubject, intramodality validation", *J. Comput. Assist. Tomogr.* 22(1):139–152 (1998). No mo.

Woods R.P. et al., "Automated image registration: II. Intersubject validation of linear and nonlinear models", *J. Comput. Assist. Tomogr.* 22(1):153–165 (1998), no month.

Woods R.P. et al., "MRI–PET registration with automated algorithm", *J. Comput. Assist. Tomogr.* 17(4):536–546 (Jul/Aug1993).

Bech L. et al., "Metabolic effect of topical application of metrizamide to rat brain cortex," Acta Neurol. Scand. vol. 72 pp. 427–431 (1985), no month.

Guidolet J. et al., "Cardiovascular radiology. Subcellular localization of uro–angiographic contrast by 125I–labeled media," Invest. Radiol. vol. 15 pp. S215–S219 (Nov–Dec. 1980).

Nordby A. et al., "Intracellular penetration and accumulation of radiographic contrast media in the rat kidney" (and discussion), Scanning Microsc. 4:3 pp. 651–666 (1990), no month.

Nordby et al., "Incorporation of contrast media in cultured cells," Invest. Radiol. vol. 24 pp. 703–710 (Sep. 1989).

Nordby A. et al., "Effects on the ATP content of cultured cells after radiographic contrast media exposure. Evidence for accumulation of contrast media in cultured cells," Acta Radiol. vol. 30 pp. 541–547 (1989), no month.

Nordby A. et al., "Short–term effects of radiographic contrast media on monolayer cell cultures and hepatocytes," Invest. Radiol. vol. 22, pp. 603–607 (Jul. 1987).

Nordby A. et al., "Effects of radiographic contrast media on monolayer cell cultures," Invest. Radiol. vol. 21 pp. 234–239 (Mar. 1986).

Weichert J.P. et al., "Polyiodinated triglyceride analogs as potential computed tomography imaging agents for the liver," J. Med. Chem. vol. 38 No. 4 pp. 636–646 (1995), no month.

PCT International Search Report for PCT Int'l Appln No. PCT/US99/20298 mailed Apr. 25, 2000 (7 pages).

\* cited by examiner

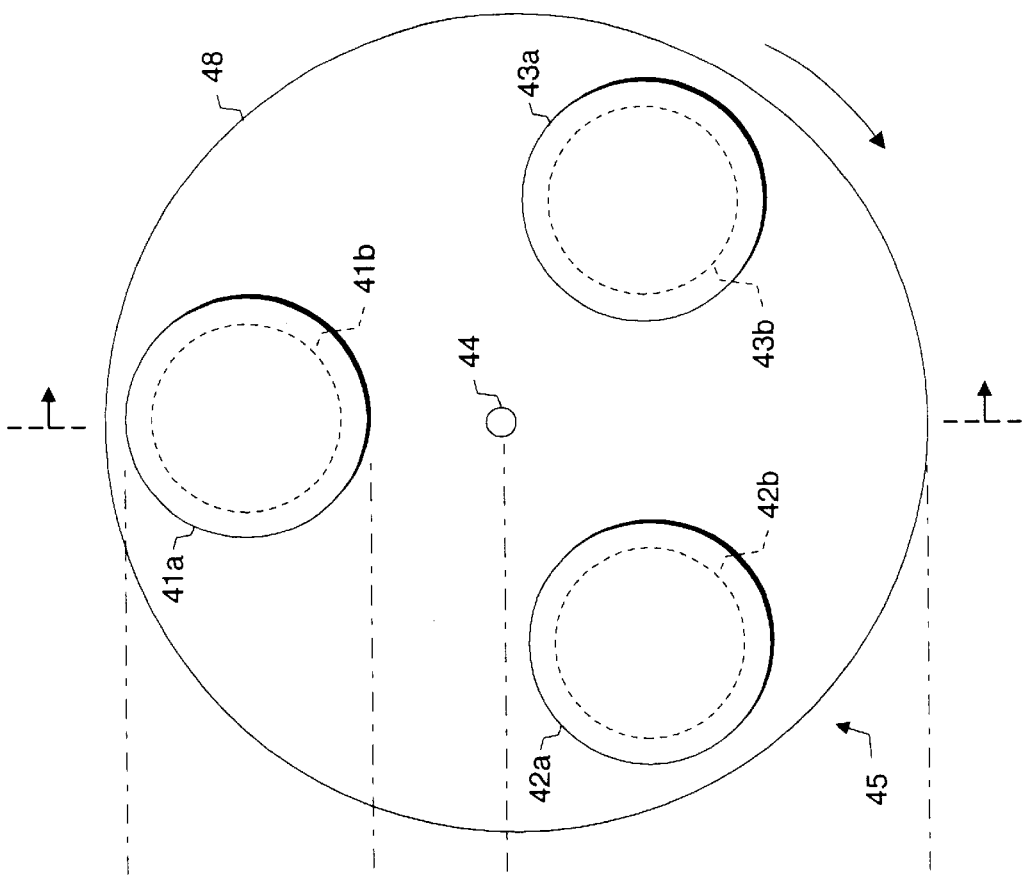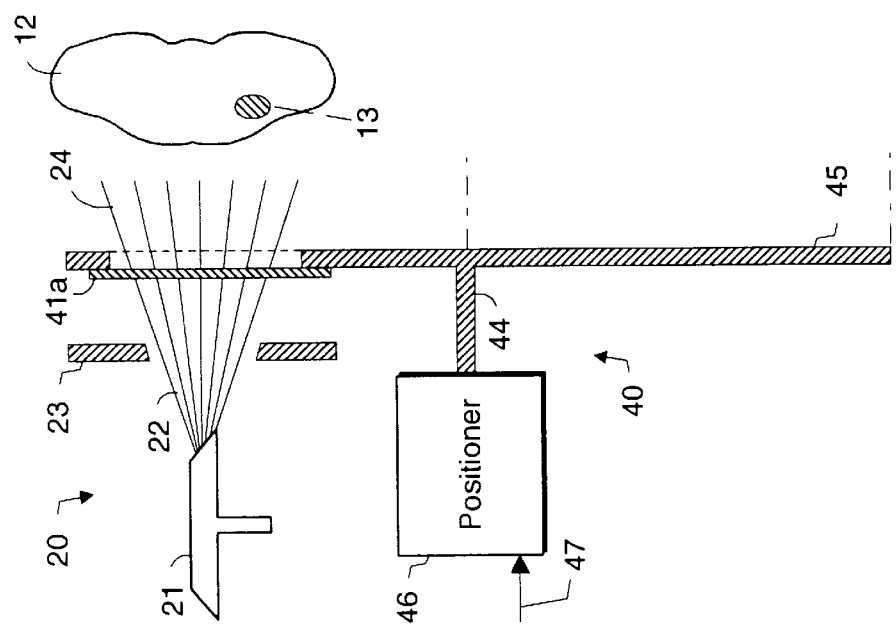

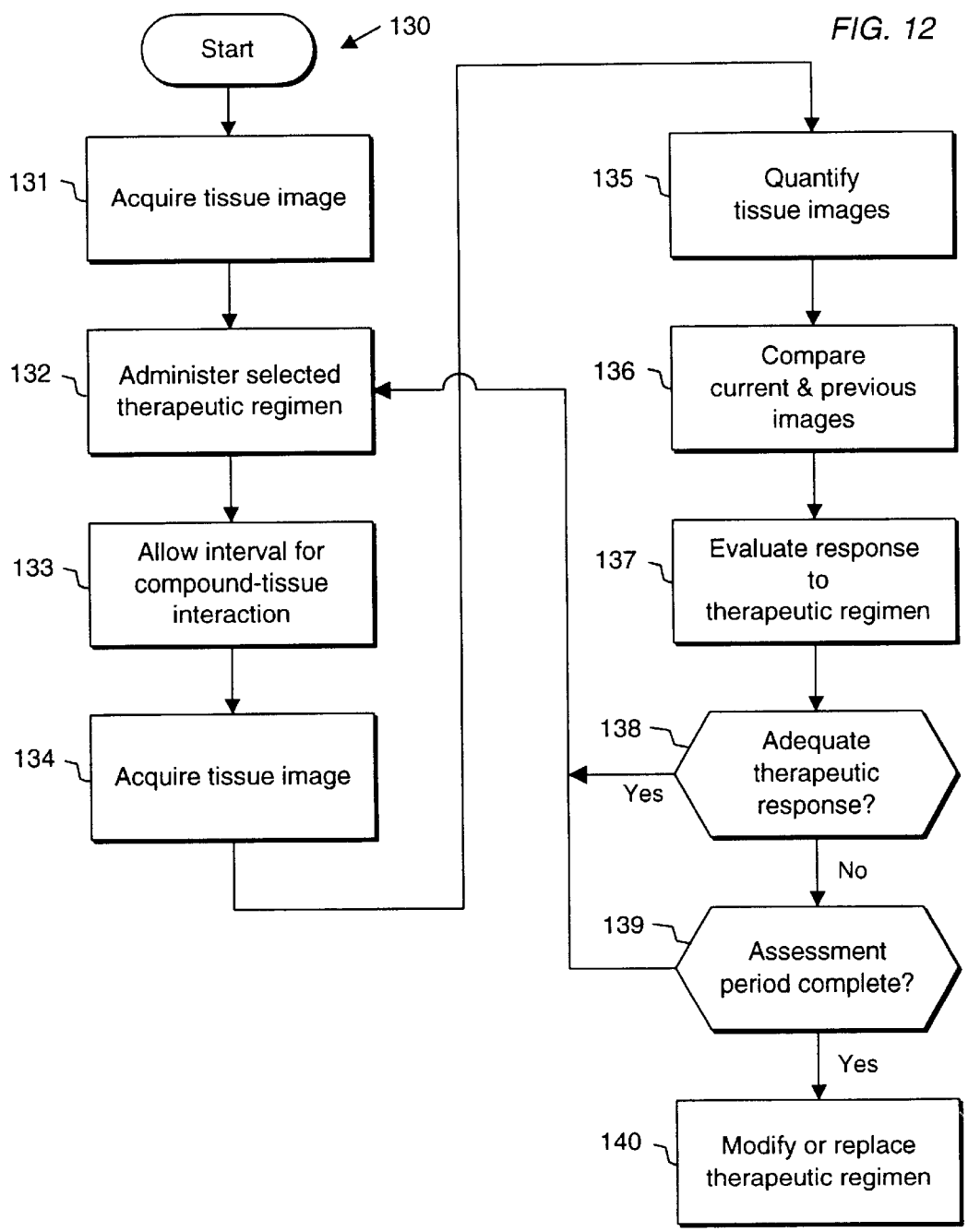

RADIOGRAPHIC ASSESSMENT OF TISSUE AFTER EXPOSURE TO A COMPOUND

This application is a continuation-in-part of co-pending U.S. patent application Ser. No. 09/149,734 which was filed Sep. 8, 1998, now U.S. Pat. No. 6,226,352 and this application hereby claims the benefit of this prior filing date. This application is also a continuation-in-part of co-pending U.S. patent application Ser. No. 60/190,330 which was filed Mar. 16, 2000; this application claims the benefit of the provisional's filing date under 35 U.S.C. § 119(e).

BACKGROUND OF THE INVENTION

A. Field of the Invention

This invention relates to a radiographic system and method for assessing the response of tissue in vivo to compounds, including therapeutic compounds.

B. Description of the Related Art

The ability to accurately assess the effects of compounds in vivo is essential in a wide range of pharmacological and related studies. Assessment of tissue response to compounds is particularly important in each stage of drug discovery, development, and clinical application. Noninvasive studies of tissue response may be particularly useful in the early validation of lead compounds during the drug discovery process, in clinical trials of potential therapeutic compounds, and in monitoring the efficacy of therapeutic compounds already used in clinical practice. These studies may include evaluation of therapeutic efficacy and detection of toxicity and other adverse side effects.

Evaluation of tissue response to compounds in vivo may initially be useful in the lead validation phase of the drug discovery process. Data that must be acquired during this early phase of drug discovery may be classified into three categories: pharmacodynamics, pharmacokinetics and toxicology. Pharmacodynamic studies include the evaluation of therapeutic efficacy in a targeted disease process, the relationship between compound dosage and therapeutic effect, and the duration of action of administered compounds. Pharmacokinetic studies include quantitative measurements of compound absorption, distribution, metabolism, and excretion (ADME). Toxicological studies include determination of gross systemic toxicity, damage to individual organs, and other adverse effects that may be caused by test compounds.

Pharmacodynamic, pharmacokinetic, and toxicological data are now frequently obtained by administering one or multiple doses of a test compound to an animal; killing the animal; and performing anatomical examination of body organs, histological examination of tissue, and analysis of body fluids. This approach to characterization of pharmacological activity has several significant limitations. First, anatomical and histological studies may not precisely reflect significant changes in the activity of relevant biochemical pathways in normal and abnormal tissue after administration of test compounds. Second, because animals must be killed for anatomical and histological studies, serial measurements cannot be performed on an individual animal during and after repeated administration of a test compound. Finally, processing of tissue for histological examination is labor-intensive, time consuming, and expensive, and often represents a serious rate-limiting step in applications such as high-throughput drug discovery.

For these reasons, a rapid, noninvasive method for assessment of tissue response to lead compounds during the early phases of the drug discovery process is highly desirable. The method may desirably enable quantitative measurements of changes in the activity of normal and abnormal biochemical pathways in tissue in response to administered compounds. The method may also desirably permit repeated, noninvasive measurements of the activity of these biochemical pathways in individual animals over long periods of time and over the course of multiple administrations of lead compounds. The method may also desirably allow data to be rapidly acquired and analyzed.

A second area of application for noninvasive assessment of tissue response in vivo is in clinical trials of new pharmaceutical compounds. A rapid, inexpensive method for assessment of tissue response might provide prompt accurate feedback on both efficacy and toxicity of test compounds in patients. Direct noninvasive assessment of tissue response might also provide data complementary to that obtained using measurements such as clinical chemistry studies of blood and urine.

A third application in which noninvasive assessment of tissue response to compounds should prove valuable is in the evaluation of efficacy and toxicity of therapeutic compounds already used in clinical practice. In many diseases processes, the response of abnormal or diseased tissue to therapeutic compounds may vary widely between individual patients. A noninvasive method that could provide prompt accurate feedback on the clinical efficacy of therapeutic compounds in individual patients should be of great value in selecting appropriate therapeutic agents, planning treatment regimens, and predicting outcome.

A number of approaches have been developed for noninvasive measurements of tissue response in vivo. These approaches have generally used techniques of nuclear medicine to generate images of a variety of tissue biochemical pathways. These imaging methods include positron emission tomography (PET) and single photon emission computed tomography (SPECT). A wide variety of radiopharmaceuticals have been successfully employed in PET and SPECT imaging studies. However, certain practical limitations of these modalities have reduced their economic feasibility and restricted their widespread use. These limitations include very high procedure costs, limited availability, need for dedicated imaging devices, and relatively low spatial resolution.

The spatial limitations of radiopharmaceutical-based imaging modalities are particularly problematic for lead validation studies in small animals. In these experimental models, the problem of low spatial resolution is more serious because of the small size of the subject relative to the fixed spatial resolution of the imaging modality. Alternative, relatively time-consuming and labor-intensive non-imaging-based methods have therefore been devised for metabolic measurements in small animals [Green L A et al.: J. Nucl. Med. 39: 729–734 (1998)].

The development and clinical use of anti-cancer chemotherapeutic agents is an exemplary pharmacological application that illustrates the potential utility of a method for inexpensive noninvasive assessment of tissue response in each stage of the process of drug discovery, clinical trials, and therapeutic use. In cancer chemotherapy, compounds are systemically administered to destroy or inhibit the growth of malignant cells in the body. Chemotherapeutic compounds are used to treat both primary malignancies and secondary metastases that may occur at distant sites in the body.

In the typical drug discovery process, initial lead validation in vivo of new potential chemotherapeutic compounds is now generally performed by means of manual anatomical measurements of implanted tumors in animals. Tumors or tumor cell suspensions are implanted or injected into the flanks of test animals. The tumors are often obtained from a foreign species, such as humans. After a variable period of growth, the size of the implanted tumor is determined. One or a combination of potential chemotherapeutic agents is then administered in a selected dosage protocol and serial measurements of changes in tumor size are performed over time. Tumor volume is estimated using two-dimensional measurements of tumor size which are manually obtained with calipers or a ruler. Shrinkage of the tumor is considered to reflect therapeutic efficacy of the test compound. [Geran R I et al.: Cancer Chemother. Res. 3: 51–61 (1972)]. Disadvantages of this method include the limited sensitivity and reproducibility of manual measurements, the difficulty of accurately determining tumor volume from two-dimensional surface measurements, the confounding effects of necrotic and scar tissue on tumor dimensions, and the inability to use tumor models that are typically localized deep within internal organs.

A rapid, noninvasive method for assessment of the response of malignant tissue to potential chemotherapeutic compounds should therefore provide significant advantages over methods currently used for evaluating therapeutic efficacy. Measurement of changes in biochemical pathways specifically associated with malignancy might provide a much more sensitive and rapid indicator of therapeutic efficacy than gross anatomical measurements of tumor size. A noninvasive method might also permit the use of tumor models in which the tumors are localized deep within internal organs. Such a method would also permit serial measurements of changes in tissue biochemistry without the need to kill an animal for histological examination. Measurements of tumor response in an individual animal over a long period of time and during administration of multiple doses of a test compound should enable assessment of secondary effects of the compound, including the likelihood of emergence of drug resistance. Both the initial and long-term therapeutic efficacy of a potential chemotherapeutic agent might thereby be evaluated in each individual animal.

Noninvasive assessment of tissue response to chemotherapeutic agents may also prove valuable in the clinical practice of oncological therapy. In a typical clinical setting, a course of chemotherapy may be administered for many weeks and often costs tens of thousands of dollars. The most common type of chemotherapy is known as adjuvant therapy, and is administered after the bulk of a malignant tumor has been removed by surgery. Starting at some time after the surgical procedure, one or a combination of chemotherapeutic agents is administered to the patient at regularly spaced intervals over a period of weeks or months.

Currently, the outcome of cancer chemotherapy varies widely in different tumor types and is unpredictable for any individual patient. Results of the therapy may vary from complete destruction of the tumor to its continued growth at an unchanged or accelerated rate. The response of any particular tumor to one or a combination of chemotherapeutic agents depends on many biological factors. These factors include the site of the tumor, the stage of tumor development at which therapy has been initiated, the genetic makeup of the tumor cells, and the degree to which the tumor is supplied by local blood vessels, or vascularized. Other, as yet unknown, variables probably also contribute to the widely differing responses of tumors to chemotherapy and the resulting outcome of treatment in individual patients.

In addition, the administration of chemotherapy is frequently accompanied by significant side effects to the patient including severe systemic toxicity. The physician must consider the probability of these side effects, and their impact on overall quality of life, when deciding on an appropriate chemotherapeutic regimen for each patient.

It is generally agreed among oncologists that, at present, cancer chemotherapy remains an art rather than an exact science. Selection of the optimal chemotherapeutic agents for treatment of a particular patient is now largely based on the general standards of treatment established in the medical literature, and on the past experience of the oncologist in treating similar tumor types.

Thus, it would be of great value in clinical practice to be able to rapidly and noninvasively assess the response of a malignant tumor in vivo to one or a combination of chemotherapeutic agents in each patient undergoing treatment. It would also be of great value to be able to predict the outcome of treatment based on quantitative measurements of tumor response after initiation of chemotherapy. Prompt feedback provided by early and frequent monitoring after the initiation of therapy would enable the oncologist to ascertain the effectiveness of the selected regimen and to modify it if the disease is not responding appropriately. Using noninvasive assessment of tissue response, the time necessary to determine the efficacy of a particular regimen may also be sharply reduced, lowering the risk that the cancer will have grown or metastasized in the interim.

A major area of application of radiopharmaceutical-based imaging for assessment of tissue response has been in the study of malignant tumors and their treatment. It is well known that almost all types of malignant tumors metabolize glucose at significantly higher rates than normal or benign tissue in the same organ [Hoh C K et al.: Semin. Nuc. Med. 27: 94–106 (1997); Conti P S et al.: Nuc. Med. Biol. 23: 717–735 (1996)]. Studies on changes in the glucose metabolic rate of malignant tissue in response to chemotherapy have been performed using the imaging modality of positron emission tomography (PET). In these studies, $^{18}$F-fluorodeoxyglucose (FDG), a positron-emitting radiopharmaceutical, was used to quantify rates of glucose metabolism. A number of these studies have demonstrated that the elevated rate of glucose metabolism in malignant tissue is reduced when the tissue is treated with chemotherapeutic agents [Wahl R L et al.: J. Clin. Oncol. 11: 2101–2111 (1993); Findlay M et al.: J. Clin. Oncol. 14: 700–708 (1996); Fischman A J: J. Clin. Oncol. 14: 691–696 (1996); Schulte M et al.: J. Nucl. Med. 40: 1637–1643 (1999)]. It has further been suggested in a number of studies that the relative reduction in glucose metabolic rate after treatment with a chemotherapeutic agent is reflective of therapeutic efficacy and may be predictive of the ultimate disease outcome. (Romer W et al.: Blood 91: 4464–4471 (1998); Bender H et al.: Hybridoma 18: 87–91 (1999)].

The validity of measuring changes in glucose metabolic rate to assess the efficacy of chemotherapy agents is supported by the finding that serial FDG measurements of untreated malignant tumors in humans conducted over a 10-day period before the initiation of chemotherapy remain within a narrow range and demonstrate high reproducibility between measurements [Weber W A et al.: J. Nucl. Med. 11:1771–1777 (1999)]. Subsequent changes in glucose metabolic rate as a result of administration of chemotherapeutic agents may thus be accurately quantified.

While PET imaging has demonstrated very high accuracy in the measurement of glucose metabolism in normal and malignant tissue, it suffers from disadvantages that diminish its utility for routine monitoring of chemotherapy. PET imaging devices are generally located only in large medical centers, and are therefore not available for widespread use. The procedure requires the synthesis of very short half-life radiopharmaceuticals. PET scans are very expensive, costing approximately $2500 per scan. In addition, the spatial resolution of PET is relatively low, and there is a consequent decrease in accuracy in imaging of tumors and metastases that are smaller than approximately 1 cm.

Similarly, SPECT imaging procedures are relatively expensive, and require the use of radiopharmaceuticals and a gamma camera. The spatial resolution of SPECT is also low, and the imaging technique is therefore inaccurate in imaging small tissue structures.

Thus, a need exists for an imaging modality capable of accurately evaluating the response of malignant tumors to chemotherapy in routine clinical application. The imaging modality may desirably be inexpensive and widely available, and provide the high spatial resolution necessary for imaging of small tumors and metastases. Such a method would be valuable in all phases of anti-cancer drug discovery, development, and clinical application.

Similarly, noninvasive assessment of tissue response to compounds in vivo may be useful in the discovery, development, and clinical application of a wide variety of other pharmaceutical compounds.

It is thus evident that there is a widespread need for improved assessment of tissue response to compounds, particularly therapeutic compounds, in live organisms. An ideal method may desirably be rapid, noninvasive, and inexpensive. The method may also allow the simultaneous evaluation of tissue anatomy and functional activity. A method with these advantages should improve the validation of lead compounds in vivo in the drug discovery process; provide valuable data in clinical trials on the efficacy of therapeutic compounds in patients; and provide rapid feedback regarding the response of individual patients to therapeutic compounds administered in clinical treatment. A method providing these advantages should satisfy important needs in all aspects of drug discovery, development, and clinical application.

SUMMARY OF THE INVENTION

The present invention is a radiographic system and method for assessing the response of tissue in a live organism to a compound. The invention provides radiographic images of the accumulation in tissue of a radio-opaque imaging agent that, in one embodiment, binds to a selected cellular target. Changes in the accumulation of the imaging agent in tissue after administration of a compound may be noninvasively monitored over time. Because the imaging procedure can repeatedly be performed on a live organism without detrimental effects, serial measurements may be performed to measure changes in tissue response to a compound over an extended period of time.

Because of these improvements and advantages, the present invention may be particularly useful for assessing the response of abnormal tissue, which is present in a disease process, to a potential therapeutic compound. The invention may thereby be used to evaluate the efficacy of lead compounds administered to animals in early stages of the drug discovery process. It may also be used to assess the response of tissue to compounds administered to patients during clinical trials. The invention may also be used to assess the efficacy of therapeutic compounds in individual patients undergoing clinical treatment. In this application, it may be used to rapidly and noninvasively provide feedback on the efficacy of a particular therapeutic regimen being administered to a patient. The physician may use this feedback on efficacy to modify the dosage or frequency of treatment, or entirely replace the therapeutic compound being used. The system and method may also be used to assess the response of tissue to compounds in a broad range of other in vivo studies, such as those involving the distribution and toxicology of compounds.

In one general form, the present invention is a method for assessing the response of tissue to a compound comprising:
 (a) administering a compound to a live organism;
 (b) administering a radio-opaque imaging agent that binds to a cellular target in the organism;
 (c) generating an X-ray beam;
 (d) illuminating the tissue with the X-ray beam; and
 (e) acquiring a radiographic image of the tissue during illumination.

In another embodiment, a method includes:
 (a) generating two or more X-ray beams with predetermined different energy spectra;
 (b) illuminating the tissue with each of the X-ray beams;
 (c) acquiring a radiographic image of the tissue during illumination by each of the beams; and
 (d) performing a weighted combination of the acquired radiographic images to produce a single image.

The X-ray beams used in this embodiment may be quasi-monoenergetic or monoenergetic.

In one embodiment, the method further includes displaying variable proportions of radiographic density contributed by the imaging agent, by soft tissue, and by bone to the displayed image.

In one embodiment of the method, a selected interval is allowed for the administered compound to interact with tissue. The compound may optionally be repeatedly administered. In addition, serial radiographic images of tissue may be acquired at selected intervals.

In one embodiment, two or more of the acquired radiographic images may be compared. One method of comparison includes comparing the radiographic density of corresponding areas of displayed tissue on at least two acquired images.

In one embodiment of the invention, the radio-opaque imaging agent selectively binds, either covalently or noncovalently, to a cellular target within the organism. The cellular target may be a cellular structure, such as an organelle, an area of the cell, such as the cytoplasm, or a cellular molecule. The cellular molecule may be an enzyme, a non-enzyme protein, a coenzyme, a nucleic acid, or a lipid. In one embodiment of the invention, the cellular molecule is hexokinase. In one embodiment of the method, the cellular molecule is coenzyme A. In one embodiment of the invention, the radio-opaque imaging agent is bidirectionally cell membrane-permeable. In one embodiment, the imaging agent is cell membrane-permeable through passive diffusion.

In some embodiments of the invention, the imaging agent accumulates in abnormal tissue at a different rate or concentration than in normal tissue. In some embodiments, the imaging agent accumulates in malignant tissue at a different rate or concentration than in non-malignant tissue. In other embodiments, the imaging agent accumulates in abnormal myocardial tissue at a different rate or concentration than in normal myocardial tissue.

The administered compound may be chosen from potential or known therapeutic compounds, or other categories of compounds.

One embodiment of the invention is a method for radiographic assessment of tissue response to a compound (e.g. a method of measuring the therapeutic efficacy of a compound) wherein the method comprises:

(a) administering to a live organism a radio-opaque imaging agent that binds to a cellular target or is passively cell membrane-permeable;

(b) acquiring a first radiographic image of tissue in the organism;

(c) administering a compound to the organism after acquiring the first radiographic image;

(d) allowing an interval to elapse;

(e) acquiring a second radiographic image of tissue in the organism after administering the compound; and (f) comparing the radiographic density of tissue displayed on the first and second radiographic images to assess the tissue response to the compound.

One embodiment further includes classifying the therapeutic efficacy of a compound based on the difference in radiographic density of tissue displayed on the first and second radiographic images.

In some embodiments of the invention, the imaging agent may accumulate in tissue in proportion to the glucose metabolic rate of the tissue. Changes in the glucose metabolic rate of tissue after administration of a compound, such as a therapeutic compound, may thereby be assessed. In some embodiments of the invention, the imaging agent accumulates in tissue in proportion to the rate of fatty acid metabolism of the tissue. Changes in the rate of fatty acid metabolism of tissue, particularly cardiac tissue, after administration of a compound, such as a therapeutic compound, may thereby be quantified.

The invention, according to one embodiment, is based on the well-established principle that the glucose metabolic rate of most types of malignant tumors is elevated compared with normal tissue in the same body organ. It has also been established that malignant tissue contains elevated levels of a number of the enzymes active in glucose metabolism.

Hexokinase is an enzyme which is particularly overexpressed in malignant cells. Hexokinase catalyzes the first step in glucose metabolism, which is the phosphorylation of glucose to glucose-6-phosphate. Quantitative studies have consistently demonstrated elevated levels of hexokinase in malignant tissue, with the increased enzyme level approximately proportional to the increased tissue glucose metabolic rate. Hexokinase is therefore an appropriate target enzyme for monitoring the glucose metabolic rate of malignant tissue.

Accordingly, one embodiment of the present invention utilizes a radiographic imaging agent that comprises a cell membrane-permeable, radio-opaque, high-affinity ligand for intracellular hexokinase. In this embodiment, a hexokinase substrate or inhibitor is linked to a non-radioactive, radio-opacifying moiety in a manner that facilitates efficient passage of the imaging agent across the outer cell membrane (plasma membrane), direct entry into the cytosol, and selective binding with high affinity to the substrate binding site of intracellular hexokinase molecules. The cell membrane-permeable property of the imaging agent molecules insures their direct entry into the cytosol, and the exit of unbound imaging agent molecules across the cell membrane. Thus, imaging agent molecules that have bound to hexokinase are retained within the cell for at least a few hours. Unbound imaging agent molecules exit the cell at a relatively rapid rate, decreasing background radio-opacity and increasing contrast in the radiographic image. Because of the much higher concentration of hexokinase in malignant cells relative to benign and normal cells, the imaging agent accumulates in malignant tissue at an elevated level relative to benign and normal tissue.

In an example of a system and method according to the invention, radiographic images using a radio-opaque imaging agent may be acquired before and after administration of a compound, and the images then compared.

A first radiographic procedure is initiated by administering the imaging agent to a live organism. After the imaging agent accumulates throughout body tissue during a time interval, the organism is appropriately positioned in relation to the X-ray source and image receptor, and radiographic images are acquired. Tissue that metabolizes glucose at a high rate, such as malignant tissue, will have accumulated higher intracellular levels of the imaging agent than tissue that metabolizes glucose at a lower rate, such as normal tissue. Because the imaging agent is radio-opaque, its differential accumulation causes corresponding differences in the absorption of the illuminating X-ray beam, which are manifested as differing levels of radiographic density on the radiograph.

A compound is then administered to the organism. A time interval may optionally be allowed to elapse to permit the compound to interact with tissue within the organism. A second radiographic imaging procedure is then performed. The radiographic density of corresponding areas of tissue displayed on the first and second images may then be compared.

In one embodiment of the invention, radiographic density contributed by the accumulated imaging agent is isolated from radiographic density contributed by soft tissue and bone. In this embodiment, the tissue being examined is sequentially transilluminated by X-ray beams with predetermined different mean energy spectra, and a separate radiographic image is acquired during transillumination by each beam. Using a predetermined weighting coefficient for each image, the image processing system performs a weighted combination of the acquired images to produce a single displayed image. The use of transilluminating X-ray beams with appropriate mean energy spectra together with appropriate weighting coefficients in the image processing procedure enables the cancellation on the displayed image of radiographic density contributed by soft tissue and bone. The remaining radiographic density present on the displayed image is contributed solely by differential intracellular accumulation of the radio-opaque imaging agent in malignant and normal tissue. Although this image of accumulated imaging agent is a functional image of tissue physiology, it is displayed with the high spatial resolution of a radiographic image, which may provide an anatomical image.

The system and method may also be used to generate radiographic images of tissue that combine both functional (biochemical) and anatomical (structural) information on a single image, with the two types of data in complete spatial registration. The viewer may interactively vary the proportion of radiographic density contributed to the displayed image by accumulated imaging agent, by soft tissue, and by bone. A functional image of tissue combined with a variable degree of a superimposed anatomical image in registration may thereby be displayed. The effects of a compound on both tissue biochemistry and anatomy may thereby be simultaneously assessed. The combination of functional and anatomical information on a single image, or, if desired, on a series of images, facilitates the precise localization of the accumulation of imaging agent in relation to nearby anatomical landmarks.

When used in the drug discovery process, the system and method may be used to quantify the response of tissue in an individual animal to one or more compounds administered over time. The variability between test animals in studies of efficacy and toxicity may thereby be significantly reduced. The invention may also reduce the need to perform labor-intensive and expensive gross anatomical studies of organs and histological examination of tissue.

An example of the utility of the present invention in the discovery, development, and clinical application of pharmacological compounds is in the field of cancer chemotherapy. A number of studies have suggested that measurement of changes in the glucose metabolic rate of malignant tissue after administration of chemotherapeutic agents can be used as reliable indicators of therapeutic efficacy [Bender H et al., Hybridoma 18: 87–91 (1999); Dehdashti F et al.: Eur. J. Nucl. Med. 26: 51–56 (1999); Price P, Jones T, Eur J Cancer 31A: 1924–1927 (1995)].

The present invention may be used to localize malignant tissue in vivo based on its elevated glucose metabolic rate, and to compare the glucose metabolic rate of malignant tissue before and after administration of an anti-cancer chemotherapeutic agent. The ability to obtain rapid and ongoing feedback on the response of malignant tissue to chemotherapeutic agents may be of significant clinical utility. Chemotherapy regimens that do not demonstrate therapeutic efficacy in a patient may be modified or halted, and a different regimen initiated. The time required to evaluate the efficacy of a particular therapeutic regimen may be significantly reduced, which may lower the risk of metastasis in the interim.

The present system and method may also be used to evaluate the efficacy of therapeutic compounds used in cardiac disease. The rates of glucose and fatty acid metabolism are often lowered in diseased cardiac tissue. The present invention may be used to localize diseased or damaged cardiac tissue in vivo based on its abnormally low glucose metabolic rate, and to compare the glucose metabolic rate of cardiac tissue before and after administration of cardiac therapeutic agents. Cardiac function may thereby be evaluated over time after initiation of a course of therapy, and the treatment regimen modified based on the results.

It will be apparent to one skilled in the art that the present invention may also be used to evaluate the response of tissue to a wide variety of compounds in studies unrelated to therapeutic efficacy. For example, the invention may be used in the assessment of toxicity of compounds. A decrease in the local tissue concentration of a particular cellular target in a body organ might be used as an indicator of compound toxicity.

The invention may be used for imaging tissue in particular body organs such as the breast, lungs, liver and colon, in single or multiple images, and for imaging large areas of the body or the whole body in single or multiple images. In addition, it will be apparent to one skilled in the art that with the appropriate modifications to the imaging method and imaging agents, the present invention may be used in computed tomography and other radiographic modalities.

The present invention is thus capable of noninvasively generating images for assessing the response of tissue to a compound, while providing the high degree of anatomical detail and spatial resolution characteristic of radiographic imaging.

BRIEF DESCRIPTION OF THE DRAWINGS

FIGS. 3A and 3B show sectional and plan views respectively of the X-ray filter apparatus and its relationship to the X-ray source.

FIG. 12 is a flow chart of a method for assessment of tissue response to a compound being used in clinical therapy.

DETAILED DESCRIPTION OF THE EMBODIMENTS

A. Radio-Opaque Imaging Agents

Figure 1:
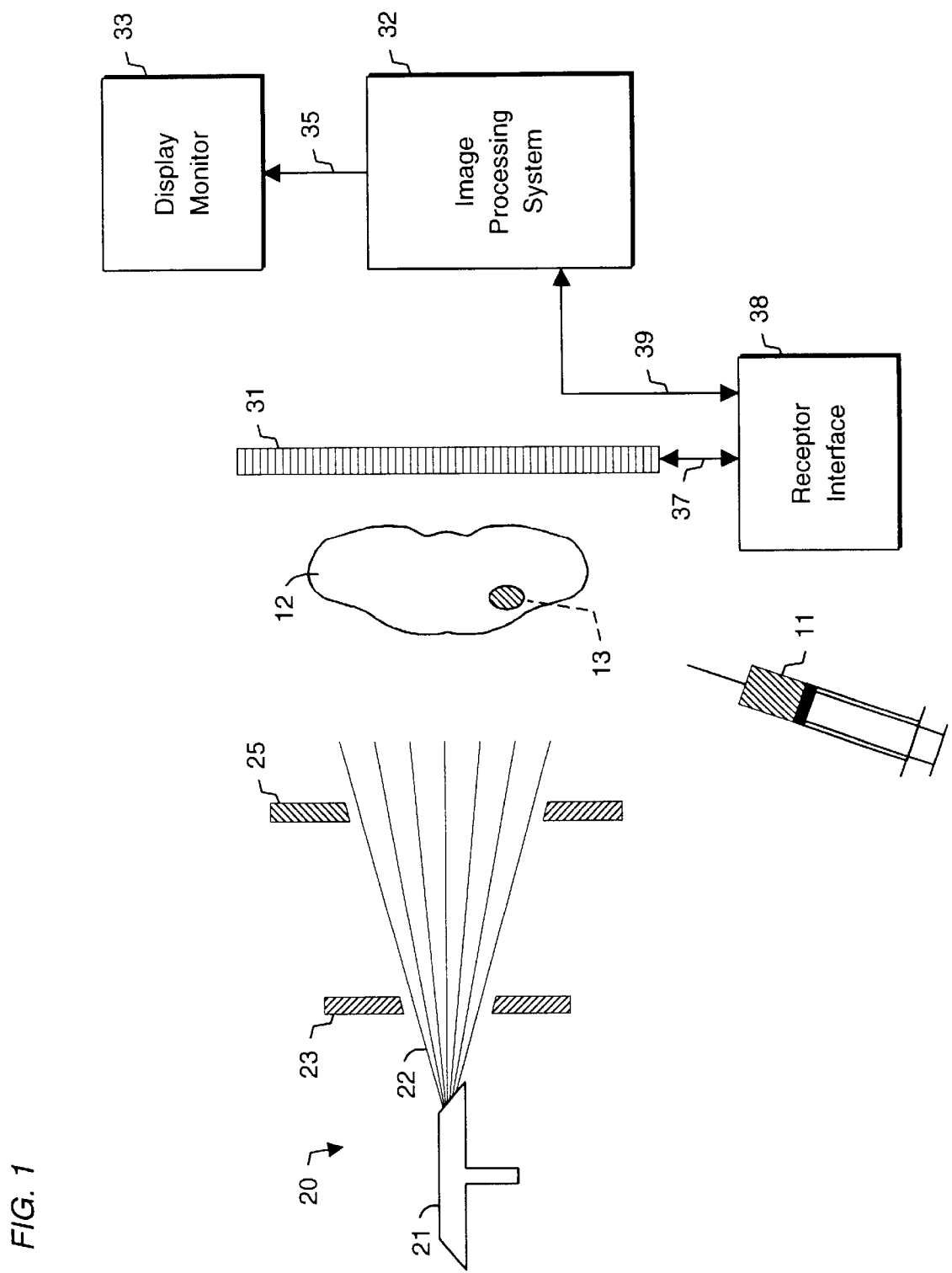
FIG. 1 is a block diagram of an embodiment of the imaging system using a single polyenergetic X-ray transilluminating beam.

A radio-opaque imaging agent for assessment of tissue response to a compound should accumulate in tissue in approximate proportion to the concentration of a selected cellular target in the tissue. In the embodiments of the present invention, a radio-opaque imaging agent selectively binds to a selected cellular target whose concentration may vary in response to administration of a compound. Measurements of changes in the concentration or tissue distribution of a cellular target after one or more administrations of a compound may aid in the assessment of the effects of the compound on tissue biochemical pathways.

1. Imaging of Enzymes

One of the most prominent and characteristic abnormalities of malignant tissue is its elevated rate of glucose metabolism relative to normal tissue. It has long been known that this elevated metabolic rate is accompanied by a corresponding increase in the intracellular concentration and activity of the enzymes active in glucose metabolism.

In particular, studies have repeatedly demonstrated that the considerable elevation of glucose metabolic rate in malignant tissue is accompanied by elevated levels of hexokinase activity. Hexokinase catalyzes the first step in glucose metabolism, which is the phosphorylation of glucose to glucose-6-phosphate. Malignant cells markedly overexpress hexokinase relative to benign and normal cells from the same organ [Weber G: Gann Monogr. Cancer Res. 13: 47–77 (1972); Weinhouse S: Cancer Res. 32: 2007–2016]. A portion of intracellular hexokinase is located in the cytosol in soluble form, and another portion is located in the cytosol and attached to the outer mitochondrial membrane [Arora K K, Pedersen P L: J. Biol. Chem. 263: 17422–17428 (1988)]. The hexokinase activity of normal, benign and malignant tissue is roughly proportional to their respective rates of glucose metabolism. Kinetic analysis of the k compartments in PET glucose imaging studies indicates that the increase in glucose metabolic rate in malignant tissue can largely be accounted for by increased activity of hexokinase in the $k_3$ (phosphorylation) compartment. The detection and quantitation of hexokinase is thus a particularly useful method for identification of malignant tissue.

Accordingly, one embodiment of the radio-opaque functional imaging agent of the present invention is a cell membrane-permeable, high-affinity ligand for intracellular hexokinase. In this embodiment, a hexokinase substrate or inhibitor is linked to a non-radioactive, radio-opaque moiety in a manner that permits efficient diffusion of the imaging agent across the cell membrane into the cytosol and attachment with high affinity to the substrate binding site of intracellular hexokinase molecules. In one embodiment, the molecule may comprise an amino sugar, in pyranose or furanose form, attached by means of a covalent linkage arm to a moiety containing one or more atoms of a radio-opaque element, which may be iodine.

The protein structures of yeast and human hexokinases have been determined using both X-ray crystallography and the known amino acid sequences of the enzymes [Willson M et al.: J Enz Inhib. 12: 101–121 (1997); St. Charles R et al.: Diabetes 43: 784–791 (1994); Aleshin A E et al.: Structure 6:39–50 (1998)], and the relative activity of many of their substrates and inhibitors has been experimentally determined [Sols A, Crane R K: J. Biol. Chem. 210: 581–595 (1954); Maley F, Lardy H A: J Biol Chem. 214: 765–773 (1955); Coats EA et al.: J Enz Inhib. 6: 271–282 (1993)]. These published results, in combination with original molecular modeling studies, provide data necessary for the design of cell-permeable, radio-opaque, high affinity ligands for hexokinase described in the present invention.

The structural interactions of hexokinase with its substrates and inhibitors have been well characterized. Both pyranose and furanose ring structures can bind to the substrate binding site of the enzyme with high affinity. Based on published data and the present modeling studies, the optimal strategy for attachment of moieties to the sugar resulting in the least steric hindrance of the substrate binding site of the enzyme is substitution of the hydroxy group at the C-2 position of the pyranose or furanose ring. In addition, these studies suggest that a linkage arm of appropriate design inserted between the enzyme binding moiety and the radio-opacifying moiety can significantly improve the affinity of the imaging agent for hexokinase. The improvement in affinity for the enzyme is provided by two functions of the linkage arm. One function is to minimize steric hindrance of the substrate binding site by the radio-opaque moiety of the imaging agent. The second function is to enhance binding of the imaging agent molecule to the enzyme through hydrogen bonds and van der Waals contacts with amino acid residues in the vicinity of the binding site.

In the present studies, conformational searches and QSAR analysis were used to determine optimal characteristics of the linkage arm and to identify energetically feasible conformers. The most important characteristics of the linkage arm were found to be its length, its bulk, and its interaction with amino acid residues in the vicinity of the substrate binding cavity of the enzyme. It has been determined that to avoid unwanted steric interactions between the radio-opaque moiety and the binding site of the enzyme, the length of the linkage arm separating the pyranose or furanose ring from the radio-opaque moiety, as measured from the C-2 atom of the ring to the proximal atom of the radio-opaque moiety, should be a minimum of approximately 8 Å. Shorter linkage arm lengths may allow unwanted interactions between the radio-opaque moiety and residues local to the substrate binding site. Significantly longer linkage arm lengths may produce unwanted nonspecific interactions with other intracellular components, although longer lengths may be used with the present invention.

In addition, the linkage arm may be substituted to further improve the binding affinity of the imaging agent for the enzyme. A particularly effective linkage arm comprises an aryl moiety with at least one polar substituent, such as a nitro or amino group, in ortho or meta positions. However, substituent characteristics should be carefully controlled. For example, substituent bulk above a certain size may result in steric hindrance and a sharp decrease in binding affinity.

In addition to the requirement of high affinity for hexokinase, the imaging agent of one embodiment should readily permeate the cell membrane and enter the cytosol in order to bind intracellular enzyme molecules. Further, imaging agent molecules which have not attached to enzyme molecules should efficiently exit the cell to effectively reduce background radio-opacity. Glucose is normally transported bidirectionally across the cell membrane by means of one or more of the GLUT transport proteins. Substituents in, or moieties linked to, the basic pyranose or furanose ring can inhibit transport by these proteins. Design of the imaging agent so that it is lipophilic insures its efficient bidirectional diffusion across the cell membrane, without the necessity for facilitated transport by the GLUT proteins.

In these studies, lipophilicity of imaging agents was characterized by computed logP. Lipophilicity is defined as the partitioning of a compound between an aqueous and a nonaqueous phase, with the nonaqueous phase usually chosen to be n-octanol. LogP is the log of the partition coefficient of a compound between the two phases, and is a standard measure of lipophilicity in biological systems. For a wide range of small non-ionic molecules, strong correlations have been experimentally verified between logP and the distribution of the molecule between the aqueous medium and the cell membrane [Hansch et al.: J. Pharm Sci. 61: 1–19 (1972)]. Using appropriate models, computed values of logP can correlate closely with measured values [Ghose A K et al.: J. Comp. Chem. 9: 80–90 (1988); Rekker R F, Mannhold R: Calculation of Drug Lipophilicity, VCH, Weinheim, (1992); Meylan W M, Howard P H: J. Pharm. Sci. 84: 83–92 (1995)].

A number of these computational models allow determination of the logP values of individual moieties or fragments that comprise a molecule as well as the global, or overall, logP value of the entire molecule. Computation of the logP values of individual fragments or moieties allows the identification of localized hydrophobic and hydrophilic regions of a molecule and may provide useful predictive data regarding the interaction of these regions with other molecules and their contribution to predicted and observed biological activity.

Commonly used radiographic contrast agents generally have molecular weights of below 1000 daltons. For molecules of this size, the logP value should be above 0.0 and should preferably be in the range of approximately 0.0 to approximately 6.0 to enable optimal passive diffusion across the cell membrane. Table 1 shows experimental logP values and molecular weights of some commonly used non-ionic radiographic contrast agents [Hansch et al: Exploring QSAR, Amer. Chem Soc., Washington D.C. (1995)]. The table also shows computed logP values and molecular weights of glucose and of representative iodo-substituted hexose imaging agents disclosed by Ledley and Gersten (U.S. Pat. No. 4,716,225). The computed logP values and molecular weights of Examples 1–3 of the present invention are also shown.

TABLE 1

| Compound | logP | MW | U.S. Pat. No. |
|---|---|---|---|
| Iohexol | −3.05 | 821.14 | 4,250,113 |
| Iopromide | −2.05 | 791.12 | 4,364,921 |
| Metrizamide | −1.86 | 789.10 | 3,701,771 |
| Glucose | −2.89 | 180.16 | — |
| 6-Iodo-galactose | −1.73 | 290.06 | 4,716,225 |
| 2-Iodo-galactose | −2.08 | 290.06 | 4,716,225 |
| Example 1 | +3.28 | 866.19 | present |
| Example 2 | +3.77 | 894.24 | present |
| Example 3 | +2.56 | 1014.35 | present |

The molecular weights of the compounds in Table 1 range between 180.16 to 1014.35 daltons. The logP values of the first three contrast agents are below 0.0, and are consistent with their demonstrated hydrophilicity and inability to permeate cell membranes. The logP values of all iodo-substituted hexose compounds disclosed by Ledley and Gersten, two representative examples of which are listed in Table 1, are also below 0.0. In contrast, Examples 1–3 of the present invention have logP values above 0.0, and their relatively high lipophilicity enhances their passive diffusion across the cell membrane and entry into the cytosol.

The radio-opaque moiety of the imaging agent is substituted with one or more atoms of an element, which may be iodine, and which exhibits suitable radio-opacity in the photon energy spectrum emitted by a typical diagnostic X-ray source operated at approximately 50 keV to approximately 80 keV. Although iodine is the most common radio-opaque element used for enhancement of radiographic contrast, other selected elements may be used in the radio-opaque moiety in alternate embodiments of the imaging agent. The suitability of an element for use in the radio-opaque moiety will depend on the photon energy of the element's K-absorption edge, a property explained in detail in section E. It will also be appreciated that X-ray sources of lower or higher energy may also be used with the invention. Radio-opaque elements with higher K-absorption edges may generally be used with X-ray beams of higher photon energy, and elements with lower K-absorption edges may generally be used with X-ray beams of lower photon energy.

One or more functional groups may additionally be substituted in proximity to one or more radio-opaque substituent atoms on the radio-opaque moiety. Polar and hydroxyalkyl functional groups generally increase the water solubility of the imaging agent molecule. These groups may also create localized hydrophilic regions that essentially mask the hydrophobicity of the radio-opaque atoms. Masking by hydrophilic moieties may reduce nonspecific binding interactions between the radio-opaque atoms and host proteins in vivo. Reduction of nonspecific binding to proteins can minimize the occurrence of adverse reactions to imaging agents that may be related to chemotoxicity [Sovak M: Invest Radiol. 29 (Suppl 1): S4–14 (1994); Bennani et al.: U.S. Pat. No. 5,609,851; Schaefer et al.: U.S. Pat. No. 5,043,152]. In the present invention, the logP value of each of the hydrophilic moieties which may be substituted in the radio-opaque moiety of the imaging agent is below about 0.0.

The general form of one embodiment of an imaging agent of the present invention is:

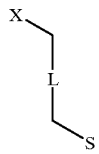

wherein:

the S moiety is a pyranose or a furanose;

the X moiety is an aryl substituted with at least one atom having a K-absorption edge of about 13 keV to about 90 keV;

the L moiety is bonded to the S moiety and to the X moiety; and the global logP value of the molecule is greater than about 0.0. In one embodiment the global logP value is greater than about 1.0.

In one embodiment the X moiety is further substituted with at least one moiety having a logP value of less than about 0.0. In one embodiment the X moiety is further substituted with at least one moiety having a logP value of less than about 1.0.

In certain embodiments the imaging agent is bidirectionally cell membrane-permeable. In certain embodiments the imaging agent is capable of binding to a cellular target. In certain embodiments the imaging agent is capable of binding to the substrate binding site of an enzyme. In one embodiment the enzyme is hexokinase.

The general form of one embodiment of an imaging agent of the present invention is:

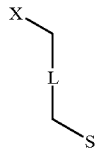

wherein:

the S moiety is a pyranose or a furanose;

the X moiety is selected from alkyl, alkoxy, alkylthio, alkenyl, alkylamino and aryl, and is substituted with at least one atom having a K-absorption edge of about 13 keV to about 90 keV;

the L moiety is selected from aryl, arylamido, alkylamido, alkyl, and thioamido, and is bonded to the X moiety and to the S moiety.

In some embodiments the X moiety is substituted with at least one atom of Br, I, or Bi. In some embodiments the X moiety is further substituted with one or more groups which may be, independently, hydroxyalkyl, alkoxy, alkloxyalkyl, alkylamido, hydroxyalkylamido, and polyhydroxyalkylamido. These groups may in turn be further substituted.

In certain embodiments of the present invention the L moiety is an unsubstituted or substituted amidoaryl and is N-bonded to the S moiety. The L moiety may be further substituted with one or more nitro, amino, methyl, methoxy, or hydroxy groups.

In certain embodiments the S moiety may be hydroxy-substituted. In certain embodiments the S moiety may be 2-hydroxy-substituted.

In one embodiment, the composition is 2-Amino4-[3',5'-bis(N-acetamido)-2',4',6'-triiodophenyl]-benzoyl-D-glucosamine. In one embodiment, the composition is 2,6-Diamino-4-[3',5'-bis(N-methylacetamido)-2',4',6'-triiodophenyl]-benzoyl-D-glucosamine. In one embodiment, the composition is 2-Amino-4-[3'5'-bis(2,3-dihydroxypropylmethylcarbamoyl)-2',4',6'-triiodophenyl]-benzoyl-D-glucosamine.

In some embodiments of the invention, the X moiety is substituted with at least one atom of a radioactive isotope. In one embodiment the X moiety is substituted with at least one atom of $^{123}$I.

In one embodiment, the S moiety is a pyranose or furanose that attaches to the binding site of an intracellular enzyme; the X moiety is radio-opaque in the portion of the photon energy spectrum typically used in radiographic imaging; and the L moiety is bonded to the S moiety and to the X moiety.

In one embodiment, the logP value of the imaging agent molecule is above 0.0 to enable passive diffusion of the molecule across the cell membrane, and the logP value of at least one region of the molecule is below about 0.0. In one embodiment, the S moiety is a pyranose or furanose that attaches to the binding site of an intracellular enzyme; the X moiety is radio-opaque in the portion of the energy spectrum typically used in diagnostic radiographic imaging; and the L moiety is bonded to the S moiety and to the X moiety.

It will be understood that the use of the above terms in the case of residues that can be substituted or unsubstituted will include the reasonably substituted forms of such residues as well as their unsubstituted forms. Reasonable substitutions which will produce useful compounds will be evident to one skilled in the art and will include such substituents, without limitation, as amino, nitro, hydroxy, methoxy, and acetyl groups, among others.

Methods of syntheses for Examples 1–3 employ reactions commonly used in synthetic chemistry and will be well known to those of ordinary skill in the art.

EXAMPLE 1

2-Amino-4-[3',5'-bis(N-acetamido)-2',4',6'-triiodophenyl]-benzoyl-D-glucosamine (12)

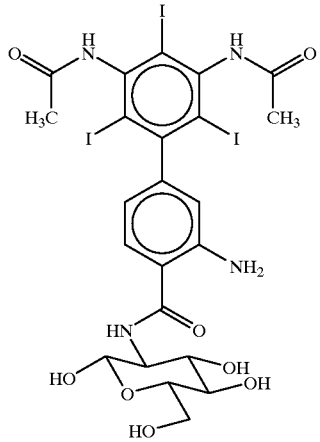

(12)

The nitro groups of 2-chloro-1,3,5-trinitrobenzene (1) are reduced by reaction with tin and hydrochloric acid to yield 2-chloro-1,3,5-triaminobenzene (2).

The amino groups of 2-chloro-1,3,5-triaminobenzene (2) are acetylated by reaction with acetic anhydride to yield 2-chloro-1,3,5-triacetamidobenzene (3).

2-chloro-1,3,5-triacetamidobenzene (3) is nitrated by reaction with a mixture of concentrated sulfuric and nitric acids to yield 2-chloro-1,3,5-triacetamido-3,5-dinitrobenzene (4).

2-chloro-1,3,5-triacetamido-3,5-dinitrobenzene (4) is coupled with 4-iodotoluene by treatment with copper bronze at 200° C. to yield 2',4',6'-triacetamido-3',5'-bis(nitro)-4-methylbiphenyl (5).

2',4',6'-triacetamido-3',5'-bis(nitro)-4-methylbiphenyl (5) is treated with 6N hydrochloric acid to yield 2',4',6'-triamino-3',5'-bis(nitro)-4-methylbiphenyl (6).

The amino groups of 2',4',6'-triamino-3',5'-bis(nitro)-4-methylbiphenyl (6) are converted to diazonium groups by treatment with a mixture of sodium nitrite and hydrochloric acid. The product is iodinated by reaction with potassium iodide to yield 2',4',6'-triiodo-3',5'-bis(nitro)-4-methylbiphenyl (7).

The nitro groups of 2',4',6'-triiodo-3',5'-bis(nitro)-4-methylbiphenyl (7) are reduced to amines by reaction with tin and hydrochloric acid to yield 2',4',6'-triiodo-3',5'-bis(amino)-4-methylbiphenyl (8). The product is used in the preparation of Examples 1, 2, and 3 of the present invention.

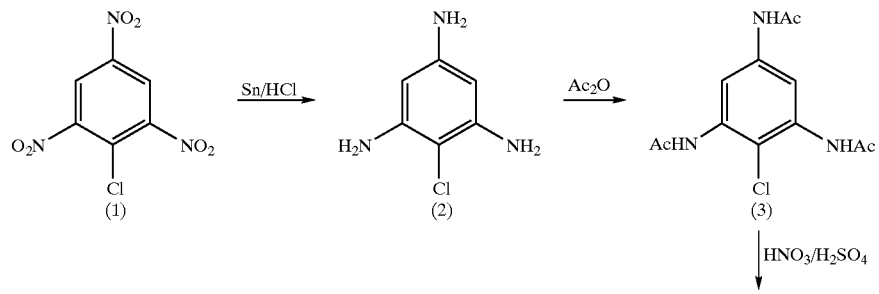

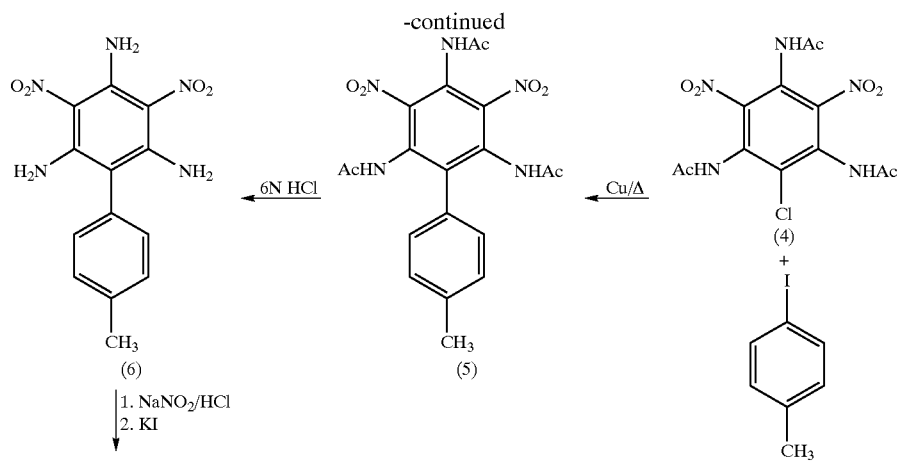

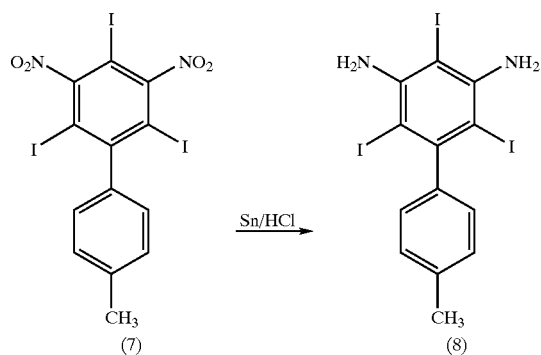

2',4',6'-triiodo-3',5'-bis(amino)-4-methylbiphenyl (8) is nitrated by reaction with concentrated nitric and sulfuric acids. The product is acetylated by acetic anhydride to yield 2',4',6'-triiodo-3',5'-bis(acetamido)-3-nitro-4-methylbiphenyl (9).

The 4-methyl group of 2',4',6'-triiodo-3',5'-bis(acetamido)-3-nitro-4-methylbiphenyl (9) is oxidized by potassium permanganate to yield 2',4',6'-triiodo-3',5'-bis(acetamido)-3-nitrobiphenyl-4-carboxylic acid (10).

2',4',6'-triiodo-3',5'-bis(acetamido)-3-nitrobiphenyl-4-carboxylic acid (10) is coupled with 1,3,4,6-tetra-O-acetyl-D-glucosamine in the presence of 1-[3-(dimethylamino)propyl]-3-ethylcarbodiimide hydrochloride and N-hydrosuccinamide to yield 2-nitro-4-[3',5'-bis(N-acetamido)-2',4',6'-triiodophenyl]-benzoyl-1,3,4,6-tetra-O-acetyl-D-glucosamine. The protecting acetyl groups on the glucosamine moiety are removed by treatment with sodium carbonate in methanol to yield 2-nitro-4-[3',5'-bis(N-acetamido)-2',4',6'-triiodophenyl]-benzoyl-D-glucosamine (11).

2-nitro-4-[3',5'-bis(N-acetamido)-2',4',6'-triiodophenyl]-benzoyl-D-glucosamine (11) is catalytically reduced by hydrogen in the presence of palladium on charcoal to yield 2-amino-4-[3',5'-bis(N-acetamido)-2',4',6'-triiodophenyl]-benzoyl-D-glucosamine (12).

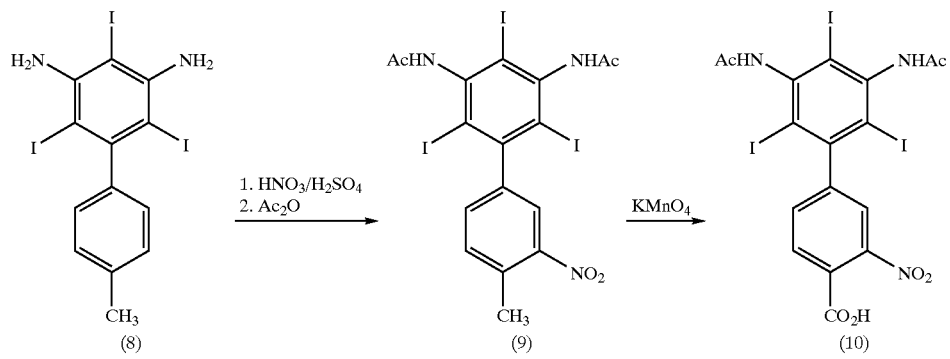

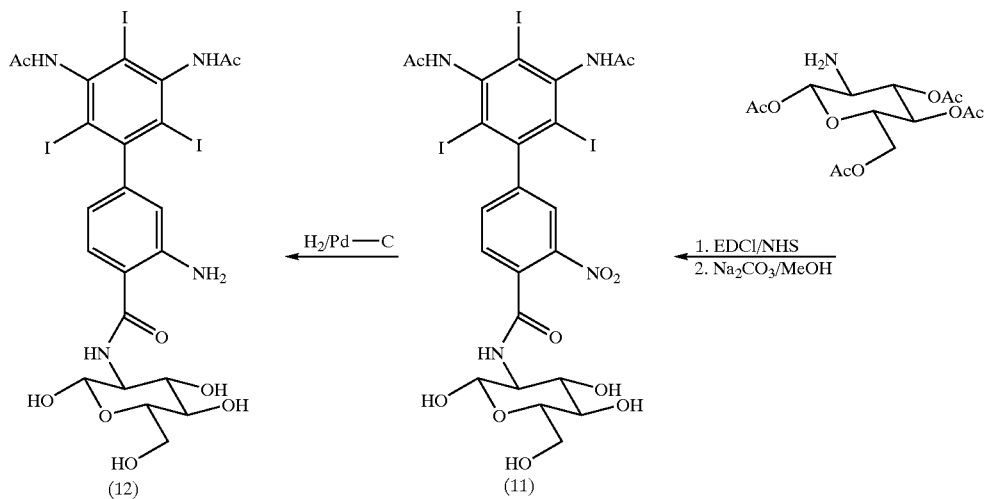

In Example 1,2-Deoxy-D-glucose is 2-hydroxy-substituted with a o-aminobenzamide linkage arm, which links the pyranose to a triiodophenyl moiety. The pyranose ring binds to the substrate binding site of hexokinase. The o-aminobenzamide linkage arm enhances the binding of the pyranose to the binding site, and also positions the radio-opaque triiodophenyl moiety sufficiently distant from the pyranose moiety to prevent steric hindrance of the binding site. The triiodophenyl configuration provides strong carbon-iodine bonds and thereby improves resistance to deiodination in vivo. Substituent acetamido groups improve water solubility and provide hydrophilic shielding of the iodine atoms. Global lipophilicity enhances bidirectional diffusion of the imaging agent molecule across the cell membrane. The computed logP value of Example 1 is 3.28.

EXAMPLE 2

2,6-Diamino4-[3',5'-bis(N-methylacetamido)-2',4',6'-triiodophenyl]-benzoyl-D-glucosamine (16)

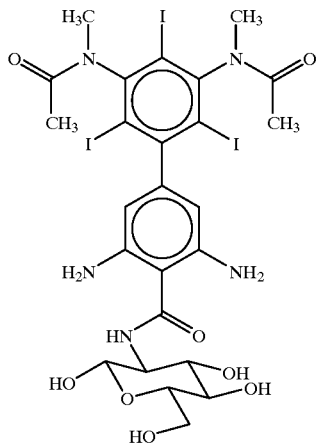

(16)

2',4',6'-triiodo-3',5'-bis(amino)-4-methylbiphenyl (8) is reacted with a mixture of nitric acid and sulfuric acid. Nitration under more vigorous conditions than those of Example 1 result in a product with a higher yield of nitro groups on both the 3- and 5-positions of the lower biphenyl ring. The product is treated with sodium cyanoborohydride and formaldehyde. The resulting product is treated with acetic anhydride to yield 2',4',6'-triiodo-3',5'-bis(N-methylacetamido)-3,5-dinitro-4-methylbiphenyl (13).

The 4-methyl group of 2',4',6'-triiodo-3',5'-bis(N-methylacetamido)-3,5-dinitro-4-methylbiphenyl (13) is oxidized by reaction with potassium permanganate to yield 2',4',6'-triiodo-3',5'-bis(N-methylacetamido)-3,5-dinitrobiphenyl-4-carboxylic acid (14).

2',4',6'-triiodo-3',5'-bis(N-methylacetamido)-3,5-dinitrobiphenyl-4-carboxylic acid (14) is coupled with 1,3,4,6-tetra-O-acetyl-D-glucosamine in the presence of 1-[3-(dimethylamino)propyl]-3-ethylcarbodiimide hydrochloride and N-hydrosuccinamide to yield 2,6-dinitro-4-[3',5'-bis(N-methylacetamido)-2',4',6'-triiodophenyl]-benzoyl-1,3,4,6-tetra-O-acetyl-D-glucosamine. The protecting acetyl groups on the glucosamine moiety are removed by treatment with sodium carbonate in methanol to yield 2,6-dinitro-4-[3',5'-bis(N-methylacetamido)-2',4',6'-triiodophenyl]-benzoyl-D-glucosamine (15).

2,6-dinitro-4-[3',5'-bis(N-methylacetamido)-2',4',6'-triiodophenyl]-benzoyl-D-glucosamine (15) is catalytically reduced by hydrogen in the presence of palladium on charcoal to yield 2,6-diamino-4-[3',5'-bis(N-methylacetamido)-2',4',6'-triiodophenyl]-benzoyl-D-glucosamine (16).

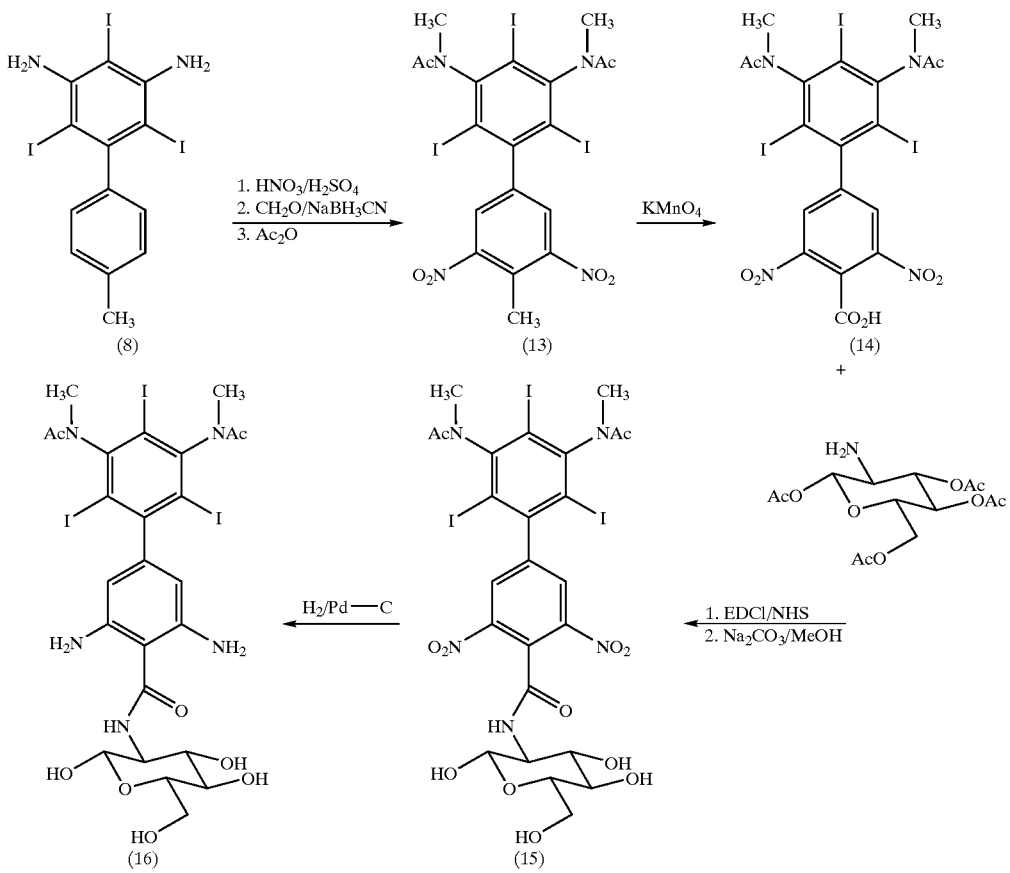

In Example 2, N-methylacetamido groups on the 3' and 5' positions of the triiodophenyl moiety improve water solubility of the molecule and provide hydrophilic shielding of the iodine atoms. The computed logP value of Example 2 is 3.77.

EXAMPLE 3
2-Amino-4-[3',5'-bis(2,3-dihydroxypropylmethylcarbamoyl)-2',4',6'-triiodophenyl]-benzoyl-D-glucosamine (20)

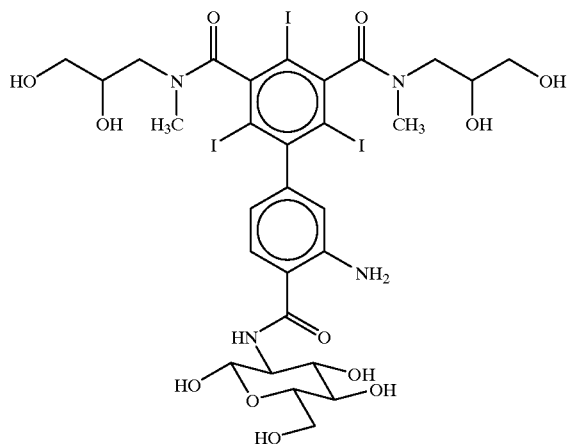

2',4',6'-triiodo-3',5'-bis(amino)-4-methylbiphenyl (8) is reacted with a mixture of nitric acid and sulfuric acid. The product is treated with copper cyanide and sodium nitrite to yield 2',4',6'-triiodo-3',5'-bis(cyano)-3-nitro-4methylbiphenyl (17).

2',4',6'-triiodo-3',5'-bis(cyano)-3-nitro-4-methylbiphenyl (17) is treated with sodium hydroxide. The product is treated with hydrochloric acid and methanol. The 4-methyl group of the product is oxidized by potassium permanganate to yield 2',4',6'-triiodo-3',5'-bis(carboxymethyl)-3-nitrobiphenyl-4-carboxylic acid (18).

2',4',6'-triiodo-3',5'-bis(carboxymethyl)-3-nitrobiphenyl-4-carboxylic acid (18) is coupled with 1,3,4,6-tetra-O-acetyl-D-glucosamine in the presence of 1-[3-(dimethylamino)propyl]-3-ethylcarbodiimide hydrochloride and N-hydrosuccinamide to yield 2-nitro-4-[3',5'-bis(carboxy)-2',4',6'-triiodophenyl]-benzoyl-1,3,4,6-tetra-O-acetyl-D-glucosamine. The protecting acetyl groups on the glucosamine moiety are removed by reaction with sodium hydroxide in methanol to yield 2-nitro-4-[3',5'-bis(carboxy)-2',4',6'-triiodophenyl]-benzoyl-D-glucosamine (19).

2-nitro-4-[3',5'-bis(carboxy)-2',4',6'-triiodophenyl]-benzoyl-D-glucosamine (19) is treated with N-methyl-2,3-dihydroxypropylamine and 2-(1H-benzotriazol-1-yl)-1,1,3,3-tetramethyluronium tetrafluoroborate. The product is catalytically reduced by hydrogen in the presence of palladium on charcoal to yield 2-amino-4-[3',5'-bis(2,3-dihydroxypropylmethylcarbamoyl)-2',4',6'-triiodophenyl]-benzoyl-D-glucosamine (20).

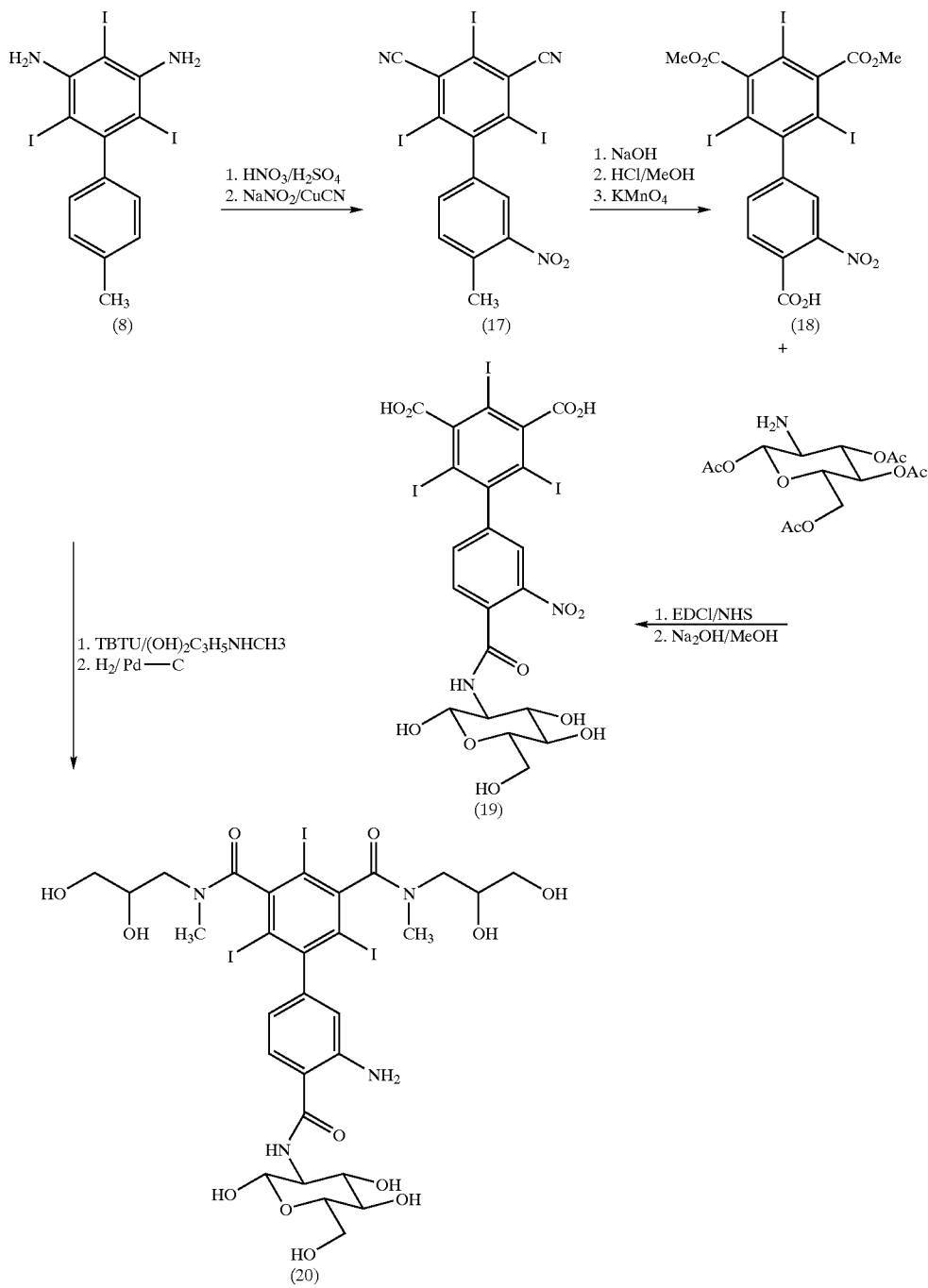

In Example 3, hydrophilic dihydroxypropylmethylcarbamoyl groups are substituted at the 3' and 5' positions of the radio-opaque triiodophenyl moiety to improve water solubility and provide shielding of the iodine atoms. The computed logP value of Example 3 is 2.56.

Many variations of Examples 1, 2, and 3 of the present invention will be apparent to one of ordinary skill in the art.

Atoms of elements other than iodine, with K-absorption edges (described in section E) in different regions of the X-ray photon energy spectrum used in radiographic imaging, may be substituted in the radio-opaque X moiety. These substituents may include elements with K-absorption edges in the lower range of the photon energy spectrum, such as bromine (Z=35, K-absorption edge=13.47 keV), and elements with K-absorption edges in the higher range of the photon energy spectrum, such as bismuth (Z=83, K-absorption edge=90.52 keV). The substitution of moieties with bromine has been disclosed by Dimo et al. in U.S. Pat. No. 4,474,747. The substitution of moieties with bismuth has been disclosed by Klaveness et al. in U.S. Pat. No. 5,817,289.

Additionally, as examples without limitation, unsubstituted or substituted alkyl, alkenyl, alkoxyalkyl, alkylthio, alkylamido, or similar groups may be used as the L moiety to link the S binding moiety to the X radio-opaque moiety.

One or more substituents may be positioned on the X moiety in proximity to the radio-opaque atoms to improve characteristics of the molecule that are of particular importance in radiographic imaging applications. These improvements include enhancement of water solubility and reduction of chemotoxicity in vivo. Substituents useful for these functions include, but are not limited to, acylamido, carbamyl, and polyhydroxyalkyl groups and further substituted combinations thereof. These substituents and their methods of synthesis are well known in the art [Hoey G B, Smith K R, in Sovak M ed., "Handbook of Experimental Pharmacology: Radiocontrast Agents", 73: 22–125, Springer-Verlag, New York (1984)]. If multiple groups are substituted, they may be the same or different. Methods for asymmetrical substitution of these groups are well known in the art [Speck U et al.: U.S. Pat. No. 4,364,921].

EXAMPLE 4

[$^{123}$I]-2-Amino-4-[3',5'-bis(N-acetamido)-2',4',6'-triiodophenyl]-benzoyl-D-glucosamine (21)

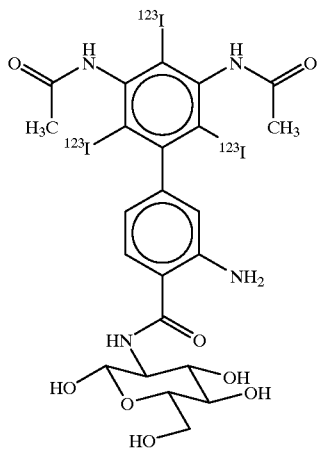

(20)

For use in imaging modalities such as SPECT, it may be advantageous to synthesize the radiolabeled form of Examples 1, 2, or 3. For example, one or more of the iodine atoms in the triiodophenyl moiety may be labeled with $^{123}$I.

2-amino4-[3',5'-bis(N-acetamido)-2',4',6'-triiodophenyl]-benzoyl-D-glucosamine (12) is mixed with a solution of [$^{123}$I]NaI in ethanol in the presence of dilute peracetic acid and mild heat. The radiolabeled product is separated using solid phase extraction and high-performance liquid chromatography.

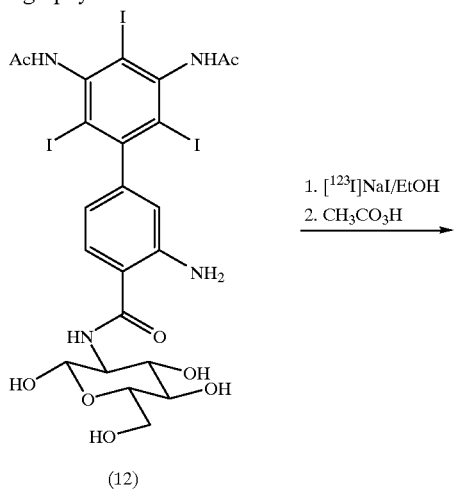

(12)

-continued

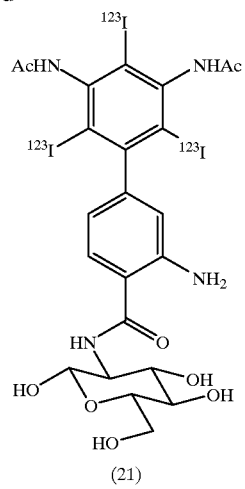

(21)

In Example 4, exchange radioiodination is used to replace non-radioactive $^{127}$I iodine atoms substituted in the triiodophenyl moiety with $^{123}$I atoms.

In one embodiment of the method according to the present invention, a radiolabeled imaging agent, [$^{123}$I]-2-amino4-[3',5'-bis(N-acetamido)-2',4',6'-triiodophenyl]-benzoyl-D-glucosamine (21) is administered to a live organism. After an interval to allow the imaging agent to accumulate throughout body tissue, the organism is appropriately positioned in relation to a gamma camera, and images are acquired. The acquired images may be used to detect and localize areas of abnormal tissue, such as malignant tissue, in which the imaging agent has accumulated at a different rate or concentration than in adjacent non-malignant tissue.

The examples shown above are directed toward imaging of hexokinase concentration in tissue, such as malignant and non-malignant tissue. However, it will be apparent to one of ordinary skill in the art that imaging agents for other target enzymes may be synthesized by combining a substrate or inhibitor of the enzyme with a radio-opaque or radioactive moiety in a manner that permits diffusion of the imaging agent across the cell membrane, selective binding to the target enzyme, and efficient exit of unbound imaging agent molecules across the cell membrane. Radio-opaque moieties may be employed for radiographic imaging applications, while radioactive moieties may be used for scintigraphic imaging applications. Imaging agents of this general form may be used for noninvasive measurements of a wide variety of normal and abnormal enzymes expressed at varying levels in normal and abnormal body tissue.

2. Imaging of Nucleic Acids

In situ hybridization is a technique for detection of specific DNA or RNA sequences within cells. The technique may be implemented with an oligonucleotide consisting of a single stranded, predefined sequence of nucleotides which is complementary to a selected nucleotide sequence in an intracellular target DNA or RNA molecule. Such oligonucleotides are generally obtained by chemical synthesis or by enzymatic polymerization.

A number of methods have been described for in situ hybridization of labeled oligonucleotides in living cells. Singer et al. (U.S. Pat. No. 5,728,527) disclosed a method of detecting labeled hybridized nucleotide probes in situ. In the disclosed method, oligonucleotides were labeled with a fluorophore or with a radioactive isotope. Cells were incubated in the presence of labeled oligonucleotide for a predetermined amount of time to allow the oligonucleotide to enter cells and to hybridize with intracellular target molecules. The cells were then washed to remove unhybridized oligonucleotides. The intracellular level of remaining hybridized oligonucleotides was then determined by measurement of fluorescence or radioactivity.

The technique has been extended to imaging of nucleotide sequences in vivo. Small tumors have been imaged with $^{111}$In-labeled oligonucleotides using a gamma camera in a mouse mammary tumor model [Dewanjee M K et al.: J. Nuc. Med. 35: 1054–1063 (1994). In vivo imaging of oligonucleotides using positron emission tomography has also been reported [Tavitian et al.: Nature Medicine 4: 467–471 (1998)]. In the PET study the positron emitter $^{18}$F was used to label oligonucleotides at the 3'-terminus of the oligomer.

Oligonucleotides have typically been synthesized with the native phosphodiester internucleotide linkages. It has been shown that phosphodiester-bonded oligonucleotides enter cells by means of receptor-mediated endocytosis [Loke S L et al.: Proc. Natl. Acad. Sci. USA 86: 3474–3478 (1989)]. In this mode of cellular entry, oligonucleotides molecules attach to receptors on the cell surface and are internalized into the cell through pinching off of the cell membrane to form intracellular vesicles. Although the oligonucleotides are physically localized within the cell, they are separated from the cytosol by the membrane surrounding the vesicles. They therefore do not have direct access to the cytosol, and because of this presumably interact with intracellular RNA and DNA molecules at a relatively inefficient rate.

Alterations have also been made to the phosphodiester backbone of oligonucleotides to decrease their negative charge and increase their lipophilicity. [Bischofberger et al: U.S. Pat. No. 5,763,208; Matteucci M: Ciba Found. Symp. 209: 5–18 (1997); Cook et al.: U.S. Pat. No. 5,610,289]. Alterations have also been made to oligonucleotides to increase their resistance to nucleases [Agrawal S, Zhang R: Ciba Found. Symp. 209: 60–75 (1997)].

The requirements for a functional radiographic imaging agent for imaging of target DNA and RNA sequences in vivo should include the use of an oligonucleotide sequence complementary to a target intracellular nucleic acid sequence. The imaging agent should be able to bidirectionally permeate the cell membrane and enter the cell with high efficiency. Cell membrane-permeability should increase the efficiency with which the oligonucleotides can hybridize with intracellular target DNA and RNA molecules. The imaging agent should be radio-opaque in the region of the photon energy spectrum used in diagnostic radiographic imaging. The imaging agent should also be resistant to degradation by nucleases.

Accordingly, one embodiment of the functional imaging agent of the present invention is a cell membrane-permeable radio-opaque oligonucleotide capable of binding to intracellular target DNA or RNA molecules. One embodiment of the imaging agent may use an oligonucleotide with a predetermined nucleotide sequence capable of hybridizing to a complementary nucleotide sequence present in abnormal or diseased body tissue. In one embodiment, the selected oligonucleotide may have a sequence complementary to an RNA or DNA target sequence expressed only in malignant tissue, only in normal tissue, or expressed at a different level in malignant tissue than in nonmalignant tissue. The radio-opacity of the imaging agent and its accumulation in cells containing the targeted nucleic acid sequence thus permits the detection of a predetermined nucleic acid sequence in vivo in a radiographic imaging procedure using the imaging methods of the present invention.

In one embodiment, a radio-opaque moiety is attached via a covalent linkage arm to the oligonucleotide at its 5'-terminus. In another embodiment, the radio-opaque moiety and linkage arm may be attached to the oligonucleotide at its 3'-terminus. The linkage arm is made sufficiently long so that the radio-opaque moiety does not impede hybridization of the oligonucleotide with the target molecule. In molecular modeling studies it was determined that a linkage arm of approximately 5–6 carbons, or approximately 5–6 Å in length, places the radio-opaque moiety a sufficient distance from a 5'-terminal nucleotide to prevent interference of hybridization of the oligonucleotide with a target sequence. A long linkage arm may also increase lipophilicity of the imaging agent and enhance its entry into cells. In one embodiment, an aromatic ring bonded to iodine atoms may be used as the radio-opaque moiety to provide strong carbon-iodine bonds and consequent resistance to deiodination in vivo.

In one embodiment, the imaging agent is capable of entering and exiting the cell via passive diffusion across the cell membrane. To enhance passive diffusion, the imaging agent molecule may be made lipophilic by either or both of two modifications of the native oligonucleotide. First, negatively charged phosphodiester linkages in the oligonucleotide backbone may be partially or completely replaced by formacetal, aminohydroxy, or other nonionic internucleotide linkages. Second, the oligonucleotide may be made additionally lipophilic. Methods for increasing lipophilicity include addition of hydrophobic moieties, such as an upper alkyl chain, to the 3'- or 5'-terminus of the oligomer. Lipophilic additions may also be made to one or more of the nucleotides with substitutions in purines, pyrimidines, or sugars.

The general form of one embodiment of the radio-opaque imaging agent is

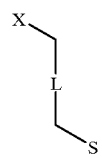

wherein:
   the S moiety is an oligonucleotide in which the nucleotide sequence comprises at least two residues;
   the X moiety is an unsubstituted or substituted $C_1$–$C_8$ alkyl, alkoxy, alkylthio, alkenyl, alkylaryl, alkylamino, alkylamido, amido, or arylamido, in which at least one atom is substituted by a radio-opacifying atom of an element with an atomic number of approximately Z=35 to approximately Z=74; and
   the L moiety is an unsubstituted or substituted $C_1$–$C_8$ alkyl, alkoxy, alkylthio, alkenyl, alkylaryl, alkylamino, alkylamido, amido, or arylamido, bonded to the S moiety and to the X moiety.

In one embodiment the internucleotide linkages of the S moiety may comprise nonionic linkages, including but not limited to formacetal or aminohydroxy linkages, between the C-5' position of the nucleotide sugar and the C-3' position of the adjacent nucleotide sugar.

In one embodiment, one or more lipophilic groups, including but not limited to $C_6$–$C_{30}$ alkyl chains, may be attached at one or more locations on the S moiety, the X moiety, and the L moiety.

Functionalized groups, including hydrophilic groups containing one or more hydroxyls or carbamoyls, may be also optionally be substituted at one or more positions of the X moiety to shield the radio-opacifying atom or atoms from causing chemotoxic responses in vivo.

EXAMPLE 5

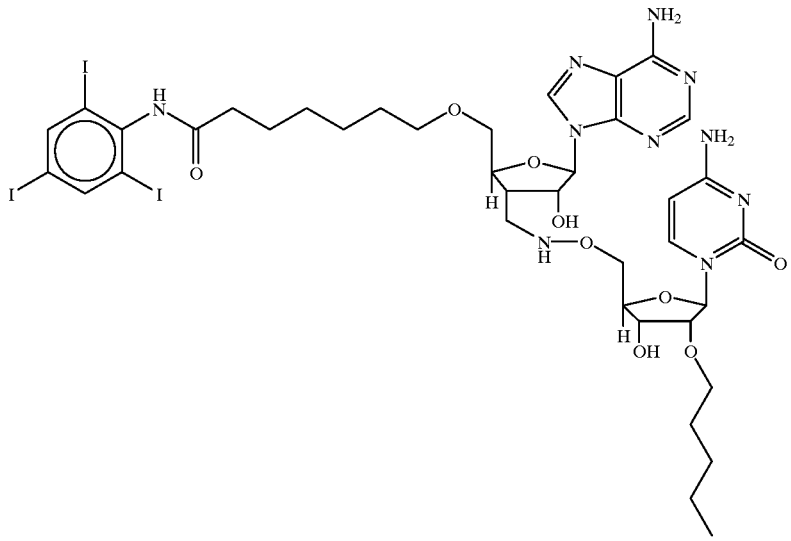

In Example 5, a oligonucleotide dimer is substituted with an aminohydroxy internucleotide linkage for the native phosphodiester linkage and a $C_8$ alkyl chain is substituted at a 2'-sugar position of the oligomer. The oligomer is linked to a radio-opaque moiety by means of a $C_6$ alkylamido linkage arm. One end of the linkage arm is bonded to the 5'-terminus of the oligomer, and the other end is bonded to a triiodophenyl moiety. The triiodophenyl configuration of the radio-opaque moiety provides strong carbon-iodine bonds and resistance to deiodination in vivo.

Methods for synthesis of the embodiments described above will be well known to one of ordinary skill in the art. Specifically, methods for synthesis of oligonucleotides and for conjugation of a wide variety of groups to the 3'-terminus and the 5'-terminus are well known [Crooke et al., eds: Antisense Research and Applications, CRC Press, Boca Raton Fla. (1993)]. Methods for synthesis of non-ionic internucleotide backbones have been described [Bischofberger et al.: U.S. Pat. No. 5,763,208; Cook et al.: U.S. Pat. No. 5,610,289]. Synthesis of oligonucleotides containing modifications to the 2'-sugar positions has also been described. [Keller T H, Haner R: Nucl. Acids Res. 21: 4499–4505 (1993); Buhr et al., U.S. Pat. No. 5,466,786].

Although the embodiments described in the present invention are directed toward the detection of nucleic acids expressed in malignant tissue, it will be evident to one skilled in the art that the method may be adapted for the radiographic detection of nucleic acids present in abnormal tissue in a wide variety of diseases. The method may additionally be also used to detect the presence of any nucleic acid sequence present in tissue, whether the nucleic acid originates in the tissue itself or in foreign organisms such as bacteria or viruses present in the tissue. In each case the specific oligonucleotide sequence to be used will be determined by the complementary DNA or RNA sequence to be detected.

3. Imaging of Fatty Acids

Many common cardiac disorders result in disturbances of myocardial metabolism. Because the oxidation of long-chain fatty acids is the major energy pathway in myocardial tissue, imaging of fatty acid metabolism has become an important modality for diagnosis of disorders of myocardial tissue. Abnormal rates of cellular uptake, synthesis, and breakdown of long-chain fatty acids have been demonstrated in a range of cardiac abnormalities, including coronary artery disease, myocardial infarction, cardiomyopathies, and ischemic tissue. [Railton R et al.: Euro. J. Nucl. Med 13: 63–67 (1987); Van Eenige M J et al.: Eur Heart J. 11: 258–268 (1990)].

Fatty acids generally enter cells through passive diffusion [Trigatti B L et al.: Biochem. J. 313: 487–394 (1996); Kamp F et al.: Biochemistry 34: 11928–11937 (1995); Kamp F et al.: Biochemistry 32: 11074–11086 (1993)]. After cellular entry, a portion of fatty acids undergo β-oxidation. The first step in this metabolic pathway is activation of the fatty acid molecule by combination with coenzyme A (CoASH) in the presence of ATP to form acyl CoASH. This step is catalyzed by fatty acyl coenzyme A synthetase, and occurs in the endoplasmic reticulum and the outer mitochondrial membrane. The remaining portion of fatty acids which enter myocardial cells is primarily incorporated into cellular triglycerides and membrane phospholipids. It has been demonstrated that the rates of β-oxidation and esterification of fatty acids are reduced in a wide range of myocardial disorders. Imaging of intracellular fatty acid metabolism using radio-labeled fatty acids in conjunction with SPECT and PET imaging devices has been shown to be an accurate diagnostic indicator of myocardial abnormality.

Accordingly, one embodiment of the present invention is a non-radioactive, radio-opaque imaging agent comprised of a long-chain fatty acid attached to a radio-opaque moiety. After administration to a patient, the imaging agent rapidly enters myocardial cells via passive diffusion across the cell membrane. The tissue distribution of this imaging agent may be imaged using the single and multiple beam imaging methods described in the present invention.

EXAMPLE 6

15-(p-Iodophenyl)pentadecanoic acid

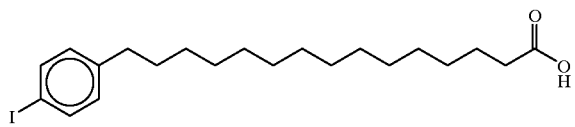

Example 6 shows an imaging agent comprising an ω-iodophenyl-substituted straight-chain fatty acid, 15-(p-Iodophenyl)pentadecanoic acid (IPPA). The radioactive form of this molecule, and its synthesis, has been described. [Machulla H J et al.: J. Nucl. Med. 19: 298–302 (1978)]. After entry into myocardial cells, a fraction of IPPA is quickly β-oxidized. Another fraction of the IPPA is incorporated into cardiac triglycerides and membrane phospholipids [Chien et al.: Am. J. Physiol. 245: H693–H697 (1983)]. In the embodiment of the current invention, the imaging agent is non-radioactive, which allows its use in cardiac imaging procedures using standard radiographic imaging devices. The need for synthesis of radiopharmaceuticals and gamma camera imaging is thereby eliminated. As in previous examples, the iodophenyl configuration provides a strong carbon-iodine bond and consequent resistance to deiodination in vivo. Example 6 is lipophilic, and enters and exits the cell via passive diffusion across the cell membrane. The computed logP of Example 6 is 8.09.

It will be apparent to one of ordinary skill in the art that variants of the non-radioactive, radio-opaque fatty acids described here may be readily synthesized. In particular, these variants include the replacement of straight chain fatty acids with methyl-branched and p-phenylene-bridged fatty acids to increase tissue retention time [Torikuza K et al.: Jpn. J. Nucl. Med. 28: 681–690 (1991); Eisenthut M et al.: Int. J. Rad. Appl. Instrum. 39: 639–649 (1988)].

4. Imaging of Other Targets

The embodiments of the radio-opaque functional imaging agent shown above are designed for the detection of enzymes, nucleic acids, and fatty acids. In addition, some of the embodiments of the present invention may be primarily used for the diagnosis of malignant tissue. However, radiographic imaging agents with a wide variety of diagnostic functions may be developed using the design principles disclosed in the present invention. For example, cell membrane-permeable imaging agents may be synthesized which selectively bind to carbohydrates, lipids, other intracellular molecules, or cell structures or organelles. The system and method may thus be modified to provide radiographic detection of other cellular targets of diagnostic importance.

In the examples shown in the present invention, the radio-opaque element in the imaging agent is iodine. However, it will be apparent to one skilled in the art that other elements exhibiting sufficient radio-opacity in the photon energy spectrum used in radiography, and possessing acceptable physiological and toxicological characteristics, may be incorporated into the radio-opaque moiety of the imaging agent. In each application, the choice of the element will depend on the goal of the diagnostic imaging procedure, the necessary physical and chemical characteristics of the imaging agent, and the energy spectrum of the transilluminating X-ray beam.

B. Single Beam Imaging System

FIG. 1 is a block diagram of a first embodiment of the imaging system, as used in an imaging procedure performed with a single, continuous spectrum, polyenergetic X-ray transilluminating beam. A cell membrane-permeable radio-opaque imaging agent 11 is administered to a patient. During a predetermined time interval the imaging agent accumulates in the patient's normal body tissue 12, and at a different rate in any abnormal tissue 13 that may be present.

An X-ray illumination source 20, which may include an ordinary X-ray tube with a tungsten anode 21, produces a continuous spectrum polyenergetic beam 22. A first collimator 23 directs the beam. A second collimator 25 further directs the beam. An X-ray image receptor 31, which may be radiographic film, a film/intensifying screen combination, a stimulable phosphor storage plate, a fluoroscopic image intensifier, an amorphous silicon sensor array, a CCD/scintillator combination, or another type of X-ray sensitive receptor, acquires a radiographic image of body tissue during transillumination by beam 22. A receptor interface 38 acquires 37 the received image in a manner dependent on the type of receptor 31. If the receptor is film or a film/intensifying screen combination, the film may be processed, and then viewed directly or scanned and digitized by the interface. If the receptor is a stimulable phosphor storage plate, the plate is read out and digitized by the interface. If the receptor is a fluoroscopic image intensifier or CCD/scintillator combination, the analog output of the detector is digitized by the interface. If the receptor is an amorphous silicon sensor array, the analog output is digitized by the interface or a digital output, if available, may be used directly. Receptor interface 38 transfers the digitized image data to an image processing system 32, which may be a computer, over signal lines 39.

Figure 1A:
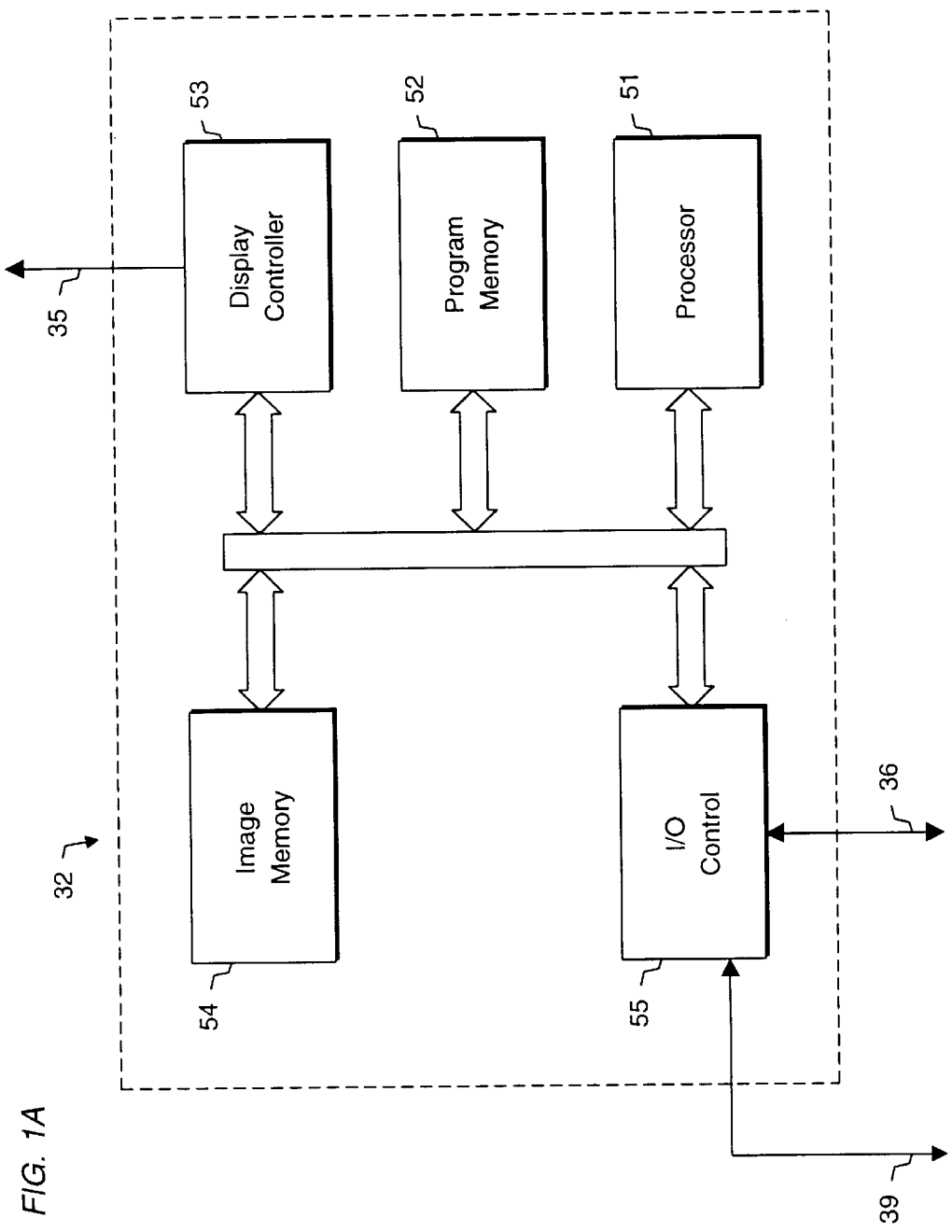
FIG. 1A is a block diagram of the image processing system.
Figure 2:
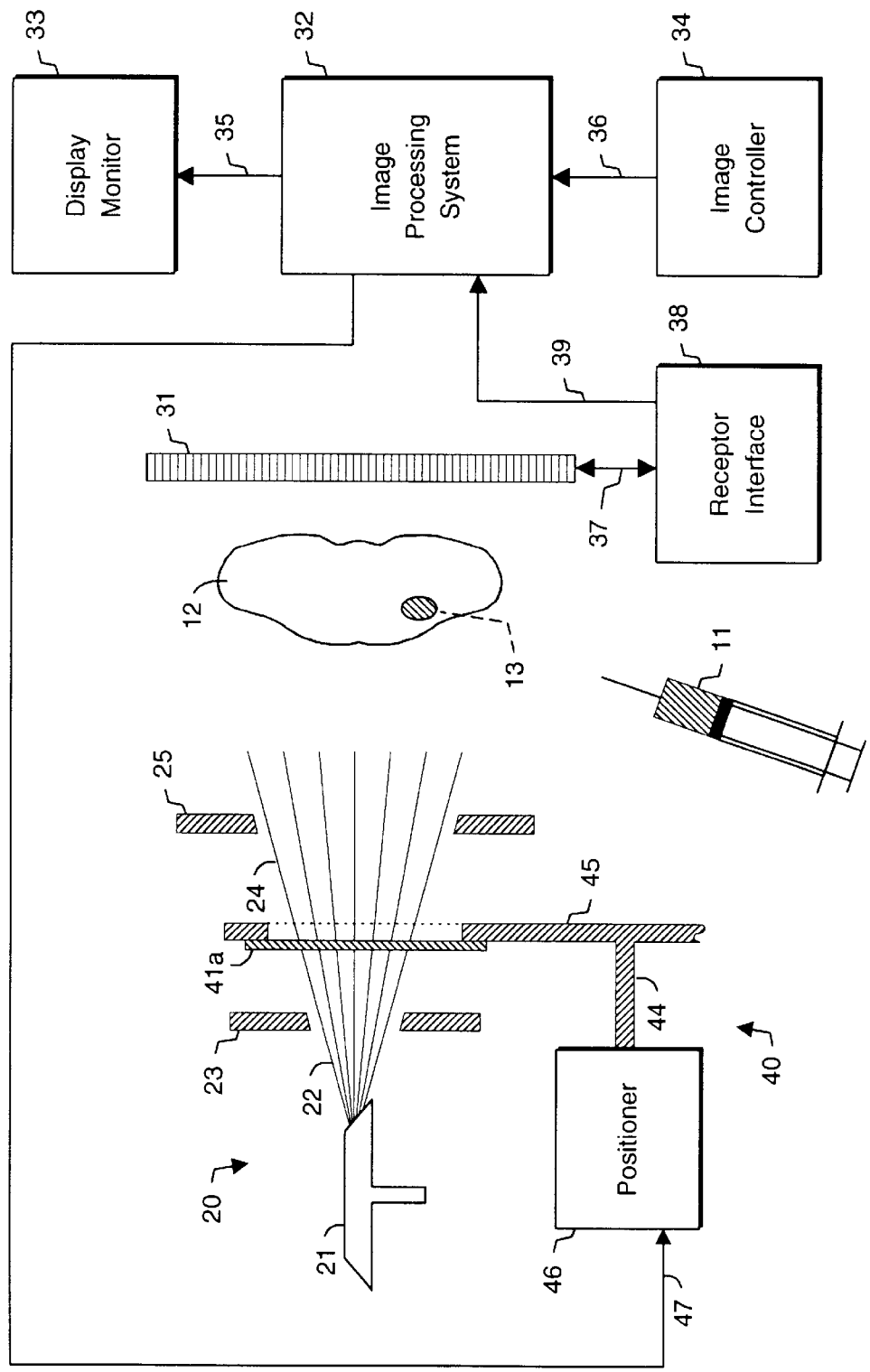
FIG. 2 is a block diagram of an embodiment of the imaging system using multiple X-ray transilluminating beams with different mean energy spectra.

A block diagram of image processing system 32 is shown in FIG. 1A. Components of the image processing system may all be contained on a single integrated circuit or distributed on multiple integrated circuits. A processor 51 may be a microprocessor, such as a Pentium Pro, or a general purpose programmable computer, or a dedicated digital signal processor (DSP) which is programmed to perform methods of the invention. The software of image processing system 32 may be stored in program memory 52, which may be ROM or RAM, or on a CD-ROM, or on a hard disk drive or on other storage media, or may be stored on processor chip 51. I/O control 55 receives digitized image data from image receptor 38 (FIGS. 1 and 2) over signal lines 39. The digitized image data is stored in image memory 54. After image processing, display controller 53 outputs the display image over signal lines 35 to a display monitor 33 (FIGS. 1 and 2).

Image processing system 32 may correct the data for linearity, converts the data to an image display format, and outputs the display image to a display monitor 33 over signal lines 35, and optionally to a hard copy device (not shown) which may be a printer. Image processing system 32 may also store the image in digital form on a hard disk, a tape drive, or another storage device (not shown).

C. Single Beam Imaging Method

If a quantity of radio-opaque imaging agent accumulates in body tissue and a radiographic image of the tissue is then acquired, the image will display the radiographic density contributed by the imaging agent combined with the radiographic density contributed by soft tissue and bone also present in the beam path. If a sufficiently large quantity of imaging agent accumulates, it may be detected and localized by direct inspection of the radiographic image. Optionally, the image may be digitized and processed using the standard methods of digital radiography, including digital filtering and contrast enhancement. If the radiographic density of the accumulated imaging agent is too low to be detected when combined with the radiographic density of soft tissue and bone, the multiple beam imaging system and method described in sections D and E may be used to isolate the radiographic density contributed by the imaging agent.

D. Multiple Beam Imaging Systems

FIG. 2 is a block diagram of a second embodiment of the imaging system, as used in a multiple beam imaging procedure performed with two or more quasi-monoenergetic X-ray transilluminating beams with different mean energy spectra. In the example of the embodiment shown in FIGS. 2, 3A, and 3B, three transilluminating beams are used.

Cell membrane-permeable radio-opaque imaging agent 11 is administered to a patient. During a predetermined time interval the imaging agent accumulates in the patient's normal body tissue 12, and in any abnormal tissue 13 that may be present.

X-ray illumination source 20, which may include an ordinary X-ray tube with a tungsten anode 21, produces continuous spectrum polyenergetic beam 22. First collimator 23 directs the beam. An X-ray filter apparatus 40 comprises a filter wheel 45, X-ray filters 41a, 42a, 43a (shown on FIG. 3B), a shaft 44, a positioner 46, and position control signals 47 generated by image processing system 32.

FIGS. 3A and 3B depict X-ray filter apparatus 40 and its relation to X-ray illumination source 20 in greater detail. Positioner 46, which may be a stepping motor whose angular shaft position is controlled by control signals 47, is mechanically coupled to filter wheel 45 through shaft 44. Control signals 47 may be generated by image processing system 32. Positioner 46 rotates the filter wheel to sequentially interpose each of filters 41a, 42b, 43c in the path of beam 22. As each of the filters is interposed in beam 22, the positioner stops rotation of the filter wheel, and a separate radiographic image is acquired. The filter wheel is then rotated to interpose the next filter in the path of beam 22.

Filter wheel 45 preferably comprises a circular mounting disc 48, made from a highly radio-opaque material, containing a plurality of cut-out apertures 41b, 42b, 43b arranged in a regularly spaced circular array. X-ray filters 41a, 42a, 43a are concentrically mounted on apertures 41b, 42b, 43b, respectively. Each X-ray filter contains a different substance that converts polyenergetic X-ray beam 22 into a quasi-monoenergetic transilluminating beam 24 with a unique mean energy spectrum. The mean energy spectrum of each filtered beam is determined by the X-ray absorption characteristics of the substance contained in the filter. The method for selection of the spectra of the beam is described in section E, and the method for selection of the filters is described in section G.

FIG. 2 shows second collimator 25, which further directs quasi-monoenergetic transilluminating beam 24 after it has passed through the X-ray filter. X-ray image receptor 31, which may be radiographic film, a film/intensifying screen combination, a stimulable phosphor storage plate, a fluoroscopic image intensifier, an amorphous silicon sensor array, a CCD/scintillator combination, or another type of X-ray sensitive receptor, acquires a radiographic image of body tissue during transillumination by beam 22. A receptor interface 38 acquires 37 the received image in a manner dependent on the type of receptor 31. If the receptor is film or a film/intensifying screen combination, the film may be processed, scanned and digitized by the interface. If the receptor is a stimulable phosphor storage plate, the plate is read out and digitized by the interface. If the receptor is a fluoroscopic image intensifier or CCD/scintillator combination, the analog output of the detector is digitized by the interface. If the receptor is an amorphous silicon sensor array, the analog output is digitized by the interface, or a digital output, if available, may be used directly. Receptor interface 38 transfers the digitized image data to image processing system 32 over signal lines 39.

A block diagram of image processing system 32 is shown in FIG. 1A. Components of the image processing system may all be contained on a single integrated circuit or distributed on multiple integrated circuits. A processor 51 may be a microprocessor, such as a Pentium Pro, or a general purpose programmable computer, or a dedicated digital signal processor (DSP) which is programmed to perform methods of the invention. The software of image processing system 32 may be stored in program memory 52, which may be ROM or RAM, or on a CD-ROM, or on a hard disk drive or other storage media, or may be stored on processor chip 51. I/O control 55 receives digitized image data from image receptor 38 (FIGS. 1 and 2) over signal lines 39. The digitized image data is stored in image memory 54. After image processing, display controller 53 outputs the display image over signal lines 35 to a display monitor 33 (FIGS. 1 and 2). I/O control 55 may also receive input signals from image controller 34 via a keyboard or mouse over signal lines 36. The image control and display methods are described in detail in section F. By means of these input signals, the viewer may switch between the display of either an anatomical or functional images, or, alternatively, display variable proportions of anatomical and functional images on a single image in registration.

Image processing system 32 linearizes the digitized data and performs an image processing procedure to enhance and display the image. (The image acquisition and processing procedures are described in section E). Image processing system 32 outputs the display image to a display monitor 33 over signal lines 35, and optionally to a hard copy device (not shown) which may be a printer. Image processing system 32 may also store the image in digital form on a hard disk, a tape drive, or another storage device (not shown).

An image controller 34, which may be a keyboard or a mouse, is connected to image processing system 32 over signal lines 36. The viewer uses image controller 34 to vary one or more of the display coefficients applied by the image processing procedure to the anatomical and functional images to be displayed. Changing the value of the display coefficients varies the degree to which imaging agent, and soft tissue and bone contribute radiographic density to the display image. The viewer may thus superimpose a variable level of the anatomical image (soft tissue and bone) on the functional image (accumulated imaging agent).

Figure 4:
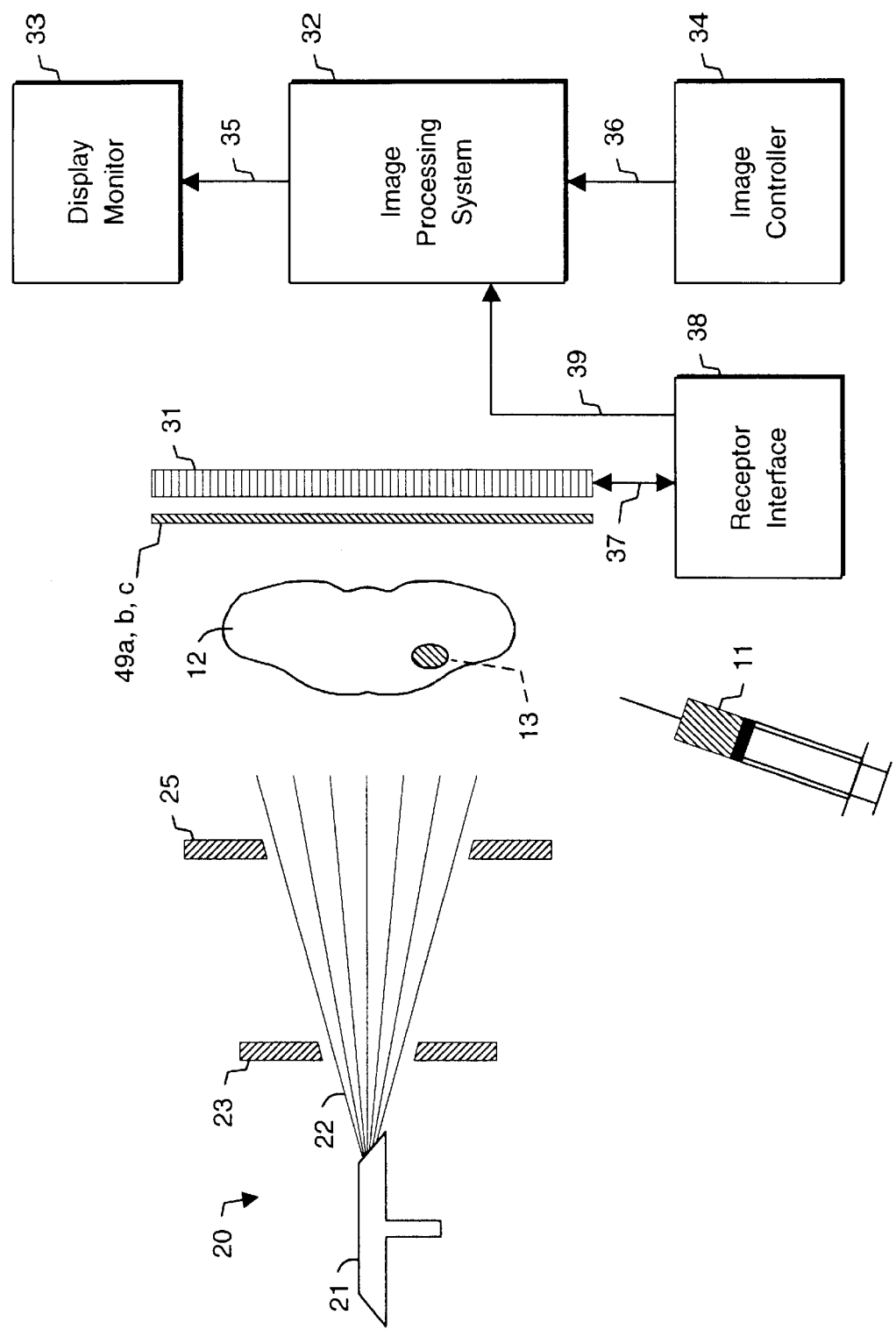
FIG. 4 is a block diagram of an embodiment of the imaging system using a single polyenergetic X-ray transilluminating beam and filtering of the beam between the patient and the image receptor.

FIG. 4 is a block diagram of a third embodiment of the imaging system, as used in a imaging procedure performed with a single, continuous spectrum, polyenergetic X-ray transilluminating beam. After the beam transilluminates the patient's body tissue, it is sequentially filtered to generate multiple beams with different mean energy spectra, and a separate radiographic image is acquired during generation of each beam.

Cell membrane-permeable radio-opaque imaging agent 11 is administered to a patient. During a predetermined time interval the imaging agent accumulates in the patient's normal body tissue 12, and in any abnormal tissue 13 that may be present.

X-ray illumination source 20, which may include an ordinary X-ray tube with a tungsten anode 21, produces continuous spectrum polyenergetic beam 22. First collimator 23 directs the beam. A second collimator 25 further directs beam 22, which transilluminates the patient's body tissue 12,13.

A series of X-ray filters 49*a, b, c* is interposed in temporal sequence between the patient's body tissue and image receptor 31. Each of the filters sequentially converts polyenergetic beam 22 into a quasi-monoenergetic beam with a different mean energy spectrum. In one embodiment, each X-ray filter may comprise a thin sheet of a substance with selected X-ray attenuation characteristics. This substance, which may have a K-absorption edge at a predetermined photon energy, filters the beam to enable the transmission of a predetermined energy spectrum to the image receptor. The method for selection of the spectra of the beams is described in section E, and the method for selection of the filters is described in section G.

The filter sheet may be positioned adjacent to image receptor 31, which may comprise a film/intensifying screen combination, a stimulable phosphor storage plate, a fluoroscopic image intensifier, an amorphous silicon sensor array, a CCD/scintillator combination, or another type of X-ray sensitive receptor.

Each X-ray filter contains a different substance that converts polyenergetic X-ray beam 22 into a quasi-monoenergetic beam 24 with a unique mean energy spectrum. The mean energy spectrum of each filtered beam is determined by the X-ray absorption characteristics of the substance contained in the filter. The method for selection of the spectra of the beam is described in section E, and the method for selection of the filters is described in section G.

X-ray image receptor 31, which may be radiographic film, a film/intensifying screen combination, a stimulable phosphor storage plate, a fluoroscopic image intensifier, an amorphous silicon sensor array, a CCD/scintillator combination, or another type of X-ray sensitive receptor, acquires a radiographic image of body tissue during transillumination by beam 22. A receptor interface 38 acquires 37 the received image in a manner dependent on the type of receptor 31. Subsequent acquisition and processing of the radiographic images are similar to those described earlier in this section for the multiple beam imaging system using the filter wheel apparatus.

In one embodiment of the multiple beam imaging system, the requirement for a sequence of transilluminating X-ray beams with different mean energy spectra is satisfied by filtration of a polyenergetic beam, in temporal sequence, through substances with selected X-ray absorption characteristics. However, it will be obvious to one skilled in the art that this requirement may also be satisfied by other means. For example, an X-ray monochromator may be sequentially tuned to produce monoenergetic beams with the required energy spectra. Alternatively, a tuned synchrotron may be used to produce monoenergetic beams with the required spectra.

E. Multiple Beam Imaging Method

If a quantity of radio-opaque imaging agent accumulates in body tissue and a radiographic image of the tissue is then acquired, the image will display the radiographic density contributed by the imaging agent combined with the radiographic density contributed by soft tissue and bone also present in the beam path. If a small quantity of imaging agent accumulates in the tissue being examined, visualization of the imaging agent should be enhanced. The radiographic density it contributes to the image should therefore be isolated and selectively displayed. A number of approaches to this problem have been described [Kelcz F, Mistretta C A: Med. Phys. 3: 159–168 (1976); Kelcz F et al.: Med. Phys. 4: 26–35 (1977); Riederer S J et al.: Med. Phys. 8: 471–479 (1981); Riederer S J et al.: Med. Phys. 8: 480–487 (1981); Macovski A et al.: Med. Phys 6: 53–58 (1979)].

The multiple beam imaging method generates a radiographic image which emphasizes the radiographic density of accumulated imaging agent and almost completely cancels the radiographic density of the soft tissue and bone present in the beam path. To enhance the image in this manner, body tissue being examined is sequentially transilluminated by two or more beams with different preselected mean energy spectra, and a separate image is acquired during transillumination by each beam. The separate acquired images are then combined, using image weighting coefficients, into a single image.

The transilluminating beams may be quasi-monoenergetic or monoenergetic, and their spectra are selected based on the K-absorption edge of the radio-opaque element contained in the imaging agent.

For each element in the periodic table there is a unique profile of X-ray attenuation over the photon energy spectrum, and, most importantly, a characteristic energy at which X-ray attenuation sharply increases. This abrupt increase in attenuation is known as the K-absorption edge. The K-absorption edge for each element is unique, and is monotonically related to the atomic number of the element.

In one embodiment of a multiple beam imaging method, one beam is selected to have a mean energy spectrum just below the K-absorption edge of the radio-opaque element in the imaging agent, and a second beam is selected to have a mean energy spectrum just above the K-absorption edge of the radio-opaque element.

The principle of operation of the method is illustrated in the following example. Assume that a quantity of radio-opaque imaging agent has accumulated in an area of body tissue under examination. The tissue is first transilluminated by beam $E_1$ with a mean energy spectrum just below the K-absorption edge of the radio-opaque element in the imaging agent, and image $X_1$ is acquired. Absorption of beam $E_1$ by the imaging agent will be relatively low, and the radiographic density it contributes to image $X_1$ will be correspondingly high.

The tissue is then transilluminated by beam $E_2$ with a mean energy spectrum just above the K-absorption edge of the radio-opaque element in the imaging agent, and image $X_2$ is acquired. Because there is a sharp increase in X-ray attenuation at the K-absorption edge of the element, absorption of beam $E_2$ by the imaging agent will be relatively high, and the radiographic density it contributes to image $X_2$ will be correspondingly low.

Soft tissue will contribute a nearly equal level of radiographic density to image $X_1$ and to image $X_2$. This is because the K-absorption edges of the elements which comprise soft tissue (predominantly carbon, hydrogen, oxygen, and nitrogen), are located well below the mean energy spectra of beams $E_1$ and $E_2$. Thus, the absorption of beams $E_1$ and $E_2$ by soft tissue will be nearly equivalent.

Bone will also contribute a nearly equal level of radiographic density to image $X_1$ and to image $X_2$. This is because the K-absorption edges of the elements which comprise bone (predominantly carbon, hydrogen, oxygen, nitrogen, and calcium) are likewise located well below the mean energy spectra of beams $E_1$ and $E_2$. Thus, the absorption of beams $E_1$ and $E_2$ by bone will be nearly equivalent.

If image $X_2$ is then subtracted from image $X_1$ to produce image Z, the relatively large difference between the radiographic density contributed by the accumulated imaging agent in images $X_1$ and $X_2$ will result in a relatively high level of residual radiographic density in subtracted image Z. The approximately equal levels of radiographic density contributed by soft tissue to images $X_1$ and $X_2$ and by bone to images $X_1$ and $X_2$ will result in relatively low levels of residual radiographic density in subtracted image Z. Thus, by computing the difference image of images $X_1$ and $X_2$, the radiographic density of imaging agent is preserved in the resulting image Z, and the radiographic density of soft tissue and bone is essentially canceled.

A viewer may switch between a display showing image Z, and an anatomical image (e.g. image $X_1$) which is aligned in registration with image Z. In this manner, the anatomical and functional tissue images may be separately viewed. Alternatively, image Z may be combined with image $X_1$ or image $X_2$, in registration, to produce a single anatomical and functional image.

In practice, the attenuation of beams $E_1$ and $E_2$ by soft tissue are not exactly equal. Likewise the attenuation of beams $E_1$ and $E_2$ by bone are not exactly equal. A residual level of radiographic density due to soft tissue and bone therefore remains after subtraction of image $X_2$ from image $X_1$. To optionally compensate for these residuals, a third beam $E_3$ may be generated with a mean energy spectrum well above the mean energy spectrum of beam $E_2$, and a third image $X_3$ acquired during transillumination of the tissue by beam $E_3$. Appropriate weighting of image $X_3$, and its combination with weighted images $X_1$ and $X_2$, produces a display image Z with almost complete cancellation of the radiographic density of soft tissue and bone.

When a quasi-monoenergetic beam traverses a length of soft tissue and bone, its mean energy spectrum slightly increases. This phenomenon is known as beam hardening, and, if uncorrected, may reduce the degree of cancellation of soft tissue and bone in the displayed image. Accordingly, in one embodiment of the multiple beam imaging method, additional higher order terms may be applied as weighting coefficients to images $X_1$, $X_2$, and $X_3$ to compensate for beam hardening and further improve the cancellation of soft tissue and bone on the displayed image.

In summary, by the general method of:
1) administering a bidirectionally cell membrane-permeable, radio-opaque imaging agent to a patient;
2) allowing an interval for accumulation of the imaging agent in body tissue;
3) sequentially transilluminating the tissue under examination with multiple X-ray beams $E_1, \ldots, E_n$ with different mean energy spectra;
4) acquiring a separate radiographic image $X_1, \ldots, X_n$ during transillumination by each beam;
5) multiplying the acquired images $X_1, \ldots, X_n$ by weighting coefficients $w_1, \ldots, w_n$ respectively, and optionally multiplying images $X_1^2, \ldots, X_n^2$ by weighting coefficients $h_1, \ldots, h_n$ to compensate for beam hardening during tissue transillumination;
6) adding all weighted images to produce a display image Z;

the relative contributions of the radio-opaque imaging agent, soft tissue, and bone to radiographic density on display image Z may be computed and isolated. By the additional step of:

7) displaying a viewer-controlled fraction of display image Z together with a fraction of any one of images $X_1, \ldots, X_n$, a variable proportion of the functional and anatomical images of the tissue being examined may be displayed, with both images in complete registration.

Figure 8:
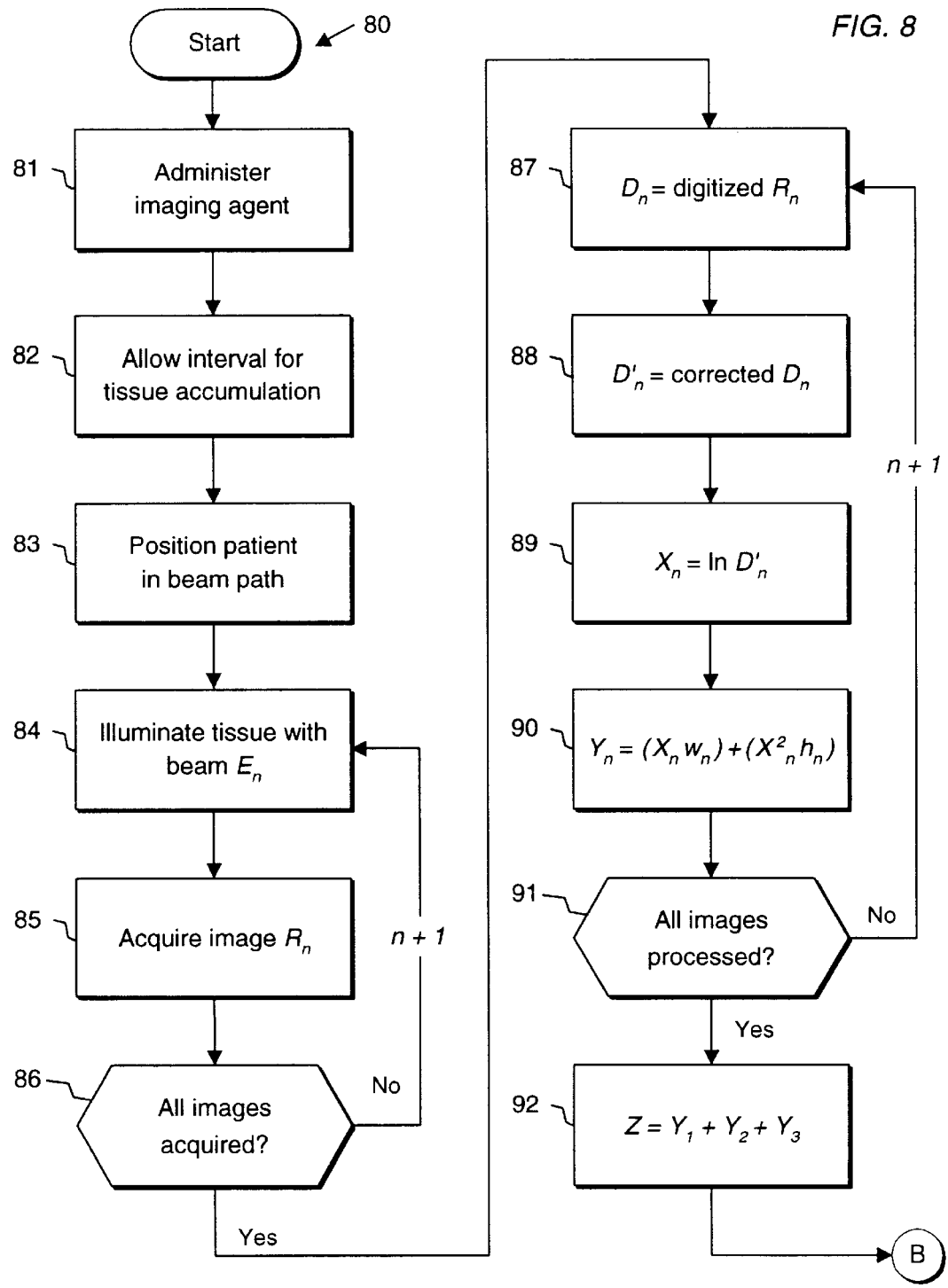
FIG. 8 is a flow chart of the multiple beam image acquisition and processing procedure.

A flow chart of the image acquisition and processing procedure 80 is shown in FIG. 8. A radio-opaque functional imaging agent is administered 81 to a patient. During a predetermined time interval 82 the imaging agent accumulates in the patient's body tissue. The patient is then positioned 83 appropriately between the X-ray source and image receptor.

An X-ray beam $E_1$ transilluminates 84 the body tissue being examined, and a radiographic image $R_1$ is acquired 85. The sequence of transillumination and image acquisition is repeated 86 for beam $E_2$ and image $R_2$, and beam $E_3$ and image $R_3$, respectively.

The following image processing procedure is performed on each radiographic image in sequence. Radiographic image $R_1$ is digitized 87 to generate digital image $D_1$. The radiographic image may be digitized immediately after acquisition of each image, digitized after acquisition of the entire series of images, or stored for digitization at some later time. After digitization, image processing may be performed immediately, or the digital arrays may be stored in random-access memory, on a hard drive, on tape, or on other digital storage media for later processing. Thus, $$D_1 = \text{digitized } R_1$$

Corrections to linearize the transfer function of the X-ray image receptor may then be applied 88 to the digital array. The correction may be implemented by one or more hardware-based lookup tables. The input to the lookup tables may be the uncorrected output value of the analog-to-digital converter and the output of the lookup table would then be the linearized. Alternatively, the correction may be performed in software by one or more lookup tables stored in random-access memory, on a hard disk, or on other storage media. Thus, $$D'_1 = \text{corrected } D_1$$

A number of image receptor systems are now available and others are being developed for acquiring radiographic images in a form suitable for digital processing. These receptor systems include, but are not limited to, stimulable phosphor storage plates, fluoroscopic image intensifiers, amorphous silicon sensor arrays, and CCD/scintillator combinations. For clarity in the description of the image processing procedure, it is assumed that the image receptor used in the present invention is characterized by a) a substantially linear relationship between X-ray photon energy input and detector signal output, and b) a substantially linear detector response in the photon energy spectrum between approximately 10 keV and approximately 60 keV. If an image receptor with nonlinear gain or spectral response characteristics is used in the present invention, the nonlinearity may be appropriately corrected by hardware or software. The correction is based on the predetermined response of the image receptor to the range of photon input levels and energy spectra used in the imaging procedure. The image array is therefore assumed to have a linear relationship to the input X-ray signal after correction 88. The modifications necessary to achieve this correction are mathematically straightforward, and will be evident to one of ordinary skill in the art.

After digitization and correction, the natural logarithm of the value of each pixel in the digital image $D'_1$ is computed 89 to generate image $X_1$ $$X_1 = \ln D'_1$$

Image processing system 32 multiplies 90 each pixel value in image $X_1$ by weighting coefficient $w_1$. In one embodiment an additional higher order term may be added to compensate for the slight beam hardening, or increase in mean beam energy, and resulting small decrease in effective mass attenuation coefficient that occurs when each quasi-monoenergetic beam passes through a thickness of tissue or bone. This term is equal to $X_1^2$ multiplied by hardening coefficient $h_1$. The entire image weighting term function is $$Y_1 = (X_1 w_1) + (X_1^2 h_1)$$

Figure 9:
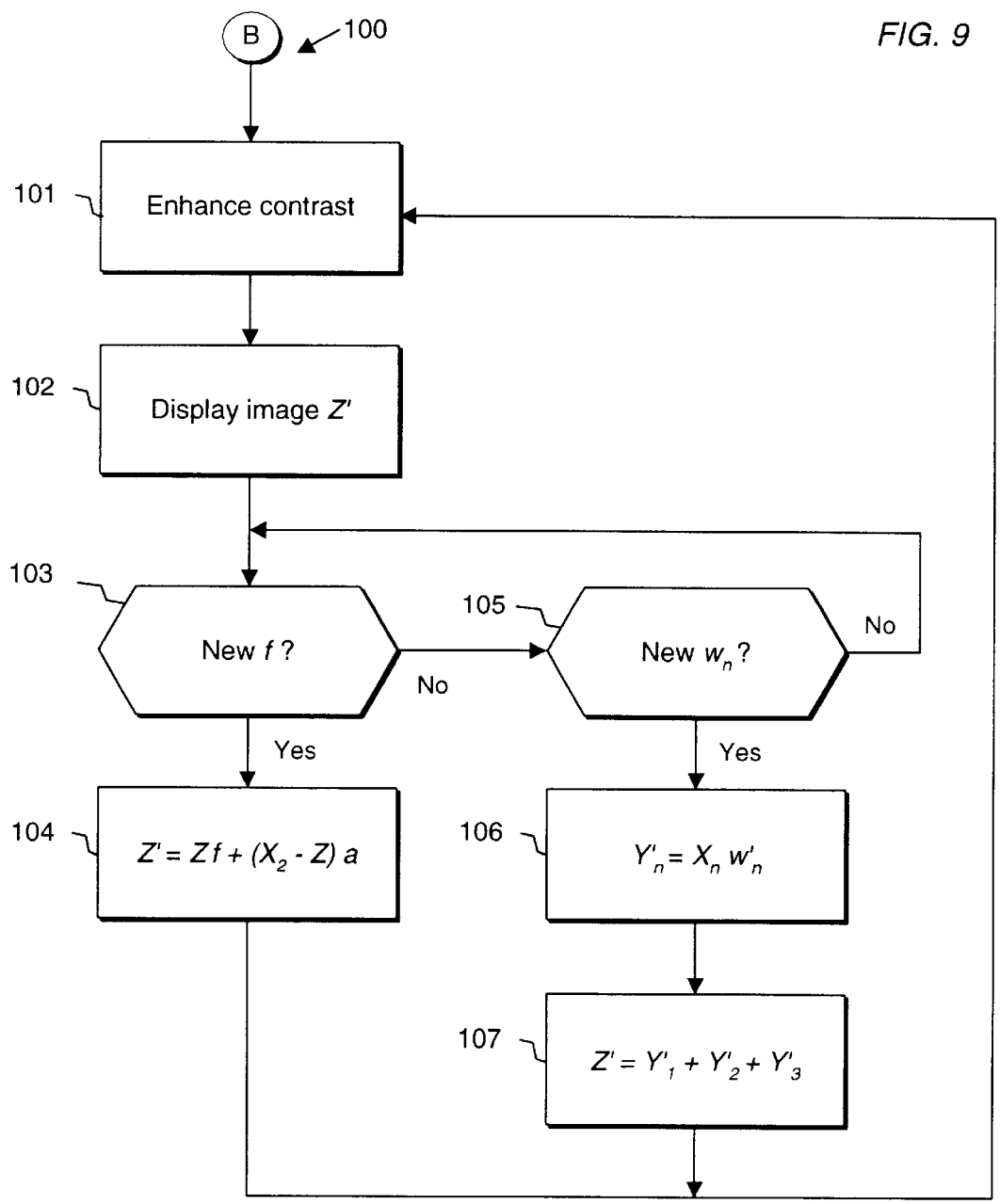
FIG. 9 is a flow chart of the image control and display procedure.

Image digitization, correction, log conversion, and image weighting is repeated 91 for radiographic images $R_2$ and $R_3$. The image combination formula, which in one embodiment is $$Z = Y_1 Y_2 + Y_3$$

is then performed 92 to yield display image Z. Image Z is displayed 93 on the display monitor, as shown in FIG. 9. As described in section F below, image Z may be modified by the user to display varying proportions of imaging agent, soft tissue and bone present in the beam path. Image Z may also be converted to hard copy, and may be stored in random-access memory, on a hard drive, on tape, or on another digital storage medium for archiving and for later viewing.

Table 2 shows the mean energy spectra for beams $E_1$, $E_2$, and $E_3$, the corresponding image weighting coefficients $w_1$, $w_2$, and $w_3$, and hardening coefficients $h_1$, $h_2$, and $h_3$ used in one embodiment of the multiple beam imaging method. These coefficients are used in the image weighting step 90 of FIG. 8.

TABLE 2

| Beam | keV | Image | w | h |
|---|---|---|---|---|
| $E_1$ | 31.05 | $X_1$ | −30.5 | 0.11 |
| $E_2$ | 37.10 | $X_2$ | 99.7 | −0.43 |
| $E_3$ | 44.10 | $X_3$ | −67.4 | 0.25 |

Table 3 shows typical concentrations of imaging agent, soft tissue and bone present in the transilluminating X-ray beam path and their attenuation of beams $E_1$, $E_2$, and $E_3$. The table also shows levels of radiographic density present on acquired images $X_1$, $X_2$ and $X_3$, and the radiographic density present on display image Z after application of the image processing procedure described above.

TABLE 3

| Image component | Thickness gm/cm² | Beam Transmittance | | | Relative density |
|---|---|---|---|---|---|
| | | $E_1$ | $E_2$ | $E_3$ | |
| Iodine | 0.001 | 99.03 | 97.68 | 98.35 | 1.00 |
| Soft tissue | 12.000 | 69.42 | 74.93 | 78.91 | 0.00 |
| Bone | 3.000 | 24.85 | 40.11 | 58.27 | 0.03 |

F. Image Control and Display Methods

A flow chart of the image control procedure 100 is shown in FIG. 9. The weighted and combined image Z resulting from step 92 (FIG. 8) is an image of relatively low visual contrast. A contrast enhancement procedure, such as a level shift and histogram stretch, may be first performed 101 to enhance the visual contrast of image Z, to produce image Z'.

After completion of the image acquisition and processing procedure, each of unweighted, uncombined images $X_1$, $X_2$ and $X_3$ is an anatomical image, represented by radiographic density contributed by soft tissue and bone, and also containing radiographic density contributed by accumulation of the radio-opaque imaging agent. Weighted and combined image Z is solely a functional image. The viewer may interactively vary the displayed proportions of the anatomical and functional images, and the combined images will be displayed on a single image in complete registration. Display coefficient $f$ represents the displayed proportion of the functional image, and display coefficient a, which is forced to $(1-f)$, represents the displayed proportion of the anatomical image. In one embodiment, the value of $f$ is initially set at 1.0 when a new image Z' is displayed, so that only the functional image is first displayed. While image Z' is displayed 102 on the display monitor, image processing system 32 (FIG. 2) periodically tests 103 for a change in coefficient $f$, which the viewer selects using image controller 34 (FIG. 2). When a change is detected in coefficient $f$, the image processing system combines 104 the selected proportions of functional image Z and image $X_1$, performs contrast enhancement, and redisplays 102 the resulting new image Z' on the display monitor. Image Z' may also be stored in random-access memory, on a hard drive, or on another storage device.

While viewing the displayed image, the viewer may thereby interactively superimpose a variable proportion of the anatomical image on the functional image. Since the anatomical and functional images are displayed in complete registration, this capability facilitates precise localization of malignant tissue, or other tissue which is labeled by the imaging agent, with reference to nearby anatomical landmarks.

A small unwanted residual density contributed by soft tissue or bone may remain on display image Z after image processing using the predetermined weighting coefficients used in the image processing procedure described in section E. The viewer may interactively adjust the image weighting coefficient of image $X_3$ to completely cancel this residual.

While image Z' is displayed 102 on the display monitor, image processing system 32 (FIG. 2) periodically tests 105 for a change in weighting coefficient $w_3$, which is controlled by the viewer using image controller 34 (FIG. 2). A change in the value of weighting coefficient $w_3$ changes the contribution of image $Y_3$ to display image Z, and therefore the degree to which soft tissue and bone are canceled in image Z. When a change in the weighting coefficient is detected, the image processing system recomputes the image 106, 107 using the new coefficient $w_3$ performs contrast enhancement 101 to stretch the recomputed image to full scale, and displays 102 the recomputed image Z' on the display monitor.

G. X-ray Filter Apparatus

Different approaches may be used to generate the quasi-monoenergetic or monoenergetic X-ray beams required for the multiple beam imaging method. In one embodiment of the present invention, an X-ray filter apparatus sequentially generates multiple quasi-monoenergetic beams with different mean energy spectra. However, alternative methods for generating multiple quasi-monoenergetic or monoenergetic X-ray beams, each having a unique energy spectrum, may be also be used with the present invention.

Operation of the filter apparatus is based on the principle that a polyenergetic X-ray beam may be converted into a quasi-monoenergetic beam, with a unique mean energy spectrum, by filtering the polyenergetic beam through a substance containing an element with selected X-ray attenuation characteristics. Specifically, a substance with a K-absorption edges at a selected photon energy is used to generate a beam with the desired energy spectrum.

Figure 5A:
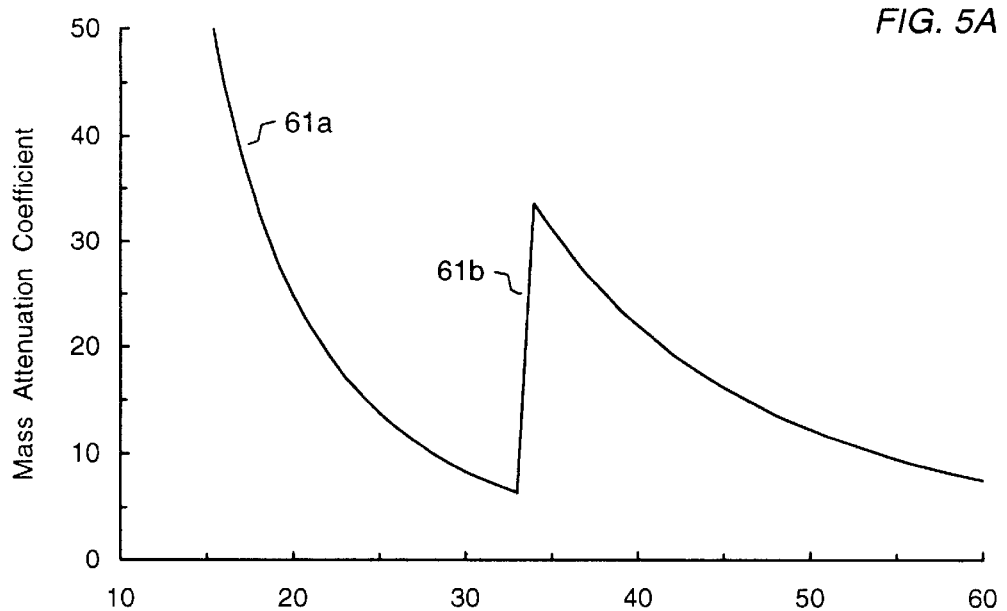
FIG. 5A shows the mass attenuation coefficient of iodine as a function of photon energy.

As described previously, for each element in the periodic table there is a characteristic photon energy at which X-ray attenuation sharply increases. This abrupt increase in attenuation is known as the K-absorption edge. An example of a K-absorption edge is shown in FIG. 5A. A graph 61a of the mass attenuation coefficient of iodine (I, Z=53) is plotted as a function of photon energy from 10 to 60 keV. K-absorption edge 61b appears as an abrupt increase in the mass attenuation coefficient at 33.1 keV.

Each X-ray filter 41a, 42a, and 43a (FIG. 3B) contains a different substance which transforms polyenergetic X-ray beam 22 into a quasi-monoenergetic transilluminating beam 24 with a unique mean energy spectrum.

As noted in section E, the mean energy spectrum of transilluminating beam $E_1$ should be just below the K-absorption edge of the radio-opaque element whose radiographic density is to be isolated. The mean energy spectra of beam $E_2$ should be above the K-absorption edge of the radio-opaque element. In one embodiment, a third transilluminating beam $E_3$ is used and should have a mean energy spectrum above that of beam $E_2$. In one embodiment of the imaging agent in the present invention, the radio-opaque element used is iodine. In this case, substances which may be used to filter polyenergetic beams to convert them into quasi-monoenergetic beams with appropriate mean energy spectra include iodine, cerium, and brass. The X-ray filters may be implemented with cylindrical cells containing solutions of the substances selected for beam filtration, or with solid disks of metal. The required concentrations of the filter substances in solution and the thicknesses of the solid metal filters are readily calculated using their mass attenuation coefficients.

Attenuation of an X-ray beam by passage through a substance is described by the exponential attenuation law:

$$I(E)/I_0(E) = \exp[-(\mu/\rho)x]$$

where I(E) is the output intensity of the beam, $I_0$(E) is the incident intensity of the beam, and $\mu$ is the attenuation coefficient of the substance at energy E. $\rho$ is the density of the substance, and x is the mass thickness (mass per unit area) of the substance.

FIGS. 5A through 7B show the X-ray mass attenuation coefficients of iodine, cerium, and brass plotted vs. photon energy, and the conversion of polyenergetic X-ray beams to quasi-monoenergetic beams with different mean energy spectra by filters containing selected thicknesses of these substances.

FIG. 5A shows a graph 61a of the mass attenuation coefficient of iodine (I, Z=53) as a function of photon energy. The K-absorption edge 61b of iodine is at 33.1 keV.

Figure 5B:
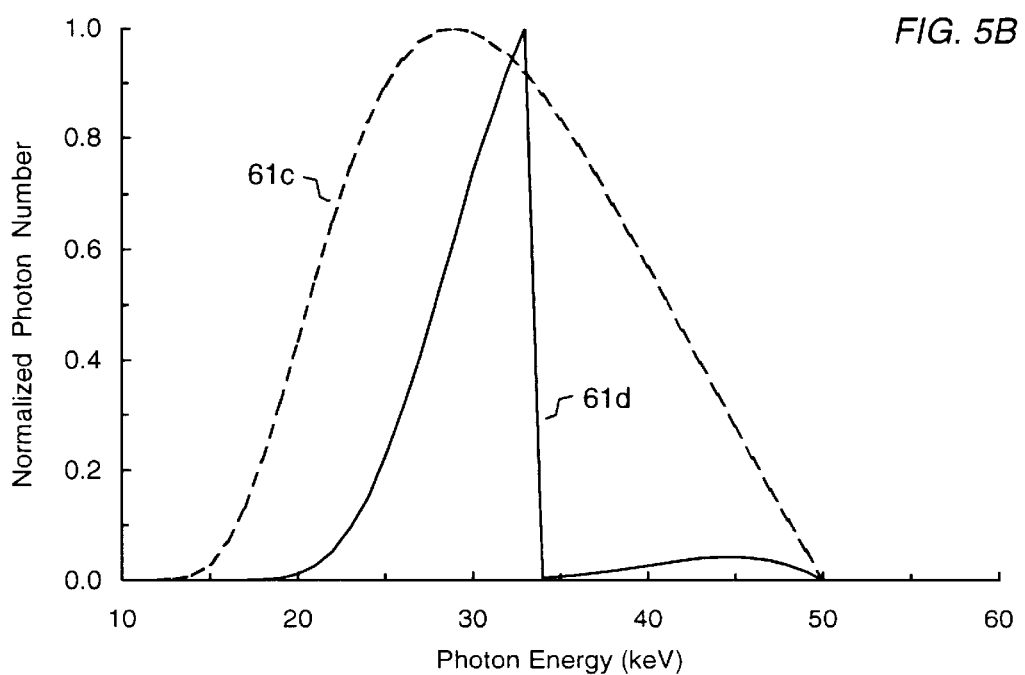
FIG. 5B shows the energy spectra of unfiltered and iodine-filtered X-ray beams.

FIG. 5B shows normalized energy spectra of unfiltered and iodine-filtered X-ray beams. Graph 61c (dashed line) shows the spectrum of an unfiltered beam generated by a tungsten anode source operated at 50 kVp. X-ray filter 41a (FIG. 3B) contains a solution of an iodine compound in which the mass thickness of iodine is 0.200 gm/cm². A polyenergetic 50 kVp beam with spectrum 61c is converted by this filter to a quasi-monoenergetic beam with spectrum 61d, as shown in FIG. 5B. Spectrum 61c of the unfiltered beam is polyenergetic and relatively broad. In contrast, the spectrum of iodine-filtered beam 61d is narrower and quasi-monoenergetic. Iodine-filtered beam 61d has an energy peak at 33 keV and a mean energy spectrum of 31.1 keV.

Figure 6A:
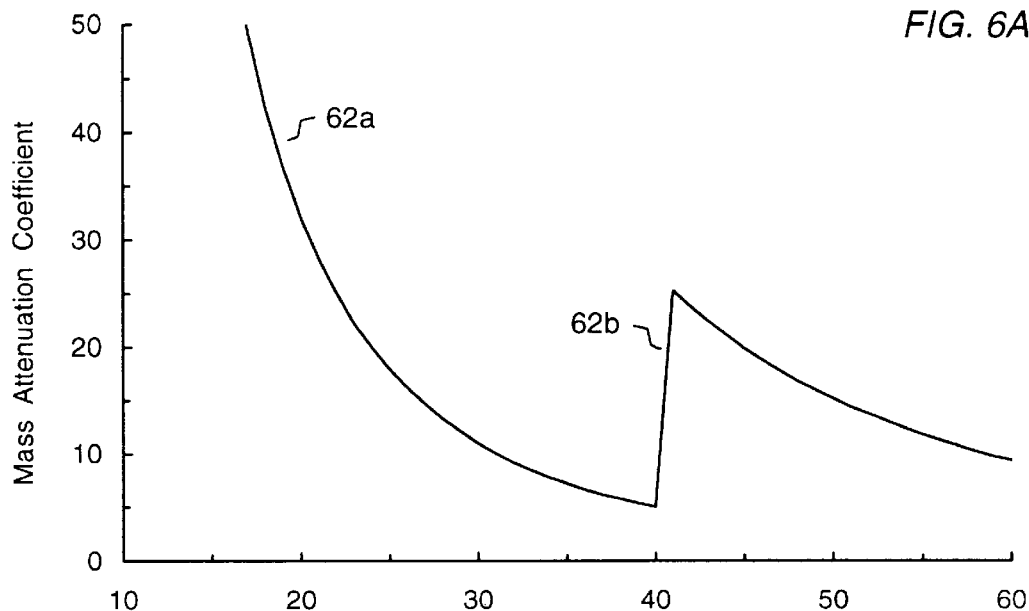
FIG. 6A shows the mass attenuation coefficient of cerium as a function of photon energy.

FIG. 6A shows a graph 62a of the mass attenuation coefficient of cerium (Ce, Z=58) as a function of photon energy. The K-absorption edge 62b of cerium is at 40.0 keV.

Figure 6B:
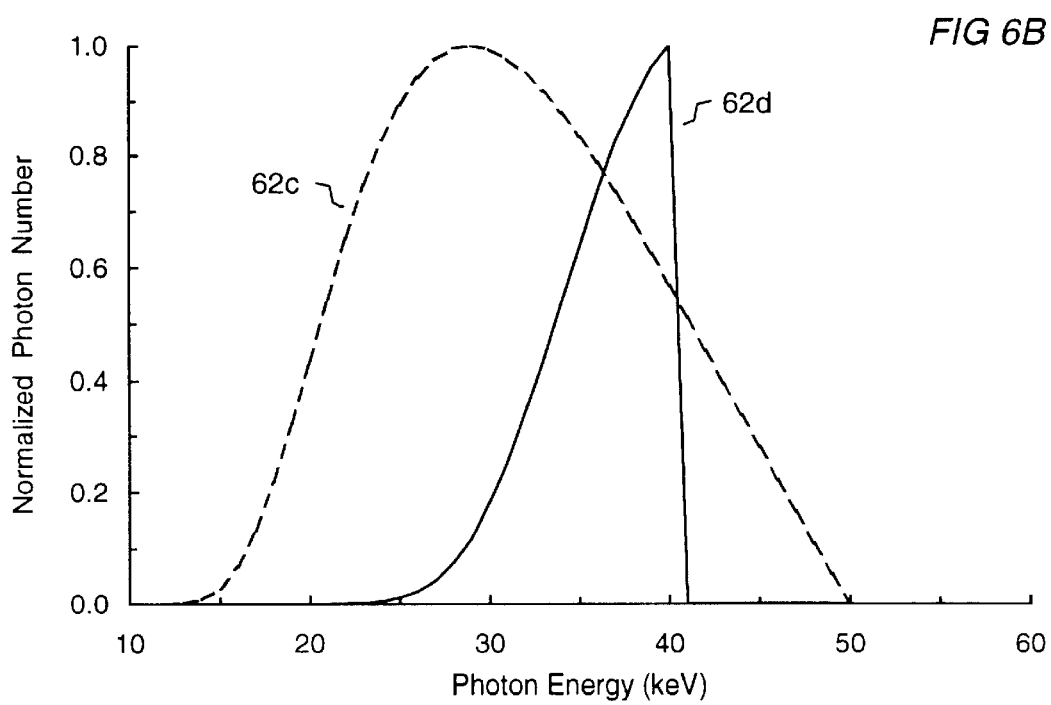
FIG. 6B shows the energy spectra of unfiltered and cerium-filtered X-ray beams.

FIG. 6B shows normalized energy spectra of unfiltered and cerium-filtered beams. X-ray filter 42a contains a solution of a cerium compound in which the mass thickness of cerium is 0.380 gm/cm². A polyenergetic 50 kVp beam with spectrum 62c is converted by this filter to a quasi-monoenergetic beam with spectrum 62d, as shown in FIG. 6B. Cerium-filtered beam 62d has an energy peak at 40 keV and a mean energy spectrum of 36.6 keV.

Figure 7A:
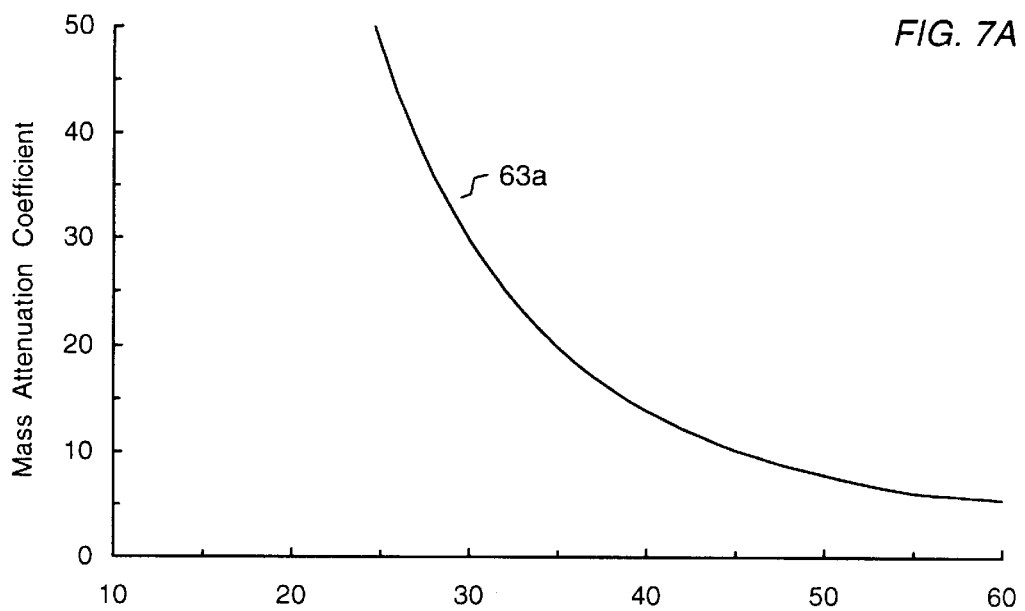
FIG. 7A shows the mass attenuation coefficient of brass as a function of photon energy.

FIG. 7A shows a graph 63a of the mass attenuation coefficient of brass as a function of photon energy. One K-absorption edge of brass is at 8.97 keV (Cu, Z=29) (not shown) and a second K-absorption edge is at 9.65 keV (Zn, Z=30) (not shown).

Figure 7B:
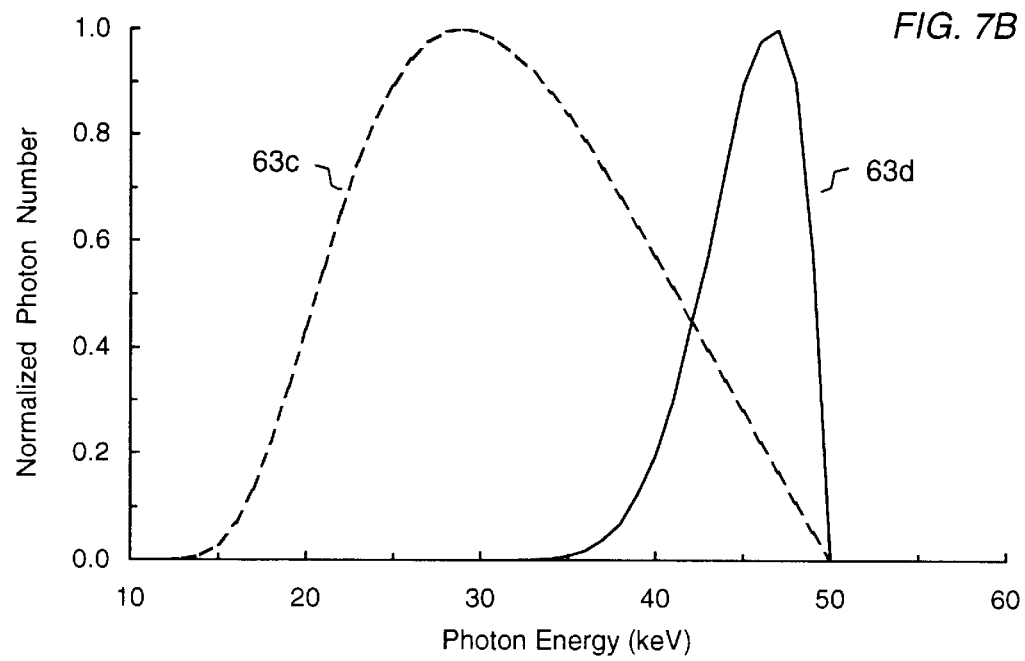
FIG. 7B shows the energy spectra of unfiltered and brass-filtered X-ray beams.

FIG. 7B shows normalized energy spectra of unfiltered and brass-filtered beams. X-ray filter 43a is a thin circular brass disc in which the mass thickness of brass is 1.500 gm/cm². A polyenergetic 50 kVp beam with spectrum 63c is converted by this filter to a quasi-monoenergetic beam with spectrum 63d, as shown in FIG. 7B. Brass-filtered beam 63d has an energy peak at 46 keV and a mean energy spectrum of 45.3 keV.

Table 4 summarizes the filtration parameters for generation of each of the quasi-monoenergetic transilluminating beams from a 50 kVp polyenergetic input beam and the energy characteristics of the filtered beams used to generate display image Z as described in section E.

TABLE 4

| Beam | Filter substance | Thickness gm/cm² | Beam mean E |
|---|---|---|---|
| $E_1$ | Iodine | 0.200 | 31.05 |
| $E_2$ | Cerium | 0.380 | 37.00 |
| $E_3$ | Brass | 1.340 | 45.01 |

It should be understood that the values presented here are only representative and are given as examples. The specific filter thicknesses, beam energies and image weighting coefficients may be varied widely depending on the particular conditions of the imaging procedure. The method for calculation of these values will be apparent to one of ordinary skill in the art.

H. Procedures for Assessment of Tissue Response

The following are examples of the application of the present invention in the assessment of tissue response to compounds. While these examples describe the evaluation of therapeutic compounds, the present invention may also be used for the evaluation of other compounds using similar procedures and protocols.

1. Assessment of Tissue Response to Lead Compounds

The present system and method may be used in validation of lead compounds in the drug discovery process. In this application, images may be acquired before and after administration of a potential lead compound to test animals. Accumulation of the imaging agent in corresponding areas of tissue on the images acquired before and after compound administration may then be compared to assess the efficacy of the lead compound.

One application for the assessment of lead compounds is in the evaluation of anticancer chemotherapeutic lead compounds. Experimental protocols for evaluation of anticancer chemotherapeutic compounds may typically use one of a wide variety of so-called "nude" mouse strains. Nude mice lack a functional thymus and therefore do not reject implanted tissue from a different species. Implanted foreign tissue is known as a xenograft. Suspensions of tumor cells or one or more tumor fragments from tumor-bearing mice or from foreign species, particularly humans, may be implanted in nude mice and allowed to grow for a selected period of time or until the tumors reach a certain size. Alternatively, implanted tumor cells may be obtained from primary cell cultures or from established cell lines. One example of an established cell line commonly used in evaluation of chemotherapeutic agents is the sarcoma 180 line. Cell lines originating from a wide variety of tumor types, and xenografts of a wide variety of tumor types, may be used in this application.

An alternate experimental model may use selected transgenic mouse strains in which malignant tumors spontaneously occur with high frequency. Transgenic strains are available which generate malignant tumors of particular histological types, and which are localized in particular organs of the animal. An example of a transgenic mouse model is the female c-neu Oncomouse. A very high proportion of females in this strain spontaneously develop breast tumors. Another transgenic mouse model is the C57BL/6J-min+multiple intestinal neoplasia strain. Approximately 90% of the mice in this strain develop multiple intestinal neoplasms within 60 days of birth.

Figure 10:
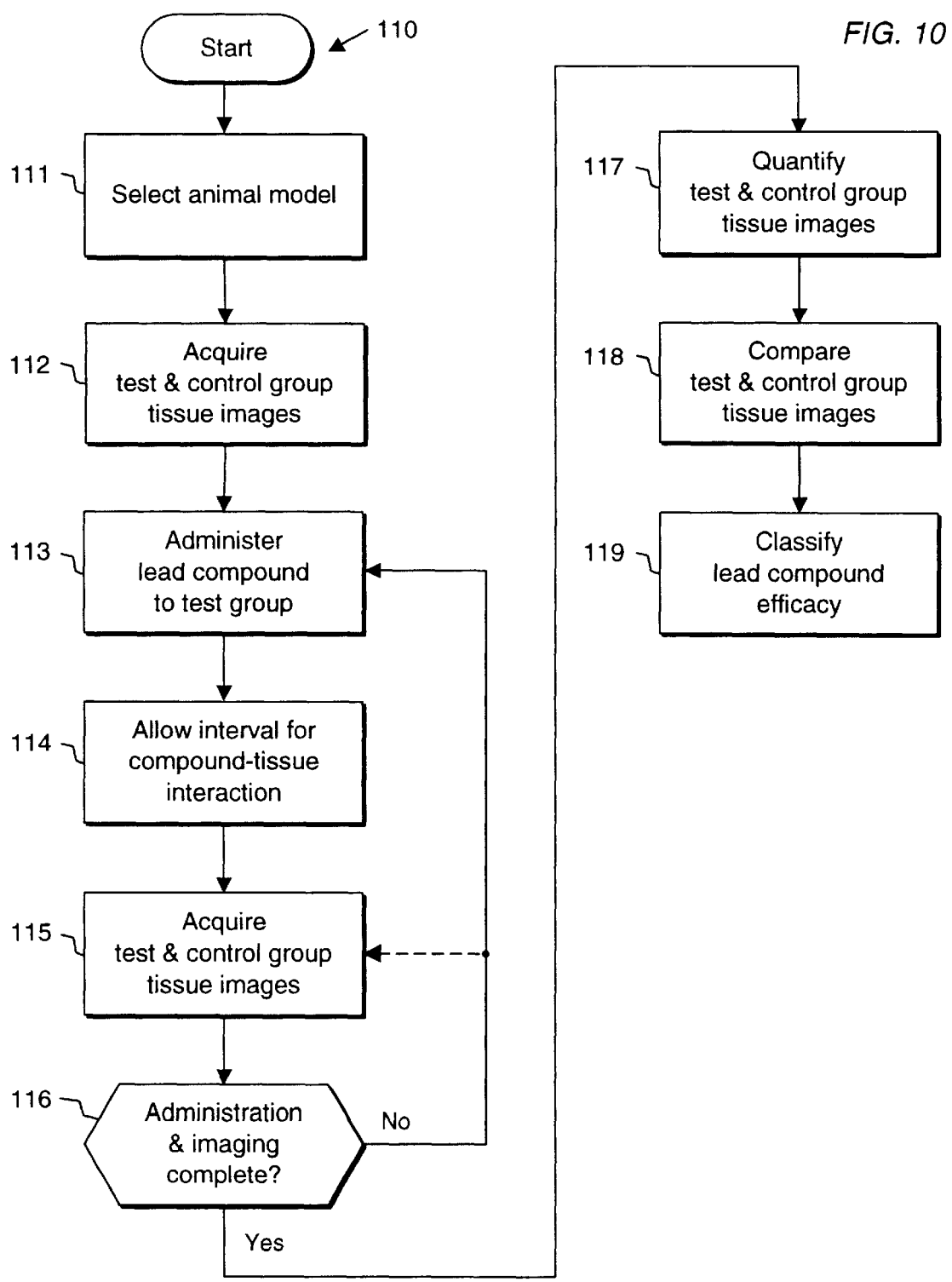
FIG. 10 is a flow chart of a method for assessment of tissue response to a lead compound.

FIG. 10 shows a flow chart of a typical protocol for assessing the efficacy of a lead compound in an animal model. In a typical protocol 110, an appropriate animal model is selected 111 for the lead compound being tested. A control group and a test group of mice may be used. In the test group, a separate subgroup may be used for each planned lead compound dosing protocol.

Spontaneous or implanted tumors are allowed to grow to the approximate desired size in both test and control groups of animals. An imaging procedure according to the present invention, e.g. using a radio-opaque imaging agent which selectively binds to a cellular target, is performed 112 on each animal in the test and control groups to acquire reference images. A lead compound is then administered 113 to each test group animal. Differing dosage levels doses of the lead compound may optionally be administered to selected subgroups of the test group. A time interval is allowed to elapse 114 to enable the lead compound to interact with the tumors. A second imaging procedure using the radio-opaque imaging agent is then performed 115 on each animal in the test and control groups.

Additional doses of the lead compound may be repeatedly administered to the animals in the test group at selected intervals. Images may be acquired after each administration of the compound or independently. In a typical protocol, a selected dosage of a lead compound is repeatedly administered at selected intervals and a tissue image is acquired 3–7 days after each administration of the compound.

Images may continue to be acquired after administration of the lead compound has been terminated. Continued acquisition of images may help in the detection of resistant cell types that have emerged in response to treatment with the lead molecule. This experimental design may be particularly useful in the evaluation of anticancer chemotherapeutic compounds, because it may provide estimates of the probability of emergent drug resistance and occurrence of metastasis after treatment with the lead compound.

When the sequence of compound administration and image acquisition has been completed 116, all acquired images may be quantified 117. Tissue images of the test and control groups may then be compared 118 using one of the methods described in section J. The lead compound may optionally be classified 119 with respect to efficacy based on the results of this comparison.

In certain protocols, the test animals may be killed, possibly to perform studies of histology and gross anatomy, and images are acquired. Accordingly, in some embodiments of the invention, the tissue is transilluminated and images may be acquired when the animal is dead. In some embodiments of the invention, the tissue is transilluminated after it has been removed from the animal and images are acquired.

This example describes the assessment of lead compounds for anticancer chemotherapy. Using analogous experimental designs, the efficacy of many other types of lead compounds for other applications may be noninvasively assessed in vivo.

2. Assessment of Tissue Response in Clinical Trials

The present system and method may also be used in assessing efficacy of potential therapeutic compounds in clinical trials. In this application, radiographic images may be acquired using the present system and method before and after administration of a potential therapeutic compound to patients in a clinical trial. Accumulation of the imaging agent on corresponding areas of tissue in images acquired before and after administration of the trial compound may then be compared to assess the efficacy of the compound. These images may be compared to those acquired from a control group of patients receiving a standard treatment, a placebo, or no treatment.

Figure 11:
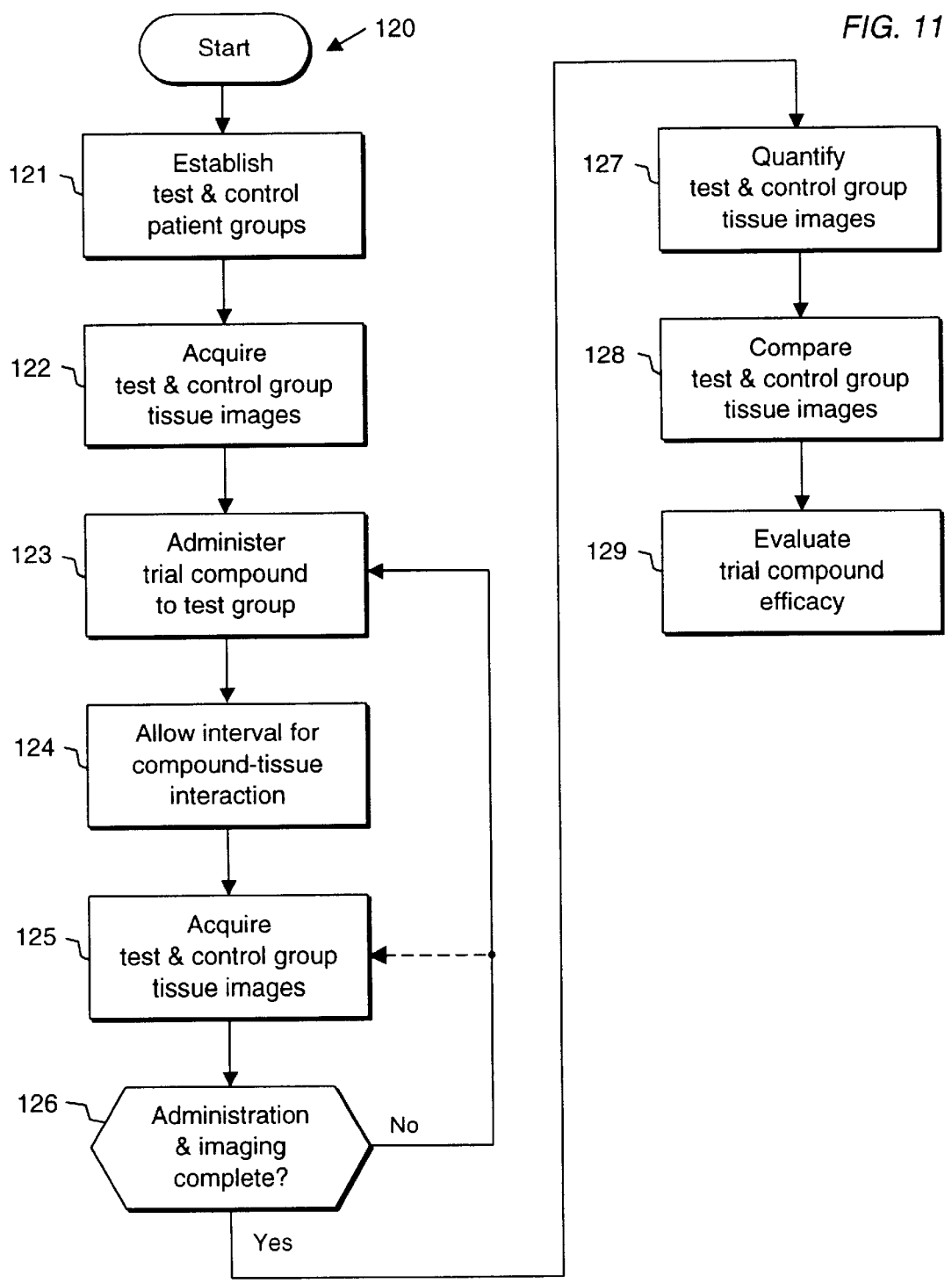
FIG. 11 is a flow chart of a method for assessment of tissue response to a compound in a clinical trial.

FIG. 11 shows a flow chart of a typical clinical trial protocol for assessing the efficacy of a potential therapeutic compound based on the assessment of tissue response. In a typical clinical trial protocol 120, matched control and experimental groups of patients are selected 121. An imaging procedure according to the present invention, e.g. using a radio-opaque imaging agent which selectively binds to a cellular target, is then performed 122 on each patient in both groups. An experimental therapeutic compound is then administered 123 to each patient in the experimental group, while patients in the control group receive a standard treatment. (In certain types of clinical trials, patients in the control group may receive a placebo or remain untreated). Varied dosing protocols may optionally be administered to subgroups of patients in the experimental group. A time interval is then allowed to elapse 124 to enable the experimental therapeutic compound to interact with body tissue of the patient. A second imaging procedure is then performed 125 on each patient in both the experimental and control groups.

The sequence of administering the compound 123, allowing an interval to elapse 124, and acquiring an image 125 is generally repeated multiple times. Administration of the compound and acquisition of images may be performed independently. In addition, images may continue to be acquired, using the methods of the present invention, after the dosing protocol has been terminated, to assess tissue response after treatment has ended. When the compound administration and image acquisition segment of the protocol has been completed 126, the acquired images are quantified 127. Images of tissue from patients in the test and control groups are then compared 128 using one of the methods described in section J. The therapeutic efficacy of the experimental therapeutic compound may then be evaluated 129.

The example presented addresses the assessment of potential therapeutic compounds for anticancer chemotherapy. Using similar methods, the efficacy of many other types of potential therapeutic compounds may be noninvasively assessed in clinical trials, in conjunction with other clinical measures of patient response.

3. Assessment of Tissue Response to Clinical Therapy

The present system and method may also be used in assessing the therapeutic efficacy of a compound in clinical therapeutic applications. In this application, images of tissue in a patient may be acquired before and after administration of a therapeutic compound. Accumulation of the imaging agent in corresponding areas of tissue on images acquired before and after administration of the compound may then be compared to assess the efficacy of the compound.

A typical application for the assessment of therapeutic efficacy is in the evaluation of anticancer chemotherapeutic compounds in individual patients. Patients with cancers of similar organ location and stage of development may vary widely in their response to identical chemotherapy protocols. A wide variety of chemotherapeutic agents, singly and in combination, and in a range of dosage protocols, may be used to treat particular cancers. Cyclophosphamide, doxorubicin, vincristine, and prednisone are representative chemotherapeutic agents that may be used in various combinations to treat lymphoma. Tamoxifen, cyclophosphamide, methotrexate, and fluorouracil are often used in various combinations and dosage levels to treat breast cancer. Because of the many permutations of treatment protocols that are available, and the observed variability in response between patients, it would thus be highly desirable to be able to select the optimum protocol for each individual patient, based on early measurements of their clinical response to a selected protocol.

FIG. 12 shows a flow chart of a typical protocol 130 for assessing the efficacy of a therapeutic regimen in an individual patient. A therapeutic regimen is defined that specifies the selected therapeutic agents, their dosage and frequency of administration. An imaging procedure according to the present invention, e.g. using an imaging agent which selectively binds to a cellular target, is performed 131 on the patient to obtain a reference image of tissue before initiation of therapy. A course of treatment with the selected therapeutic regimen is administered 132, and an interval of time is allowed to elapse 133 to allow tissue response. A second imaging procedure is then performed 134 on the patient. After completion of the first course of treatment, all images acquired during the protocol may be quantified 135 and compared 136. Efficacy of the therapeutic regimen in the patient may then be quantitatively assessed 137. If the response to therapy is determined 138 to be inadequate, and the period for evaluating the regimen has elapsed 139, the therapeutic regimen may be modified or replaced 140.

Administration of the therapeutic regimen and acquisition of images may typically be performed in sequence, but images may also be acquired independently.

The ability to select an optimum therapeutic regimen based on early feedback obtained from noninvasive imaging measurements of patient response should also provide significant advantages in the application of therapeutic compounds in a wide range of other disease processes.

J. Quantitative Analysis of Radiographic Images

Radiographic images acquired during the tissue assessment procedures described in section H may be analyzed using a variety of methods. In these images, low radiographic density on the image reflects high radio-opacity in the illuminated tissue. Quantitative measurements are generally performed on images that have been processed to remove radiographic density contributed by soft tissue and bone, as described in sections E and F. Residual radio-opacity in these images is contributed almost completely by accumulated imaging agent. In one method, the total number of pixels in a user-specified region of interest (ROI) with values above a selected threshold are recorded. The cross-sectional area of tissue in which imaging agent has accumulated above a specific threshold concentration may thereby be calculated. In a second method according to the invention, the pixel values in those pixels located in a user-specified region of interest (ROI) with values above a predetermined threshold are integrated. This method provides an estimate of the total radio-opacity contributed by accumulated imaging agent in the ROI.

Having now fully described the invention, it will be apparent to one of ordinary skill in the art that many changes and modifications can be made thereto without departing from the spirit or scope of the invention as set forth herein.

I claim:

1. A system for radiographic assessment of tissue response to a compound comprising:
   (a) a compound;
   (b) a radio-opaque imaging agent that selectively binds to a cellular target;
   (c) means for administering said imaging agent to an animal;
   (d) means for generating an X-ray beam; and
   (e) means for acquiring a radiographic image disposed on the side of said animal opposite said X-ray beam generating means.

2. The system of claim 1 further including means for assessing a tissue response to said compound.

3. The system of claim 1 wherein said cellular target is a cellular structure.

4. The system of claim 1 wherein said cellular target is selected from the group of proteins, nucleic acids, coenzymes, and lipids.

5. The system of claim 1 wherein said cellular target is an enzyme.

6. The system of claim 1 wherein said cellular target is hexokinase.

7. The system of claim 1 wherein said imaging agent accumulates in abnormal tissue at a different rate than in normal tissue.

8. The system of claim 1 wherein said imaging agent accumulates in abnormal tissue at a different concentration than in normal tissue.

9. The system of claim 1 wherein said imaging agent accumulates in malignant tissue at a different rate than in non-malignant tissue.

10. The system of claim 1 wherein said imaging agent accumulates in malignant tissue at a different concentration than in non-malignant tissue.

11. The system of claim 1 wherein said imaging agent accumulates in abnormal myocardial tissue at a different rate than in normal myocardial tissue.

12. The system of claim 1 wherein said imaging agent accumulates in abnormal myocardial tissue at a different concentration than in normal myocardial tissue.

13. The system of claim 1 wherein said imaging agent has a logP of above 0.0.

14. The system of claim 1 wherein said imaging agent is non-radioactive.

15. The system of claim 1 wherein said imaging agent is bidirectionally cell membrane-permeable.

16. The system of claim 1 wherein said animal is dead during said acquiring of a radiographic image.

17. A system for radiographic assessment of tissue response to a compound comprising:
(a) a compound;
(b) a radio-opaque imaging agent that selectively binds to a cellular target;
(c) means for administering said imaging agent to an animal;
(d) means for generating a plurality of X-ray beams with predetermined different energy spectra;
(e) means for acquiring radiographic images; and
(f) means for performing a weighted combination of a plurality of said radiographic images to produce a single image.

18. The system of claim 17 wherein said plurality of beams are quasi-monoenergetic.

19. The system of claim 17 wherein said plurality of beams are monoenergetic.

20. The system of claim 17 wherein 2 beams are generated.

21. The system of claim 17 wherein more than 2 beams are generated.

22. The system of claim 17 wherein said means for generating a plurality of beams with predetermined different energy spectra is disposed between an X-ray illumination source and said animal.

23. The system of claim 17 wherein said means for generating a plurality of beams with predetermined different energy spectra is disposed between said animal and said means for acquiring radiographic images.

24. The system of claim 17, further including means for displaying variable proportions of radiographic density contributed by said imaging agent, soft tissue, and bone to said single image.

25. The system of claim 17 further including means for assessing a tissue response to said compound.

26. The system of claim 17 wherein said cellular target is selected from the group of proteins, nucleic acids, coenzymes, and lipids.

27. The system of claim 17 wherein said cellular target is an enzyme.

28. The system of claim 17 wherein said cellular target is hexokinase.

29. The system of claim 17 wherein said imaging agent accumulates in abnormal tissue at a different rate than in normal tissue.

30. The system of claim 17 wherein said imaging agent accumulates in abnormal tissue at a different concentration than in normal tissue.

31. The system of claim 17 wherein said imaging agent accumulates in malignant tissue at a different rate than in non-malignant tissue.

32. The system of claim 17 wherein said imaging agent accumulates in malignant tissue at a different concentration than in non-malignant tissue.

33. The system of claim 17 wherein said imaging agent accumulates in abnormal myocardial tissue at a different rate than in normal myocardial tissue.

34. The system of claim 17 wherein said imaging agent accumulates in abnormal myocardial tissue at a different concentration than in normal myocardial tissue.

35. The system of claim 17 wherein said imaging agent has a logP of above 0.0.

36. The system of claim 17 wherein said imaging agent is non-radioactive.

37. The system of claim 17 wherein said radio-opaque imaging agent is bidirectionally cell membrane-permeable.

38. The system of claim 17 wherein said animal is dead during said acquiring of radiographic images.

39. The system of claim 17 wherein tissue within said animal is transilluminated after it has been removed from said animal.

40. A method for radiographic assessment of tissue response to a compound comprising:
(a) administering a compound to an animal;
(b) administering to said animal a radio-opaque imaging agent that selectively binds to a cellular target;
(c) generating an X-ray beam;
(d) illuminating tissue of said animal with said X-ray beam; and
(e) acquiring a radiographic image of said tissue during illumination.

41. The method of claim 40, further including allowing an interval for said compound to interact with said tissue.

42. The method of claim 40, further including repeating (a) at least once.

43. The method of claim 40 further including:
repeating (b) through (e) at least once; and
comparing at least two of the acquired radiographic images.

44. The method of claim 43 wherein said comparing includes measuring the radiographic density of corresponding areas of tissue displayed in at least two of said radiographic images.

45. The method of claim 40 wherein said radiographic image is analyzed to assess a tissue response to said compound.

46. The method of claim 40 wherein said cellular target is a cellular structure.

47. The method of claim 40 wherein said cellular target is selected from the group of proteins, nucleic acids, coenzymes, and lipids.

48. The method of claim 40 wherein said cellular target is an enzyme.

49. The method of claim 40 wherein said cellular target is hexokinase.

50. The method of claim 40 wherein said imaging agent accumulates in abnormal tissue at a different rate than in normal tissue.

51. The method of claim 40 wherein said imaging agent accumulates in abnormal tissue at a different concentration than in normal tissue.

52. The method of claim 40 wherein said imaging agent accumulates in malignant tissue at a different rate than in non-malignant tissue.

53. The method of claim 40 wherein said imaging agent accumulates in malignant tissue at a different concentration than in non-malignant tissue.

54. The method of claim 40 wherein said imaging agent accumulates in abnormal myocardial tissue at a different rate than in normal myocardial tissue.

55. The method of claim 40 wherein said imaging agent accumulates in abnormal myocardial tissue at a different concentration than in normal myocardial tissue.

56. The method of claim 40 wherein said imaging agent has a logP of above 0.0.

57. The method of claim 40 wherein said imaging agent is non-radioactive.

58. The method of claim 40 wherein said radio-opaque imaging agent is bidirectionally cell membrane-permeable.

59. The method of claim 40 wherein said animal is dead during said acquiring of radiographic images.

60. The method of claim 40 wherein said illuminating is performed after removal of said tissue from said animal.

61. A method for radiographic assessment of tissue response to a compound comprising:
  (a) administering a compound to an animal;
  (b) administering a radio-opaque imaging agent to said animal;
  (c) generating a plurality of X-ray beams with predetermined different energy spectra;
  (d) illuminating tissue of said animal with each of said plurality of X-ray beams;
  (e) acquiring a radiographic image of said tissue during illumination by each of said plurality of beams; and
  (f) performing a weighted combination of a plurality of said radiographic images to produce a single image.

62. The method of claim 61 wherein said plurality of beams are quasi-monoenergetic.

63. The method of claim 61 wherein said plurality of beams are monoenergetic.

64. The method of claim 61 wherein 2 beams are generated.

65. The method of claim 61 wherein more than 2 beams are generated.

66. The method of claim 61, further displaying variable proportions of radiographic density contributed by said imaging agent, soft tissue, and bone to said single image.

67. The method of claim 61, further including allowing an interval for said compound to interact with said tissue.

68. The method of claim 61 further including repeating (a) at least once.

69. The method of claim 61 further including:
  repeating (b) through (f) at least once; and
  comparing at least two of the acquired radiographic images.

70. The method of claim 69 wherein said comparing includes measuring the radiographic density of corresponding areas of tissue displayed in at least two of said radiographic images.

71. The method of claim 61 wherein said radiographic image is analyzed to assess a tissue response to said compound.

72. The method of claim 61 wherein said cellular target is a cellular structure.

73. The method of claim 61 wherein said single image is analyzed to assess tissue response to said compound.

74. The method of claim 61 wherein said cellular target is selected from the group of proteins, nucleic acids, coenzymes, and lipids.

75. The method of claim 61 wherein said cellular target is an enzyme.

76. The method of claim 61 wherein said cellular target is hexokinase.

77. The method of claim 61 wherein said imaging agent accumulates in abnormal tissue at a different rate than in normal tissue.

78. The method of claim 61 wherein said imaging agent accumulates in abnormal tissue at a different concentration than in normal tissue.

79. The method of claim 61 wherein said imaging agent accumulates in malignant tissue at a different rate than in non-malignant tissue.

80. The method of claim 61 wherein said imaging agent accumulates in malignant tissue at a different concentration than in non-malignant tissue.

81. The method of claim 61 wherein said imaging agent accumulates in abnormal myocardial tissue at a different rate than in normal myocardial tissue.

82. The method of claim 61 wherein said imaging agent accumulates in abnormal myocardial tissue at a different concentration than in normal myocardial tissue.

83. The method of claim 61 wherein said imaging agent has a logP of above 0.0.

84. The method of claim 61 wherein said imaging agent is non-radioactive.

85. The method of claim 61 wherein said radio-opaque imaging agent is bidirectionally cell membrane-permeable.

86. The method of claim 61 wherein said radio-opaque imaging agent binds to a cellular target.

87. The method of claim 61 wherein said animal is dead during acquiring of radiographic images.

88. The method of claim 61 wherein said tissue is illuminated after having been removed from said animal.

89. A computer-readable storage medium containing executable computer instructions which, when executed by a digital image processing system, cause said digital image processing system to perform a method comprising:
  (a) acquiring a plurality of radiographic images, wherein each of said radiographic images is acquired during transillumination of tissue in a dead animal by one of a plurality of X-ray beams with a predetermined unique energy spectrum, said animal having been previously administered a compound and having been administered a radio-opaque imaging agent;
  (b) generating a single image from said plurality of radiographic images.

90. A computer-readable storage medium containing executable computer instructions which, when executed by a digital image processing system, cause said digital image processing system to perform a method comprising:
  (a) acquiring a plurality of radiographic images, wherein each of said radiographic images is acquired during transillumination of tissue removed from an animal by one of a plurality of X-ray beams with a predetermined unique energy spectrum, said animal having been administered a compound and having been administered a radio-opaque imaging agent;
  (b) generating a single image from said plurality of radiographic images.

* * * * *